United States Patent
Nishino et al.

(10) Patent No.: US 9,328,085 B2
(45) Date of Patent: May 3, 2016

(54) HETEROCYCLIC COMPOUNDS AND EXPANSION AGENTS FOR HEMATOPOIETIC STEM CELLS

(71) Applicant: NISSAN CHEMICAL INDUSTRIES, LTD., Tokyo (JP)

(72) Inventors: Taito Nishino, Tokyo (JP); Shunsuke Iwamoto, Funabashi (JP); Katsuaki Miyaji, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 252 days.

(21) Appl. No.: 13/875,387

(22) Filed: May 2, 2013

(65) Prior Publication Data

US 2013/0245255 A1 Sep. 19, 2013

Related U.S. Application Data

(63) Continuation of application No. 13/376,280, filed as application No. PCT/JP2010/059552 on Jun. 4, 2010, now abandoned.

(30) Foreign Application Priority Data

Jun. 4, 2009 (JP) ................................ 2009-135495

(51) Int. Cl.

| C12N 5/00 | (2006.01) |
|---|---|
| C07D 333/32 | (2006.01) |
| C07D 333/38 | (2006.01) |
| C07D 409/12 | (2006.01) |
| C07D 409/14 | (2006.01) |
| C12N 5/0789 | (2010.01) |

(52) U.S. Cl.
CPC ............ *C07D 333/32* (2013.01); *C07D 333/38* (2013.01); *C07D 409/12* (2013.01); *C07D 409/14* (2013.01); *C12N 5/0647* (2013.01); *C12N 2501/999* (2013.01)

(58) Field of Classification Search
None
See application file for complete search history.

(56) References Cited

U.S. PATENT DOCUMENTS

| 5,199,942 | A | 4/1993 | Gillis |
| 5,399,493 | A | 3/1995 | Emerson et al. |
| 5,437,994 | A | 8/1995 | Emerson et al. |
| 5,646,043 | A | 7/1997 | Emerson et al. |
| 5,670,147 | A | 9/1997 | Emerson et al. |
| 5,670,351 | A | 9/1997 | Emerson et al. |
| 6,326,198 | B1 | 12/2001 | Emerson et al. |
| 7,351,841 | B2 * | 4/2008 | Owada et al. ............ 549/62 |
| 2002/0022270 | A1 | 2/2002 | Emerson et al. |
| 2007/0155739 | A1 | 7/2007 | Sucholeiki et al. |
| 2007/0166825 | A1 | 7/2007 | Hatsuyama et al. |
| 2009/0118500 | A1 | 5/2009 | Miyaji et al. |
| 2009/0131659 | A1 | 5/2009 | Miyaji et al. |
| 2010/0266556 | A1 | 10/2010 | Nishino et al. |

FOREIGN PATENT DOCUMENTS

| CN | 101223154 A | 7/2008 |
| JP | 6 505151 | 6/1994 |
| JP | 6 508613 | 9/1994 |
| JP | 2000 23674 | 1/2000 |
| JP | 2001 161350 | 6/2001 |
| JP | 2002 502617 | 1/2002 |
| JP | 2004 222502 | 8/2004 |
| JP | 2005 204539 | 8/2005 |
| JP | 2009 501131 | 1/2009 |
| JP | 2009 40692 | 2/2009 |
| WO | WO 97/16535 A2 | 5/1997 |
| WO | 2006 064957 | 6/2006 |
| WO | 2007/010954 | 1/2007 |

(Continued)

OTHER PUBLICATIONS

Office Action issued Apr. 12, 2013, in Chinese Patent Application No. 201080025055.8 (submitting English translation only).
Hatsuyama, A., et al., "The characteristics of cord blood stem cell expanded with complete serum-free medium," Rinsho Ketsueki, vol. 44, No. 8, p. 729, (2003).
Lu, L. et al., "The Selective Enhancing Influence of Hemin and Products of Human Erythrocytes on Colony Formation by Human Multipotential (CFUGEMM) and Erythroid (BFUE) Progenitor Cells In Vitro," Exp. Hematol., vol. 11, No. 8, pp. 721-729, (Sep. 1983).

(Continued)

*Primary Examiner* — Lora E Barnhart Driscoll
(74) *Attorney, Agent, or Firm* — Oblon, McClelland, Maier & Neustadt, L.L.P.

(57) ABSTRACT

An expansion agent for hematopoietic stem cells and/or hematopoietic progenitor cells useful for improvement in the efficiency of gene transfer into hematopoietic stem cells for gene therapy useful for treatment of various disorders is provided. An expansion agent for hematopoietic stem cells and/or hematopoietic progenitor cells is provided, containing a compound represented by the formula (I):

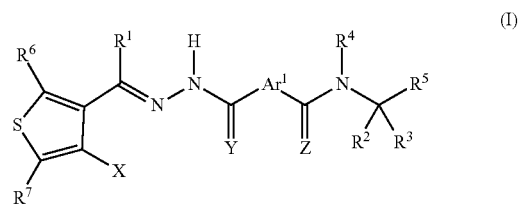

Figure 1:
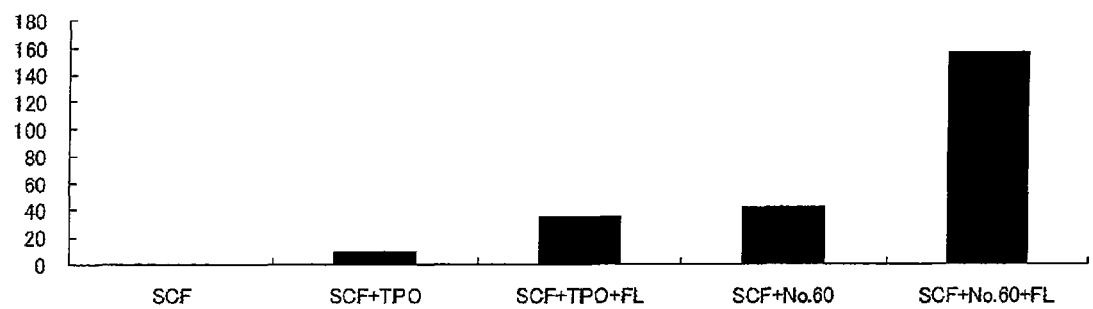

(wherein X, Y, Z, $Ar_1$, $R_1$, $R^2$, $R^3$, $R^4$, $R^5$, $R^6$ and $R^7$ are as defined in the description), a tautomer, amide, ester, or pharmaceutically acceptable salt of the compound or a solvate thereof, which can expand hematopoietic stem cells and/or hematopoietic progenitor cells.

25 Claims, 1 Drawing Sheet

(56) References Cited

FOREIGN PATENT DOCUMENTS

| WO | 2007 079199 | 7/2007 |
|---|---|---|
| WO | 2009 072624 | 6/2009 |
| WO | 2009 072626 | 6/2009 |
| WO | 2009 072635 | 6/2009 |

OTHER PUBLICATIONS

Taguchi, A., et al., "Administration of CD34+ cells after stroke enhances neurogenesis via angiogenesis in a mouse model," The Journal of Clinical Investigation, vol. 114, No. 3, pp. 330-338, (Aug. 2004).

Orlic, D., et al., "Bone marrow cells regenerate infarcted myocardium," Nature, vol. 410, pp. 701-705, (Apr. 5, 2001).

Tateishi-Yuyama, E., et al., "Therapeutic angiogenesis for patients with limb ischaemia by autologous transplantation of bone-marrow cells: a pilot study and a randomised controlled trial," The Lancet, vol. 360, pp. 427-435 (Aug. 10, 2002).

Iwasaki, H., et al., "Dose-Dependent Contribution of CD34-Positive Cell Transplantation to Concurrent Vasculogenesis and Cardiomyogenesis for Functional Regenerative Recovery After Myocardial Infarction," Circulation, vol. 113, pp. 1311-1325 and 1275-1277, (2006).

Kurtzberg, J., et al., "Placental Blood as a Source of Hematopoietic Stem Cells for Transplantation into Unrelated Recipients," New England Journal of Medicine, vol. 335, No. 3, pp. 157-166, (Jul. 18, 1996).

Nathwani, A.C., et al., "A review of gene therapy for haematological disorders," British Journal of Haematology, vol. 128, pp. 3-17, (2004).

Delaney, C., et al., "Notch-mediated expansion of human cord blood progenitor cells capable of rapid myeloid reconstitution," Nature Medicine, vol. 16, No. 2, pp. 232-236, (Feb. 2010).

Ema, H., et al., "Colony Formation of Clone-Sorted Human Hematopoietic Progenitors," Blood, vol. 75, No. 10, pp. 1941-1946 (May 15, 1990).

Ishizawa, L., et al., " Immunomagnetic Separation of CD34+ Cells from Human Bone Marrow, Cord Blood, and Mobilized Peripheral Blood," Journal of Hematotherapy, vol. 21, pp. 333-338, (1993).

Cassel, A., et al., "Retroviral-mediated gene transfer into CD34-enriched human peripheral blood stem cells," Experimental Hematology, vol. 21, pp. 585-591, (1993).

Bhatia, M., et al., "Purification of primitive human hematopoietic cells capable of repopulating immune-deficient mice," Proc. Natl. Acad. Sci. USA, vol. 94, pp. 5320-5325, (May 1997).

Larochelle, A., et al., "Identification of primitive human hematopoietic cells capable of repopulating NOD/SCID mouse bone marrow: Implications for gene therapy," Nature Medicine, vol. 2, No. 12, pp. 1329-1337, (Dec. 1996).

Shah, A.J., et al., "FLt3 Ligand Induces Proliferation of Quiescent Human Bone Marrow CD34+CD38-Cells and Maintains Progenitor Cells In Vitro," Blood, vol. 87, No. 9, pp. 3563-3570, (May 1, 1996).

Dick, J.E., et al., "Assay of Human Stem Cells by Repopulation of NOD/SCID Mice," Stem Cells, vol. 15, pp. 199-207, (1997).

Suzuki, T., et al., "Highly Efficient Ex Vivo Expansion of Human Hematopoietic Stem Cells Using Deltal-Fc Chimeric Protein," Stem Cells, vol. 24, pp. 2456-2465, (2006).

McNiece., I., et al., "Ex vivo expanded peripheral blood progenitor cells provide rapid neutrophil recovery after high-dose chemotherapy in patients with breast cancer," Blood, vol. 96, No. 9, pp. 3001-3007, (Nov. 1, 2000).

Kaushansky, K., "Thrombopoietin and the Hematopoietic Stem Cell," Ann NY Acad. Sci., vol. 1044, pp. 139-141, (2005).

Kawano, Y., et al., "Ex vivo expansion of G-CSF-mobilized peripheral blood CD133+ progenitor cells on coculture with human stromal cells," Experimental Hematology, vol. 34, pp. 150-158, (2006).

Kawada, H., et al., "Rapid ex vivo expansion of human umbilical cord hematopoietic progenitors using a novel culture system," Experimental Hematology, vol. 27, pp. 904-915, (1999).

Chute, J.P., et al., "Inhibition of aldehyde dehydrogenase and retinoid signaling induces the expansion of human hematopoietic stem cells," Proc. Natl. Acad. Sci. USA, vol. 103, No. 31, pp. 11707-11712, (Aug. 1, 2006).

Milhem, M., et al., "Modification of hematopoietic stem cell fate by 5aza 2'deoxycytidine and trichostatin A," Blood, vol. 103, No. 11, pp. 4102-4110, (Jun. 1, 2004).

Leung, A.Y.H., et al., "All-trans retinoic acid (ATRA) enhances maintenance of primitive human hematopoietic progenitors and skews them towards myeloid differentiation in a stroma-noncontact culture system," Experimental Hematology, vol. 33, pp. 422-427, (2005).

Appelbaum, F.R., "The Use of Colony Stimulating Factors in Marrow Transplantation," Cancer Supplement, vol. 72, No. 11, pp. 3387-3392, (Dec. 1, 1993).

International Search Report Issued on Aug. 10, 2010 in PCT/JP10/59552 Filed Jun. 4, 2010.

Supplementary European Search Report issued May 22, 2012 in European Patent Application No. 10783467.3.

Taito Nishino, et al., "Ex vivo expansion of human hematopoietic stem cells by a small-molecule agonist of c-MPL", Experimental Hematology, vol. 37, No. 11, XP-026691949, Nov. 1, 2009, pp. 1364-1377. E4.

Aggarwal et al. 2012. Hematopoietic stem cells: transcriptional regulation, ex vivo expansion and clinical application. Curr Mol Med 12:34-49; author manuscript available online at http://www.ncbi.nlm.nih.gov/pmc/articles/PMC3286491/pdf/nihms356893.pdf.

Kanji S et al. 2011. Plasticity and maintenance of hematopoietic stem cells during development. Recent Pat Biotechnol. 5: 40-53; author manuscript available online at http://www.ncbi.nlm.nih.gov/pmc/articlesPMC3294454/pdf/nihms-356918.pdf.

Nishino T et al. 2009. Ex vivo expansion of human hematopoietic stem cells by a small-molecule agonist of c-MPL. Exp Hematol 37:1364-1377.

Nishino T et al. 2012. New approaches to expand hematopoietic stem and progenitor cells. Expert Op Biol Therap 12: 743-756.

\* cited by examiner

HETEROCYCLIC COMPOUNDS AND EXPANSION AGENTS FOR HEMATOPOIETIC STEM CELLS

This application is a Continuation of Ser. No. 13/376,280 filed on Dec. 5, 2011, which is a 371 of International PCT/JP10/059,552 filed Jun. 4, 2010, which are incorporated herein by reference.

BACKGROUND OF THE INVENTION

1. Technical Field

The present invention relates to an expansion agent for hematopoietic stem cells and/or hematopoietic progenitor cells using a low molecular weight compound having a blood cell expanding effect, in particular, to a cell therapy material containing a compound expanding hematopoietic stem cells and/or hematopoietic progenitor cells as an active ingredient for treating various diseases with expanded hematopoietic stem cells and/or hematopoietic progenitor cells, a gene therapy material for treating various diseases by transferring a gene into hematopoietic stem cells and/or hematopoietic progenitor cells by using the compound and a pharmaceutical agent.

2. Background Art

Blood contains various lineages of blood cells having biological functions, such as the erythrocytic lineage associated with oxygen delivery, the megakaryocytic lineage generating thrombocytes, the granulocytic lineage associated with prevention of infections, the myeloid lineage such as monocytes and/or macrophages and the lymphocytic lineage responsible for immunity such as T cells and B cells. All these blood cells differentiate and mature from the common origin, hematopoietic stem cells, and are maintained and generated in an individual throughout its life. Hematopoietic stem cells are defined as cells having both pluripotency which allows them to differentiate into functional cells such as lymphocytes, erythrocytes and leukocytes and the ability to regenerate themselves while maintaining the pluripotency (self-renewal).

Previous studies have revealed that hematopoietic stem cells first diverge two ways into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-EO), while lymphoid stem cells differentiate into T cells via T lymphoid progenitor cells and into B cells via B lymphoid progenitor cells. Among them, cells forming multipotential colonies with diameters of at least 1 mm are called HPP-CFU colony forming cells and are known as the least differentiated hematopoietic progenitor cells, along with mixed colony forming cells (CFU-GEMM). These myeloid stem cells and various hematopoietic progenitor cells derived from them are identified by the properties of colonies they form on soft agar, semisolid methylcellulose media or the like in the presence of various cytokines (Non-Patent Document 1).

In recent years, as a curative therapy for a number of intractable diseases such as various blood diseases attributed to hematopoietic dysfunction and immune dysfunction, cancer, immunodeficiency, autoimmune diseases and inborn error of metabolism, autologous or allogeneic transplantation of hematopoietic stem cells have been carried out. Quite recently, the effectiveness of transplantation of $CD34^+$ cells including hematopoietic stem cells in treating cerebral infarction, myocardial infarction and obstructive arteriosclerosis was reported (Non-Patent Documents 2, 3, 4 and 5). Attempts to regenerate nerves and muscles through hematopoietic stem cell transplantation are under way. For example, nerve regeneration in cerebral infarction model mice through angiogenesis caused by transplantation of cord blood-derived $CD34^+$ cells (Non-Patent Document 2) and the possibility of repair of damaged muscles using $CD34^+$ cells are reported (Non-Patent Document 5 and Patent Document 1). Among them, bone marrow transplantation has been used in many cases of treatment and most established as a standard hematopoietic cell transplantation therapy. However, because for bone marrow transplantation, the human leukocyte antigens (HLA) of the bone marrow donor and the transplant recipient have to match closely, there is a problem that bone marrow from donors are in short supply. Besides, the need for at least 4 days of hospitalization and pain, fever and bleeding caused by collection of a large amount of bone marrow are a heavy burden to donors.

In addition to bone marrow, peripheral blood is also used as an alternative source of hematopoietic stem cells nowadays. Hematopoietic stem cells mobilized from the bone marrow to peripheral blood by administration of granulocyte colony stimulating factor (G-CSF) to a human are used for transplantation after enrichment using a blood cell separator. However, donors for peripheral blood hematopoietic stem cell transplantation have to bear a heavy burden of the need for administration of G-CSF for 4 to 6 consecutive days which may cause side effects (such as blood coagulation and spleen hypertrophy). Besides, because the efficiency of the mobilization of hematopoietic stem cells from the bone marrow to peripheral blood by G-CSF varies from donor to donor, hematopoietic stem cells are not obtained sufficiently in some cases.

Just recently, it was found that cord blood contains as many hematopoietic stem cells as bone marrow and is useful for hematopoietic stem cell transplantation (Non-Patent Document 6). Because cord blood transplantation does not require complete HLA matching and is less likely to cause severe acute graft-versus-host disease (GVHD) than bone marrow and peripheral blood transplantation, cord blood is established as useful and has been used more frequently. However, because cord blood is obtained in a small amount from one donor and does not contain many hematopoietic stem cells, its use is mainly limited to children.

Furthermore, hematopoietic stem cells are also considered as useful cells for gene therapy of fatal genetic diseases with no effective cure, HIV infection, chronic granulomatosis and germ cell tumor. However, in order to transfect hematopoietic stem cells with a retrovirus vector carrying a target gene efficiently, it is necessary to artificially grow hematopoietic stem cells, which are usually in the stationary phase, by recruiting them into the cell cycle. Besides, in order to be successfully transplanted and express a transgene for a long time, the transfected hematopoietic stem cells have to be kept undifferentiated in culture ex vivo. Therefore, gene transfer by an improved cell culture method has been desired for efficient gene transfer and successful transplantation therapy (Non-Patent Document 7).

Meanwhile, hematopoietic progenitor cells are important for initial hematopoietic recovery after bone marrow or cord blood transplantation and are considered as effective, especially, in preventing early posttransplant infections. Therefore, transplantation of an insufficient number of hematopoietic progenitor cells can delay initial hematopoietic recovery and lower the posttransplant survival rate (Non-Patent Document 8).

To solve the above-mentioned problems with hematopoietic stem cell transplantation and gene therapy, a technique for expanding hematopoietic stem cells and/or hematopoietic progenitor cells ex vivo is demanded, and various culture methods have been attempted so far.

Here, hematopoietic stem cells and hematopoietic progenitor cells, which are to be cultured, are explained. It was revealed that in human, hematopoietic stem cells and various hematopoietic progenitor cells derived from them are found in populations of $CD34^+$ cells expressing the CD34 molecule as a cell surface antigen, and hence hematopoietic stem cells can be enriched as a $CD34^+$ cell population (Non-Patent Document 9). Specifically speaking, they are often enriched by mixing a cell population to be separated with a CD34 antibody labeled with magnetic beads and magnetically collecting $CD34^+$ cells (Non-Patent Documents 10 and 11). $CD34^+$ cell populations contain less than 10% of $CD34^+$ $CD38^-$ cell populations not expressing the CD38 molecule as a cell surface antigen. It has come to be considered that hematopoietic stem cells are more enriched in $CD34^+CD38^-$ cell populations than in $CD34^+$ cell populations (Non-Patent Documents 12 and 13). In order to determine the proportion of undifferentiated hematopoietic progenitor cells in a cell population, HPP-CFU colony forming cells are usually counted as mentioned above (Non-Patent Document 14). In recent years, it has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells (Non-Patent Document 15).

Conventional techniques for expanding hematopoietic stem cells and/or hematopoietic progenitor cells will also be explained. As mentioned above, since hematopoietic stem cells are more enriched in $CD34^+$ cells, $CD34^+$ cells are mainly used as the starting cells for expansion. Expansion of hematopoietic stem cells and hematopoietic progenitor cells from $CD34^+$ cells in culture in the presence of a cytokine or a growth factor such as stem cell factor (SCF), interleukin-3 (IL-3), interleukin-6 (IL-6), interleukin-6 (IL-6)/soluble IL-6 receptor complex, interleukin-11 (IL-11), granulocyte colony stimulating factor (G-CSF), granulocyte-macrophage colony stimulating factor (GM-CSF), flk2/flt3 ligand (FL), thrombopoietin (TPO) and erythropoietin or Notch ligand (such as Delta 1) has been reported (Patent Documents 2 and 3 and Non-Patent Documents 8, 14, 16 and 17). Among them, TPO has especially excellent effect on hematopoietic stem cell expansion and used for in most of cases of expansion (Non-Patent Document 18). Hematopoietic stem cells and hematopoietic progenitor cells expand in culture in the presence of such various cytokines and growth factors, but hematopoietic stem cells expand only by several times. Besides, these cytokines and growth factors are all produced as recombinant proteins, it may be difficult to obtain them for expansion stably, in a large amount, at low cost, or quickly.

For ex vivo expansion of hematopoietic stem cells, coculture systems using a different type of cells as feeder cells in the presence of various cytokines were reported. For example, expansion of hematopoietic stem cells in coculture with human bone marrow stromal cells was attempted (Non-Patent Document 19). An attempt to expand $CD34^+$ cells in the presence of TPO, FL and SCF using mouse bone marrow cell line HESS-5 was also reported (Non-Patent Document 20). However, because these coculture systems use foreign cells, there is a risk that cells infected with an unknown pathogen whose existence has not been confirmed may also be transplanted to patients. Furthermore, when stromal cells from a different kind of animal are used, the stromal cells have to be separated completely from $CD34^+$ cells because otherwise there is a risk of causing immune response in the recipient after transplantation.

In addition, ex vivo expansion of hematopoietic stem cells in culture in the presence of various cytokines such as TPO combined with low molecular weight compounds, not just various cytokines only, has been reported. Examples of such low molecular weight compounds include copper chelators, the combination of a histone deacetylase inhibitor and a DNA methylase inhibitor, all-trans retinoic acid, aldehyde dehydrogenase inhibitors (Non-Patent Documents 21, 22 and 23 and Patent Document 4). However, addition of any of them is not effective enough since hematopoietic stem cells expand by only several times, or cells have to be cultured for about 3 weeks.

It is known that treatments which promote rapid hematopoietic and immune recovery after transplantation of hematopoietic stem cells are quite effective in eliminating the risk of infections and shortening hospitalization. As such a treatment, posttransplant administration of the hematopoietic cytokine, granulocyte colony stimulating factor (G-CSF), is conducted in clinical settings (Non-Patent Document 24). However, it is effective only for leukocytes, and effective treatments which promote recovery of blood cells of all lineages through expansion of hematopoietic stem cells and/or hematopoietic progenitor cells are demanded. Effective therapies for diseases and dysfunctions accompanied by decrease in hematopoietic stem cells and/or hematopoietic progenitor cells, other than hematopietic stem cell transplantation, are also demanded.

PRIOR ART DOCUMENTS

Patent Document(s)

Patent Document 1: JP-A-2009-40692
Patent Document 2: JP-A-2001-161350
Patent Document 3: JP-A-2000-23674
Patent Document 4: JP-A-2002-502617

Non-Patent Document(S)

Non-Patent Document 1: Lu, L. et al.; Exp. Hematol., 11, 721-9, 1983
Non-Patent Document 2: Taguchi, A et al.; J Clin Invest., 114, 330-8, 2004
Non-Patent Document 3: Orlic, D et al.; Nature, 410, 701-5, 2001
Non-Patent Document 4: Tateishi-Yuyama, E et al.; Lancet, 360, 427-35, 2002
Non-Patent Document 5: Iwasaki, H et al.; Circulation, 113, 1311-1325, 2006
Non-Patent Document 6: Kurtzbert, J. et al.; New Eng. J. Med., 335, 157-66, 1996
Non-Patent Document 7: Nathwani, A C. et al.; Br J. Haematol., 128, 3-17, 2005
Non-Patent Document 8: Delaney, C. et al.; Nat. Med., 16, 232-6, 2010
Non-Patent Document 9: Ema, H. et al.; Blood, 75, 1941-6, 1990

Non-Patent Document 10: Ishizawa, L. et al.; J. Hemather., 2, 333-8, 1993

Non-Patent Document 11: Cassel, A. et al.; Exp. Hematol., 21, 585-91, 1993

Non-Patent Document 12: Bhatia, M. et al.; Proc. Natl. Acad. Sci. USA 94:5320-25, 1997

Non-Patent Document 13: Larochelle, A. et al.; Nat. Med., 2, 1329-37, 1996

Non-Patent Document 14: Shah, A J et al.; Blood., 87, 3563-3570, 1996

Non-Patent Document 15: Dick, J E et al.; Stem Cells., 15, 199-2037 1997

Non-Patent Document 16: Suzuki, T et al.; Stem Cells., 24, 2456-2465, 2006

Non-Patent Document 17: McNiece et al., Blood.; 96, 3001-3007, 2000

Non-Patent Document 18: Kaushansky, K et al.; Ann NY Acad. Sci., 1044, 139-141, 2005

Non-Patent Document 19: Kawano, Y et al.; Exp Hematol., 34, 150-8, 2006

Non-Patent Document 20: Kawada, H et al.; Exp Hematol., 5, 904-15, 1999

Non-Patent Document 21: Chute, J P et al.; Proc Natl Acad Sci USA., 103, 11707-12, 2006

Non-Patent Document 22: Milhem, M et al.; Blood., 103, 4102-10, 2004

Non-Patent Document 23: Leung, A Y et al.; Exp Hematol., 33, 422-7, 2005

Non-Patent Document 24: Appelbaum, F R.; Cancer., 72, 3387-92, 1993

DISCLOSURE OF INVENTION

Technical Problem

An object of the present invention is to expand hematopoietic stem cells and/or hematopoietic progenitor cells ex vivo efficiently in a short term using a biologically safe and inexpensively obtainable compound. Another object of the present invention is to use an index more efficient than conventional ones in determining the expansion effect of such a compound on hematopoietic stem cells and/or hematopoietic progenitor cells. A still another object of the present invention is to provide an expansion agent for hematopoietic stem cells and/or hematopoietic progenitor cells useful for improvement in the efficiency of gene transfer into hematopoietic stem cells for gene therapy and useful for treatment of various hematopoietic disorders caused by dysfunctional hematopoietic stem cells and/or hematopoietic progenitor cells and muscle and nerve diseases caused by damaged tissues. A still another object of the present invention is to provide a pharmaceutical agent effective for diseases which can be prevented, cured or alleviated through in vivo expansion of hematopoietic stem cells and/or hematopoietic progenitor cells.

Solution to Problem

The present inventors conducted extensive search for compounds having activity to expand human hematopoietic stem cells and/or hematopoietic progenitor cells ex vivo. As a result, they found that the compounds represented by the following formula show excellent expansion activity on CD34$^+$ cells, CD34$^+$CD38$^-$ cells, HPP-CFU colony forming cells, and SRC, even in the absence of TPO and are highly useful as an expansion agent for cell populations rich in human hematopoietic stem cells and/or hematopoietic progenitor cells and accomplished the present invention.

Namely, the present invention relates:

(1) A compound represented by the formula (I):

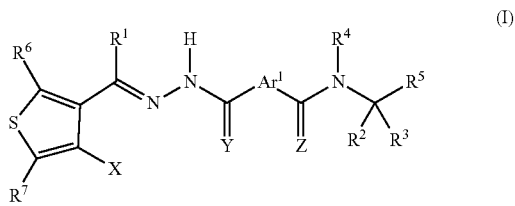

wherein each of $R^1$, $R^2$, $R^3$ and $R^4$ is independently a hydrogen atom or a $C_{1-10}$ alkyl group (the $C_{1-10}$ alkyl group may be optionally substituted with one or more halogen atoms), $R^5$ is a $C_{2-14}$ aryl group (the $C_{2-14}$ aryl group is substituted with —$V^1$ (wherein —$V^1$ is —$(CH_2)m_1M^1NR^8R^9$ (wherein $M^1$ is —(C=O)— or —(SO$_2$)—, $m_1$ is an integer of 0, 1 or 2, $R^8$ is a hydrogen atom or a $C_{1-3}$ alkyl group, and when $m_1$=0, $R^9$ is —$(CH_2)m_2OR^{10}$ (wherein $m_2$ is an integer of 1 or 2, and $R^{10}$ is a hydrogen atom, a $C_{1-3}$ alkyl group or —$(CH_2)m_3T$ (wherein $m_3$ is an integer of 1 or 2, and T is a hydroxyl group, a $C_{1-6}$ alkoxy group or a $C_{1-6}$ alkyl group)), —$(CH_2)m_4NR^{11}R^{12}$ (wherein $m_4$ is an integer of 1 or 2, and each of $R^{11}$ and $R^{12}$ is independently a hydrogen atom or —$(CH_2)m_5Q$ (wherein $m_5$ is an integer of 1 or 2, and Q is a hydroxy group, a $C_{1-3}$ alkoxy group, —$NR^{13}R^{14}$ (wherein each of $R^{13}$ and $R^{14}$ is independently a hydrogen atom or a $C_{1-3}$ alkyl group)), or $R^{11}$ and $R^{12}$ mean, together with each other as a substituent represented by the formula (II) or the formula (III) (wherein $R^{15}$ is a hydrogen atom, a $C_{1-3}$ alkyl group or an amino-protecting group)), and when $m_1$=1 or 2, $R^9$ is any of those mentioned above or a hydrogen atom)), —$V^2$ (wherein —$V^2$ is —$(CH_2)m_6NR^{16}R^{17}$ (wherein $m_6$ is an integer of 1 or 2, and each of $R^{16}$ and $R^{17}$ is independently a hydrogen atom, a $C_{1-3}$ alkylcarbonyl group or a $C_{1-3}$ alkylsulfonyl group)), —$V^3$ (wherein $V^3$ is $M^2NR^{18}(CH_2)m_7R^{19}$ (wherein $M^2$ is —(C=O)— or —(SO$_2$)—, $m_7$ is an integer of 1 or 2, $R^{18}$ is a hydrogen atom or a $C_{1-3}$ alkyl group, and $R^{19}$ is a $C_{2-9}$ heterocyclyl group or a $C_{2-14}$ aryl group)) or —$V^4$ (wherein $V^4$ is —(C=O)-(piperazine-1,4-diyl)-U (wherein U is the same as $R^9$ other than a hydrogen atom))),

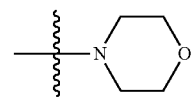

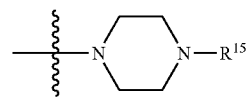

$R^6$ is a hydrogen atom or a $C_{1-10}$ alkyl group (the $C_{1-10}$ alkyl group may be optionally substituted with one or more halogen atoms), $R^7$ is a $C_{2-14}$ aryl group (the $C_{2-14}$ aryl group is substituted with one or more substituents independently represented by —$V^5$ (wherein $V^5$ is a hydrogen atom, a hydroxy group, a protected hydroxy group, an amino group, a protected amino group, a thiol group, a protected thiol group, a nitro group, a cyano group, a halogen atom, a carboxy group, a carbamoyl group, a sulfamoyl group, a sulfo group, a formyl group, a $C_{1-3}$ alkoxy group (the $C_{1-3}$ alkoxy group is optionally substituted with one or more halogen atoms), a $C_{1-10}$ alkyl group (the $C_{1-10}$ alkyl group may be optionally substituted with one or more halogen atoms), a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylsulfonyl group, a $C_{1-10}$ alkylaminosulfonyl group, a $C_{1-10}$ alkylaminocarbonyl group, a $C_{1-10}$ alkylsulfonylamino group or a $C_{1-10}$ thioalkyl group)), $Ar^1$ is a $C_{2-14}$ arylene group (the $C_{2-14}$ arylene group is substituted with one or more substituents independently represented by —$V^6$ (wherein $V^6$ is the same as $V^5$, and $V^5$ is the same as defined above)), X is $OR^{20}$ (wherein $R^{20}$ is a hydrogen atom, a $C_{1-10}$ alkyl group or a $C_{1-10}$ alkylcarbonyl group (the $C_{1-10}$ alkyl group and the $C_{1-10}$ alkylcarbonyl group are optionally substituted with one or more substituents independently represented by —$V^7$ ($V^7$ is the same as $V^5$, and $V^5$ is the same as defined above))), and each of Y and Z is independently an oxygen atom or a sulfur atom, a tautomer, prodrug or pharmaceutically acceptable salt of the compound or a solvate thereof.

(2) The compound according to (1), wherein $R^1$ is a hydrogen atom or a $C_{1-6}$ alkyl group (the $C_{1-6}$ alkyl group may be optionally substituted with one or more halogen atoms), $R^2$, $R^3$ and $R^4$ and $R^6$ are hydrogen atoms, $Ar^1$ is represented by the formula (IV):

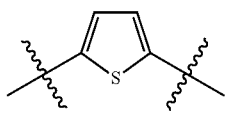

(IV)

$R^7$ is a phenyl group (the phenyl group is optionally substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), X is OH, Y and Z are oxygen atoms, a tautomer, prodrug or pharmaceutically acceptable salt of the compound or a solvate thereof.

(3) The compound according to (2), wherein $R^5$ is a phenyl group (the phenyl group is substituted with one or more substituents represented by any of the following formulae (V) to (XXII)):

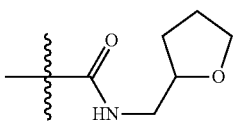

(V)

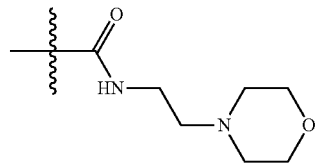

(VI)

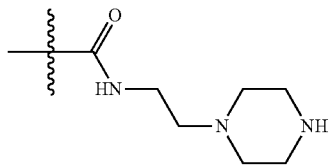

(VII)

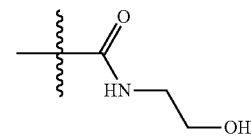

(VIII)

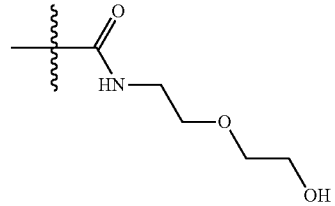

(IX)

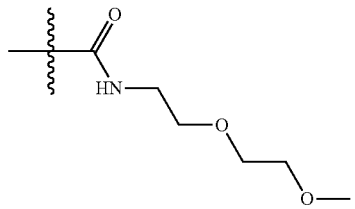

(X)

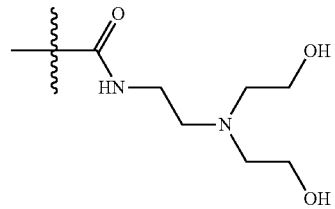

(XI)

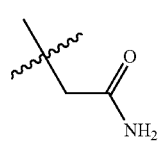

(XII)

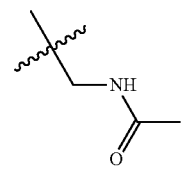

(XIII)

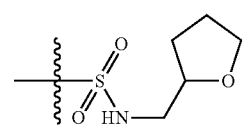

(XIV)

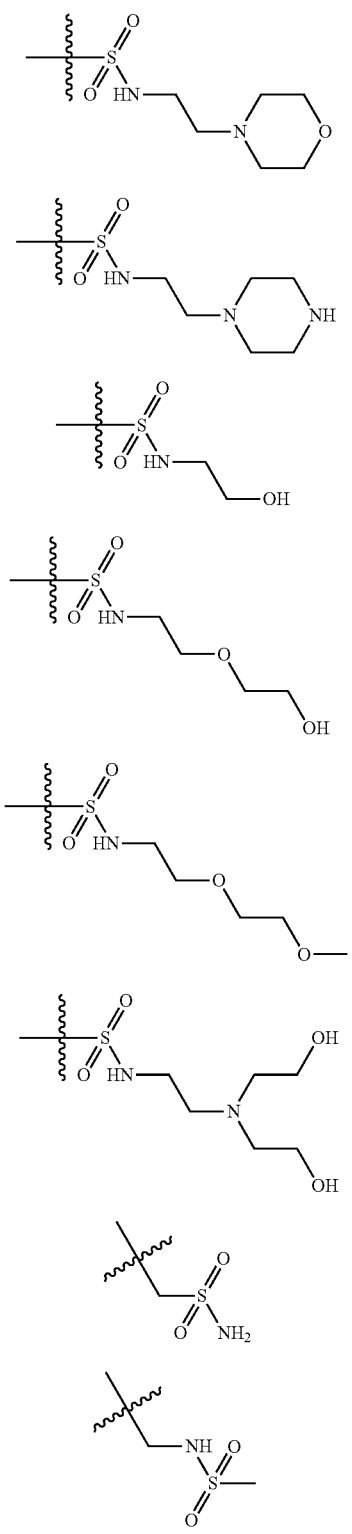

a tautomer, prodrug or pharmaceutically acceptable salt of the compound or a solvate thereof.

(4) The compound according to (3) wherein $R^7$ is a phenyl group (the phenyl group is substituted with one or more methyl groups, one or more t-butyl groups, one or more halogen atoms, one or more methoxy groups, one or more trifluoromethyl groups or one or more trifluoromethoxy groups), a tautomer, prodrug or pharmaceutically acceptable salt of the compound or a solvate thereof.

(5) The compound according to (4) wherein $R^1$ is a methyl group, a tautomer, prodrug or pharmaceutically acceptable salt of the compound or a solvate thereof.

(6) The compound according to (5) wherein $R^5$ is a phenyl group substituted with one or more substituents represented by the following formula (V), a tautomer, prodrug or pharmaceutically acceptable salt of the compound or a solvate thereof.

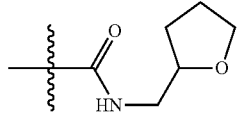

(V)

(7) The compound according to (5) wherein $R^5$ is a phenyl group substituted with one or more substituents represented by the following formula (VI), a tautomer, prodrug or pharmaceutically acceptable salt of the compound or a solvate thereof.

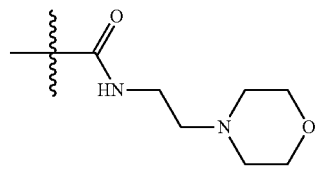

(VI)

(8) The compound according to (5) wherein $R^5$ is a phenyl group substituted with one or more substituents represented by the following formula (VII), a tautomer, prodrug or pharmaceutically acceptable salt of the compound or a solvate thereof.

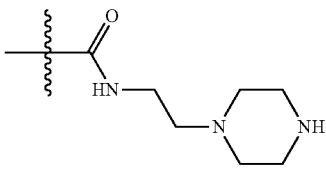

(VII)

(9) The compound according to (5) wherein $R^5$ is a phenyl group substituted with one or more substituents represented by the following formula (VIII), a tautomer, prodrug or pharmaceutically acceptable salt of the compound or a solvate thereof.

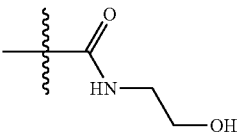

(VIII)

(10) The compound according to (5) wherein $R^5$ is a phenyl group substituted with one or more substituents represented by the following formula (IX), a tautomer, prodrug or pharmaceutically acceptable salt of the compound or a solvate thereof.

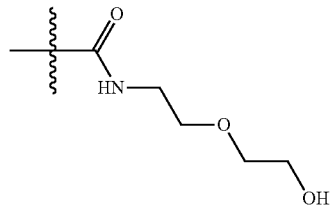
(IX)

(11) The compound according to (5) wherein $R^5$ is a phenyl group substituted with one or more substituents represented by the following formula (X), a tautomer, prodrug or pharmaceutically acceptable salt of the compound or a solvate thereof.

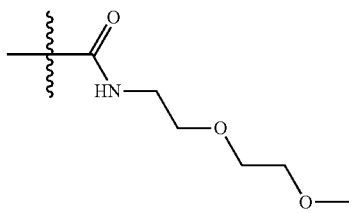
(X)

(12) The compound according to (5) wherein $R^5$ is a phenyl group substituted with one or more substituents represented by the following formula (XI), a tautomer, prodrug or pharmaceutically acceptable salt of the compound or a solvate thereof.

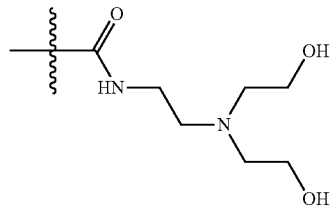
(XI)

(13) The compound according to (5) wherein $R^5$ is a phenyl group substituted with one or more substituents represented by the following formula (XII), a tautomer, prodrug or pharmaceutically acceptable salt of the compound or a solvate thereof.

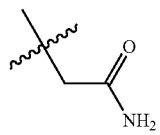
(XII)

(14) The compound according to (5) wherein $R^5$ is a phenyl group substituted with one or more substituents represented by the following formula (XIII), a tautomer, prodrug or pharmaceutically acceptable salt of the compound or a solvate thereof.

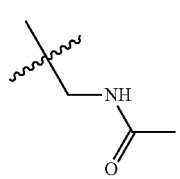
(XIII)

(15) The compound according to (5) wherein $R^5$ is a phenyl group substituted with one or more substituents represented by the following formula (XVIII), a tautomer, prodrug or pharmaceutically acceptable salt of the compound or a solvate thereof.

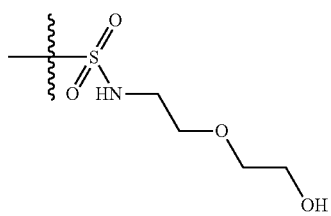
(XVIII)

(16) An expansion agent for hematopoietic stem cells and/or hematopoietic progenitor cells, which comprising the compound as defined in any one of (1) to (15), a tautomer or pharmaceutically acceptable salt of the compound or a solvate thereof, as an active ingredient.

(17) A method for expanding hematopoietic stem cells and/or hematopoietic progenitor cells, which comprises culturing hematopoietic stem cells and/or hematopoietic progenitor cells ex vivo in the presence of the compound as defined in any one of (1) to (15), a tautomer or pharmaceutically acceptable salt of the compound or a solvate thereof.

(18) The method for expanding hematopoietic stem cells and/or hematopoietic progenitor cells according to (17), wherein the hematopoietic stem cells and/or hematopoietic progenitor cells to be expanded are CD34$^+$ cells.

(19) The method for expanding hematopoietic stem cells and/or hematopoietic progenitor cells according to (17), wherein the hematopoietic stem cells and/or hematopoietic progenitor cells to be expanded are CD34$^+$CD38$^-$ cells.

(20) The method for expanding hematopoietic stem cells and/or hematopoietic progenitor cells according to (17), wherein the hematopoietic stem cells and/or hematopoietic progenitor cells to be expanded are HPP-CFU colony forming cells.

(21) The method for expanding hematopoietic stem cells and/or hematopoietic progenitor cells according to (17), wherein the hematopoietic stem cells and/or hematopoietic progenitor cells to be expanded are SRC.

(22) The method for expanding hematopoietic stem cells and/or hematopoietic progenitor cells according to any one of (17) to (21), which involves addition of at least one blood cell stimulating factor.

(23) The method for expanding hematopoietic stem cells and/or hematopoietic progenitor cells according to (22), wherein the blood cell stimulating factor is selected from the group consisting of stem cell factor (SCF), interleukin-3 (IL-3), interleukin-6 (IL-6), interleukin-11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

(24) The method for expanding hematopoietic stem cells and/or hematopoietic progenitor cells according to (23), wherein the blood cell stimulating factor is stem cell factor (SCF) and/or flk/flt3 ligand (FL).

(25) The method for expanding hematopoietic stem cells and/or hematopoietic progenitor cells according to any one of (17) to (24), wherein the hematopoietic stem cells and/or hematopoietic progenitor cells are obtained from the bone marrow, the liver, the spleen or peripheral or cord blood.

(26) The method for expanding hematopoietic stem cells and/or hematopoietic progenitor cells according to (25), wherein the hematopoietic stem cells and/or hematopoietic progenitor cells are obtained from cord blood.

(27) The method for expanding hematopoietic stem cells and/or hematopoietic progenitor cells according to (26), wherein hematopoietic stem cells and/or hematopoietic progenitor cells obtained from cord blood are cultured in the presence of stem cell factor (SCF) and/or flk/flt3 ligand (FL).

(28) A reagent or reagent kit for expanding hematopoietic stem cells and/or hematopoietic progenitor cells, which comprising the compound as defined in any one of (1) to (15), a tautomer or pharmaceutically acceptable salt of the compound or a solvate thereof, as an active ingredient.

(29) A method for producing transformed hematopoietic stem cells, which comprises transferring a gene into hematopoietic stem cells and/or hematopoietic progenitor cells while culturing the hematopoietic stem cells and/or hematopoietic progenitor cells ex vivo in the presence of the compound as defined in any one of (1) to (15), a tautomer or pharmaceutically acceptable salt of the compound or a solvate thereof, or expanding hematopoietic stem cells and/or hematopoietic progenitor cells carrying a gene transferred into them by culturing the hematopoietic stem cells and/or hematopoietic progenitor cells ex vivo in the presence of the compound as defined in any one of (1) to (15), a tautomer or pharmaceutically acceptable salt of the compound or a solvate thereof.

(30) The method for producing transformed hematopoietic stem cells according to (29), which involves addition of at least one blood cell stimulating factor.

(31) The method for producing transformed hematopoietic stem cells according to (30), wherein the blood cell stimulating factor is selected from the group consisting of stem cell factor (SCF), interleukin-3 (IL-3), interleukin-6 (IL-6), interleukin-11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

(32) The method for producing transformed hematopoietic stem cells according to any one of (29) to (31), wherein the hematopoietic stem cells and/or hematopoietic progenitor cells are obtained from the bone marrow, the liver, the spleen or peripheral or cord blood.

(33) Hematopoietic stem cells expanded by the method as defined in any one of (17) to (27).

(34) Transformed hematopoietic stem cells produced by the method as defined in any one of (29) to (32).

(35) A material for cell therapy by transplanting hematopoietic stem cells and/or hematopoietic progenitor cells expanded by the method as defined in any one of (17) to (27) into a human for treatment of a disease.

(36) A material for cell therapy by transplanting transformed hematopoietic stem cells produced by the method as defined in any one of (29) to (32) into a human for treatment of a disease.

(37) A pharmaceutical agent containing the compound as defined in any one of (1) to (15), a tautomer, prodrug or pharmaceutically acceptable salt of the compound or a solvate thereof, as an active ingredient.

(38) The material for cell therapy according to (35) or (36) or the pharmaceutical agent according to (37), wherein the disease to be treated is leukemia, aplastic anemia, myelodysplastic syndrome, malignant lymphoma, multiple myeloma, myeloproliferative disease, a genetic blood disease, a solid tumor, an autoimmune disease, immunodeficiency, diabetes mellitus, nerve injury, muscle injury, cerebral infarction, myocardial infarction or obstructive arteriosclerosis.

Advantageous Effect(s) of Invention

By using the compounds of the present invention, it is possible to expand hematopoietic stem cells and/or hematopoietic progenitor cells by culturing them ex vivo. Hematopoietic stem cells and/or hematopoietic progenitor cells produced by using the compound of the present invention can be used as a cell transplant for treatment of diseases. The compounds of the present invention also make it possible to provide a cell transplant (graft) soon as required even from a transplant source which can be obtained in a limited amount, by expanding hematopoietic stem cells and/or hematopoietic progenitor cells easily. Because the compounds of the present invention have an effect of expanding hematopoietic stem cells and/or hematopoietic progenitor cells, they are useful as pharmaceutical agents for use in vivo and can be used as preventing, therapeutic or alleviating agent for diseases against which in vivo expansion of hematopoietic stem cells and/or hematopoietic progenitor cells is effective.

The compounds to be used in the present invention can be produced by ordinary processes for organic synthesis and are obtained without using any substances derived from an animal other than human or a microorganism. Therefore, it is possible to prevent contamination with an unknown pathogen or a biomaterial from an animal other than human or a microorganism, as compared with expansion of hematopoietic stem cells using a protein such as cytokines and growth factors obtained by gene recombination technology. Namely, hematopoietic stem cells and/or hematopoietic progenitor cells obtained by the method of the present invention can avoid infection, contamination with foreign genes or immune response to foreign proteins. While being proteins, cytokines and growth factors can be stored or used within very narrow optimal ranges in terms of pH, heat and ion strength, the compounds of the present invention can be used and stored under relatively broad ranges of conditions. In addition, because the compounds of the present invention can be produced inexpensively and continuously unlike proteins, it is possible to eventually reduce treatment cost.

DESCRIPTION OF DRAWING(S)

[FIG. 1] A graph showing that $CD34^+CD38^-$ cells were expanded more remarkably in a culture of $CD34^+$ cells in the presence of a compound of the present invention than in the presence of TPO as a positive control.

Figure 2:
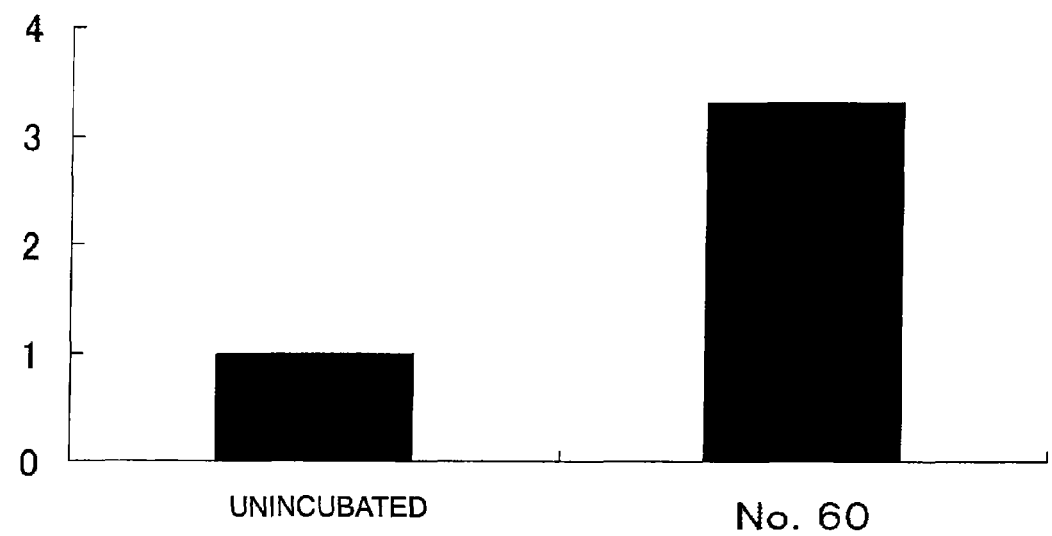

[FIG. 2] A graph showing that SRC were expanded more remarkably from $CD34^+$ cells cultured in the presence of a compound of the present invention than from uncultured $CD34^+$ cells, when assayed after transplantation of the cultured and uncultured $CD34^+$ cells into immunodeficient mice.

DESCRIPTION OF EMBODIMENT(S)

Now, the present invention will be described in further detail.

The terms used herein are defined as follows.

Hematopoietic stem cells are defined as cells having both pluripotency which allows them to differentiate into blood cells of all lineages and the ability to regenerate themselves while maintaining the pluripotency. Multipotential hematopoietic progenitor cells are cells which can differentiate into a plurality of blood cell lineages, though not into all blood cell lineages. Unipotential hematopoietic progenitor cells are cells which can differentiate into only one blood cell lineage. Hematopoietic progenitor cells are a group of cells which covers both multipotential and unipotential hematopoietic progenitor cells. For example, the hematopoietic progenitor cells in the present invention may be granulocyte-macrophage colony forming cells (CFU-GM), eosinophil colony forming cells (EO-CFC), erythroid burst forming cells (BFU-E) as erythroid progenitor cells, megakaryocyte colony forming cells (CFU-MEG) or myeloid stem cells (mixed colony forming cells, CFU-GEMM). Among them, cells forming multipotential colonies with diameters of at least 1 mm are called HPP-CFU colony forming cells and are defined as the least differentiated hematopoietic progenitor cells, along with mixed colony forming cells (CFU-GEMM) (McNiece, I. K., et al. 1989. Detection of a human CFC with a high proliferative potential. Blood. 74: 609-612.).

$CD34^+$ means expressing CD (cluster of differentiation) 34 antigen on the cell surface. This antigen is a marker for hematopoietic stem cells and/or hematopoietic progenitor cells and disappears as the cell differentiates. Populations of $CD34^+$ cells are enriched with hematopoietic stem cells and/or hematopoietic progenitor cells.

$CD38^-$ means not expressing CD38 antigen on the cell surface. The expression of this antigen increases as blood cells differentiate. $CD34^+CD38^-$ cells mean cells expressing CD34 antigen but not expressing CD38 antigen. $CD34^+CD38^-$ cells are characterized as a group of cells containing more hematopoietic stem cells than $CD34^+$ cells.

It has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells.

In the present invention, differentiation of hematopoietic stem cells and/or hematopoietic progenitor cells covers conversion of hematopoietic stem cells to hematopoietic progenitor cells, conversion of multipotential hematopoietic progenitor cells to unipotential hematopoietic progenitor cells and conversion of hematopoietic progenitor cells to cells having specific functions, i.e., mature blood cells such as erythrocytes, leukocytes and megakaryocytes.

In the present invention, expansion of hematopoietic stem cells means that the number of hematopoietic stem cells is greater after culturing than before culturing. Expansion of hematopoietic progenitor cells means that the number of hematopoietic stem progenitor cells is greater after culturing than before culturing.

Therefore, in the present invention, hematopoietic stem cell and/or hematopoietic progenitor cell expansion activity means the ability to proliferate hematopoietic stem cells and/or hematopoietic progenitor cells having the above-mentioned functions and increase hematopoietic stem cells and/or hematopoietic progenitor cells having the same functions. In the present invention, hematopoietic stem cell and/or hematopoietic progenitor cell differentiating activity means the ability to induce differentiation of hematopoietic stem cells and/or hematopoietic progenitor cells and to convert them into hematopoietic progenitor cells having the above-mentioned functions and/or mature blood cells (such as erythrocytes, leukocytes and megakaryocytes).

The compounds used in the present invention act on hematopoietic stem cells and/or hematopoietic progenitor cells and shows such an activity that they help hematopoietic stem cells and/or hematopoietic progenitor cells proliferate and survive. The compounds are capable of proliferate hematopoietic stem cells with minimal differentiation. In some cases of treatment by transplantation of hematopoietic stem cells such as peripheral stem cells and cord blood stem cells, hematopoietic stem cells and/or hematopoietic progenitor cells as the transplant cannot be obtained in sufficient numbers to carry out the transplantation. Use of the compounds makes it possible to expand collected hematopoietic stem cells and hematopoietic progenitor cells ex vivo and obtain hematopoietic stem cells and hematopoietic progenitor cells in the amount required to carry out the transplantation even in such cases. Specifically speaking, it is possible to expand hematopoietic stem cells with minimal differentiation by culturing them in a medium containing the compounds and use them for transplantation. It is also possible to expand hematopoietic stem cells more efficiently by further adding various cytokines or growth factors, by coculturing them with stromal cells, or by further adding other compounds which act on hematopoietic stem cells and/or hematopoietic progenitor cells.

In the method using the compounds of the present invention, the collected cells to be cultured for transplantation may be an isolated population of either hematopoietic stem cells or hematopoietic progenitor cells or a population containing both of them and may be, for example, $CD34^+$ cells, $CD34^+CD38^-$ cells, $CD90^+$ cells, $CD133^+$ cells. The cells may contain either hematopoietic stem cells or hematopoietic progenitor cells and further contain other mature blood cells.

The source of the hematopoietic stem cells and/or hematopoietic progenitor cells in the method using the compounds of the present invention may be any tissue as long as it contains hematopoietic stem cells, and it may be human bone marrow, peripheral blood, peripheral blood containing hematopoietic stem cells mobilized by a cytokine or the like, spleen, liver or cord blood.

The hematopoietic stem cells and/or hematopoietic progenitor cells can be cultured in a culture vessel generally used for animal cell culture such as a Petri dish, a flask, a plastic bag, a Teflon (registered trademark) bag, optionally after preliminary coating with an extracellular matrix or a cell adhesion molecule. The material for such a coating may be collagens I to XIX, fibronectin, vitronectin, laminins 1 to 12, nitogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The nutrient medium to be used for culturing hematopoietic stem cells and/or hematopoietic progenitor cells by using the compounds of the present invention may be a natural medium, a semi-synthetic medium or a synthetic medium in terms of composition, and may be a solid medium, a semi-solid medium or a liquid medium in terms of shape, and any nutrient medium used for animal cell culture, especially for hematopoietic stem cell and/or hematopoietic progenitor cell culture, may be used. As such a nutrient medium, Dulbecco's Modified Eagles's Medium (DMEM), Ham's Nutrient Mixture F12, McCoy's 5A medium, Eagles's Minimum Essential Medium (EMEM), αMEM medium (alpha Modified Eagles's Minimum Essential Medium), RPMI1640 medium, Iscove's Modified Dulbecco's Medium (IMDM), StemPro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich) or QBSF-60 (Quality Biological) may be mentioned.

Such a medium may contain sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The cytokines to be added to the medium may be interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO) and thrombopoietin (TPO), but are not restricted to those mentioned above. The growth factors to be added to the medium may be transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 2, 3, 5 or 7 (Angpt 2, 3, 5 or 7), insulin-like growth factor (IGF), insulin-like growth factor binding protein (IGFBP) and Pleiotrophin, but are not restricted to those mentioned above. Besides, recombinant cytokines or growth factors having an artificially modified amino acid sequence such as IL-6/soluble IL-6 receptor complex, and Hyper IL-6 (IL-6/soluble IL-6 receptor fusion protein) may also be added.

Among the above-mentioned cytokines and growth factors, preferred are stem cell factor (SCF), interleukin-3 (IL-3), interleukin-6 (IL-6), interleukin-11 (IL-11), flk2/flt3 ligand (FL), granulocyte colony stimulating factor (G-CSF), granulocyte-macrophage colony stimulating factor (GM-CSF), thrombopoietin (TPO), erythropoietin (EPO), Notch ligand (Delta 1), Pleiotrophin and the like, and more preferred are stem cell factor (SCF), flk2/flt3 ligand (FL), thrombopoietin (TPO) and the like. Cytokines and growth factors are usually added to culture at a concentration of 0.1 ng/mL to 1000 ng/mL, preferably from 1 ng/mL to 100 ng/mL.

In addition, at least one chemical substance known to be effective for expansion of hematopoietic stem cells may be added to the medium singly or in combination. Examples of such substances include copper chelators represented by tetraethylenepentamine, histone deacetylase inhibitors represented by trichostatin A, DNA methylase inhibitors represented by 5-aza-2'-deoxycytidine, retinoic acid receptor ligands represented by all-trans retinoic acid, aldehyde dehydrogenase inhibitors represented by dimethylaminobenzaldehyde, glycogen synthase kinase-3 inhibitors represented by 6-bromoindirubin-3'-oxime (6BIO) and prostaglandin E2, but they are not restricted to those mentioned above.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

When a compound of the present invention is added to such a medium as mentioned above, it is first dissolved in an appropriate solvent and added to the medium so that the concentration of the compound will be from 1 ng/mL to 100 μg/mL, preferably from 3 ng/mL to 30 μg/mL, more preferably from 30 ng/mL to 10 μg/mL, particularly preferably from 300 ng/mL to 3 μg/mL. Examples of the appropriate solvent include dimethyl sulfoxide (DMSO) and various alcohols, but it is not restricted thereto. The compounds of the present invention may be immobilized on the surface of the substrate or support used for the culture. The compounds of the present invention may be provided or stored in a certain form, for example, in a solid form as a tablet, a pill, a capsule or a granule, in a liquid form as a solution or suspension in an appropriate solvent or resolvent, or in the form bound to the substrate or support.

When they are formulated into such a form, additives such as a preservative like p-hydroxybenzoates, an excipient like lactose, glucose, sucrose and mannitol; a lubricant like magnesium stearate and talc; a binder like polyvinyl alcohol, hydroxypropylcellulose and gelatin, a surfactant like fatty acid esters, a plasticizer like glycerin may be added. The additives are not restricted to those mentioned above and a person skilled in the art can use any additives of choice.

The hematopoietic stem cells and/or hematopoietic progenitor cells are cultured usually at a temperature of from 25 to 39° C., preferably from 33 to 39° C., in the atmosphere having a $CO_2$ concentration of from 4 to 10 vol %, preferably from 4 to 6 vol %, usually for a period of from 3 to 35 days, preferably from 5 to 21 days, more preferably from 7 to 14 days.

When the hematopoietic stem cells and/or hematopoietic progenitor cells are cocultured with stromal cells by using a compound of the present invention, collected bone marrow cells may be grown directly in culture. Alternatively, it is possible to separate collected bone marrow into stromal cells, hematopoietic stem cells and/or hematopoietic progenitor cells, and coculture the hematopoietic stem cells and/or hematopoietic progenitor cells with stromal cells from an individual other than the bone marrow donor. It is also possible to first grow stromal cells only and add and grow hematopoietic stem cells and/or hematopoietic progenitor cells in coculture. When these cells are cocultured, it is possible to use such media and culture conditions as mentioned above.

Hematopoietic stem cells and/or hematopoietic progenitor cells expanded by using the compounds of the present invention can be used as a cell transplant. Because hematopoietic stem cells can differentiate into blood cells of all lineages, they may be transplanted after differentiated into a certain type of blood cells ex vivo. Hematopoietic stem cells and/or hematopoietic progenitor cells expanded by using the compounds of the present invention may be transplanted as they are, or after enrichment using a cell surface antigen as an index, for example, by a magnetic bead method or by a cell sorting method. Such a cell surface antigen molecule may be CD2, CD3, CD4, CD8, CD13, CD14, CD15, CD16, CD19, CD24, CD33, CD34, CD38, CD41, CD45, CD56, CD66, CD90, CD133 or glycophorin A, but is not restricted thereto. The expanded hematopoietic stem cells and/or hematopoietic progenitor cells may be transplanted to its donor or another individual.

Namely, hematopoietic stem cells and/or hematopoietic progenitor cells expanded by using the compounds of the present invention can be used as a transplant for hematopoietic stem cell therapy as a substitute for conventional bone marrow or cord blood transplantation. The transplantation of hematopoietic stem cells and hematopoietic progenitor cells expanded by using the compounds of the present invention is carried out in the same manner as conventional bone marrow or cord blood transplantation, except for the cells to be used. Hematopoietic stem cells and/or hematopoietic progenitor cells expanded by using a compound of the present invention can also be used as a transplant to promote regeneration of nerves and muscles damaged by a traumatic injury or a vascular disorder. The transplant may be a composition containing a buffer solution, an antibiotic, a pharmaceutical in addition to hematopoietic stem cells and/or hematopoietic progenitor cells expanded by the method of the present invention.

The hematopoietic stem cell and/or hematopoietic progenitor cell transplant obtained by expansion using the compounds of the present invention is useful for treatment of not only various types of leukemia but also various diseases. For example, in a case of treatment of a solid cancer patient by chemotherapy or radiotherapy which may cause myelosuppression as a side effect, the patient can recover from hematopoietic damage quickly if the hematopoietic stem cells and/or hematopoietic progenitor cells collected from the bone marrow or peripheral blood of the patient preliminarily to the treatment are expanded ex vivo and returned to the patient after the treatment. Thus, a more intense chemotherapy becomes available with an improved therapeutic effect. It is also possible to alleviate a deficiency in a certain type of blood cells in a patient by differentiating hematopoietic stem cells and/or hematopoietic progenitor cells obtained by using the compounds of the present invention into such a type of blood cells and returning them into the patient. A transplant obtained by using the compounds of the present invention is effective against diseases accompanying decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity, immune dysfunction, diseases accompanying nerve damage, diseases accompanying muscle damage and ischemic diseases.

As specific examples, chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, malignant lymphoma, Hodgkin's disease, multiple myeloma, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, traumatic spinal cord injury, nerve injury, neurotmesis, skeletal muscle injury, scarring, diabetes mellitus, cerebral infarction, myocardial infarction, obstructive arteriosclerosis and the like may be mentioned.

Hematopoietic stem cells and/or hematopoietic progenitor cells expanded by using the compounds of the present invention can be used for gene therapy. Gene therapy using hematopoietic stem cells has been difficult because the transfer of a target gene into hematopoietic stem cells at the stationary phase is inefficient, and hematopoietic stem cells differentiate in culture during a gene transfer procedure. However, use of the compounds of the present invention in culture makes it possible to expand hematopoietic stem cells while suppressing differentiation of hematopoietic stem cells and improve the gene transfer efficiency considerably. In the gene therapy, a therapeutic gene is transfected into hematopoietic stem cells and/or hematopoietic progenitor cells using the compounds of the present invention, and the resulting transfected cells are transplanted into patients. The therapeutic gene to be transfected is appropriately selected among genes for hormones, cytokines, receptors, enzymes, polypeptides and the like according to the disease (Advance in Pharmacology 40, Academic Press, 1997). Specific examples of the gene include genes for insulin, amylase, proteases, lipases, trypsinogen, chymotrypsinogen, carboxypeptidases, ribonucleases, deoxyribonucleases, phospholipase A2, esterases, α1-antitrypsin, blood coagulation factors (VII, VIII, IX and the like), protein C, protein S, antithrombin, UDP glucuronyl transferase, ornithine transcarbanoylase, hemoglobin, NADPH oxidase, glucocerebrosidase, α-galactosidase, α-glucosidase, α-iduronidase, chytochrome P450 enzymes, adenosine deaminase, Bruton's kinase, complements C1 to C4, JAK3, common cytokine receptor γ chain, Ataxia Telangiectasia Mutated (ATM), Cystic Fibrosis (CF), myocilin, thymic humoral factor, thymopoietin, gastrin, selectins, cholecystokinin, serotinin, substance P, Major Histocompatibility Complex (MHC), multiple drug resistance factor (MDR-1) and the like.

In addition, RNA genes suppressing expression of disease genes are effective as therapeutic genes and can be used in the method of the present invention. For example, antisense RNA, siRNA, shRNA decoy RNA, ribozymes and the like may be mentioned.

For transfer of a therapeutic gene into hematopoietic stem cells and/or hematopoietic progenitor cells, ordinary gene transfer methods for animal cells, such as those using vectors for animal cells such as retrovirus vectors like murine stem cell vector (MSCV) and Moloney murine leukemia virus (MmoLV), adenovirus vectors, adeno-associated virus (AAV) vectors, herpes simplex virus vectors and lentivirus vectors (for vectors for gene therapy, see Verma, I. M., Nature, 389:239, 1997), calcium phosphate coprecipitation, DEAE-dextran transfection, electroporation, a liposome method, lipofection, microinjection or the like may be used. Among them, retrovirus vectors, adeno-associated virus vectors or lentivirus vectors are preferred because their integration into the chromosomal DNA is expected to allow eternal expression of the gene.

For example, an adeno-associated virus (AAV) vector is prepared as follows. First, 293 cells are transfected with a vector plasmid obtained by inserting a therapeutic gene between the ITRs (inverted terminal repeats) at both ends of wild-type adeno-associated virus DNA and a helper plasmid for supplementing virus proteins and subsequently infected with an adenovirus as a helper virus to induce production of virus particles containing AAV vectors. Instead of the adenovirus, a plasmid for expression of an adenovirus gene which functions as a helper may be transfected. Next, hematopoietic stem cells and/or hematopoietic progenitor cells are infected with the virus particles. It is preferred to insert an appropriate promoter, enhancer, insulator or the like upstream of the target gene in the vector DNA to regulate expression of the gene. Introduction of a marker gene such as a drug resistance gene in addition to the therapeutic gene makes it easy to select cells carrying the therapeutic gene. The therapeutic gene may be a sense gene or an antisense gene.

When hematopoietic stem cells and/or hematopoietic progenitor cells are transfected with a therapeutic gene, the cells are cultured by an appropriate method selected from the culture methods mentioned above for expansion of hematopoietic stem cells and/or hematopoietic progenitor cells by the person in charge. The gene transfer efficiency can be evaluated by a standard method in the art.

The transplant for gene therapy may be a composition containing a buffer solution, an antibiotic, a pharmaceutical and the like in addition to hematopoietic stem cells and/or hematopoietic progenitor cells expanded by the method of the present invention.

The diseases to be treated by gene therapy targeting blood cells include chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), hepatitis B, hepatitis C, congenital anemia such as thalassemia, hemolytic anemia due to enzyme deficiency, Fanconi's anemia and sicklemia, lysosomal storage disease such as Gaucher's disease and mucopolysaccharidosis, adrenoleukodystrophy, various kinds of cancers and tumors.

The compounds of the present invention can be used in pharmaceutical agents for preventing, treating or alleviating diseases against which in vivo expansion of hematopoietic stem cells and/or hematopoietic progenitor cells is effective. Pharmaceutical agents containing the compounds of the present invention as an active ingredient may usually be administered as oral medicines such as tablets, capsules, powder, granules, pills and syrup, as rectal medicines, percutaneous medicines or injections. The pharmaceutical agents may be administered as a single therapeutic agent or as a mixture with other therapeutic agents. Though they may be administered as they are, they are usually administered in the form of medical compositions. As other therapeutic agents, active substances selected from the group consisting of colony stimulating factors, cytokines, chemokines, interleukins, cytokine receptor agonists or antagonists, soluble receptors, anti-receptor agonists or antagonist antibodies, small molecules or peptides functioning by the same mechanisms as at least one of those mentioned above may be mixed in a therapeutically effective amount. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents containing the compounds of the present invention for administration to human is usually about from 0.1 to 1000 mg/human/day in the case of oral drugs or rectal administration and about from 0.05 mg to 500 mg/human/day in the case of injections into an adult, though it depends on the age and conditions of the patient. The above-mentioned ranges are mere examples, and the dose should be determined from the conditions of the patient.

The present invention is used when the use of compounds which has activity to expand hematopoietic stem cells and/or hematopoietic progenitor cells are expected to alleviate pathological conditions. The diseases as the targets of pharmaceutical agents containing the compounds of the present invention include diseases accompanying decrease in hematopoietic stem cells, degenerative diseases and injuries. Specifically, congenital anemia, autoimmune anemia, decrease in hematopoietic stem cells and/or hematopoietic progenitor cells accompanying various kinds of cancers and tumors, decrease in hematopoietic stem cells and/or hematopoietic progenitor cells accompanying chemotherapy or radiotherapy of cancers, acute radiation syndrome, delayed repopulation of hematopoietic stem cells and/or hematopoietic progenitor cells after bone marrow, cord blood or peripheral blood transplantation, decrease in hematopoietic stem cells and/or hematopoietic progenitor cells accompanying blood transfusion, transverse myelitis, multiple sclerosis, demyelination accompanying brain or spinal cord injury, acute brain damage, head injury, spinal cord injury, peripheral nerve injury, ischemic brain injury, hereditary CNS demyelinating disorders, epilepsy, perinatal asphyxia, asphyxia, anoxia, status epilepticus, cerebral stroke, Alzheimer's disease, Parkinson's disease, Huntington's chorea, baldness, amyotrophic lateral sclerosis, cardiovascular diseases, myocardial infarction, cardiac and vascular diseases, liver diseases, gasterointestinal diseases, slight injury, age-related cell injury, age-related tissue injury, lupus, diabetes mellitus, osteoporosis, glucocorticoid-induced osteoporosis, Paget's disease, bone hypermetabolism, periodontal disease, tooth loss, bone fractures, arthritis, articular rheumatism, osteoarthritis, periprosthetic osteolysis, dysostosis, metastatic bone diseases, macular degeneration, dry eye syndrome, cataract, diabetic retinopathy, glaucoma, vitreous diseases, retinal degeneration and the like may be mentioned.

Preferred embodiments of the method of expansion and transfection of hematopoietic stem cells and/or hematopoietic progenitor cells and the method of transplantation of the expanded or transfected hematopoietic stem cells and/or hematopoietic progenitor cells by using the compounds of the present invention will be described below.

First, for expansion of hematopoietic stem cells and/or hematopoietic progenitor cells, cord blood, bone marrow, peripheral blood or the like is collected, and a cell population enriched with hematopoietic stem cells and/or hematopoietic progenitor cells is separated from it. As such a cell population, $CD34^+$ cells, $CD34^+CD38^-$ cells, $CD90^+$ cells, $CD133^+$ cells may be mentioned. For example, $CD34^+$ cells can be separated by density centrifugation combined with magnetic cell sorting (MACS) or flow cytometry. For example, CPD (citrate-phosphate-dextran)-treated blood is fractioned by density centrifugation to separate and collect a mononuclear cell enriched fraction (hereinafter referred to as nucleated cell fraction). As density centrifugation, dextran or Ficoll density centrifugation, Ficoll-paque density gradient centrifugation, Percoll discontinuous density gradient centrifugation or Lymphoprep density gradient centrifugation may be mentioned. Then, magnetic beads coated with an anti-human CD34 monoclonal antibody (Miltenyi Biotec; hereinafter referred to CD34 antibody magnetic beads) and the collected nucleated cell fraction are mixed and incubated at from 2 to 8° C. (for about 30 minutes) to bind $CD34^+$ cells in the nucleated cell fraction to the antibody magnetic beads. The antibody magnetic bead/$CD34^+$ cell complexes are separated and collected by a specialized magnetic cell separator such as autoMACS system (Miltenyi Biotec). The $CD34^+$ cells thus obtained are cultured using a compound of the present invention. The conditions, incubator and medium for culturing $CD34^+$ cells, the species and amount of the compound, the kinds and amounts of additives and the incubation time and temperature may be selected appropriately from those disclosed herein by the person in charge, but are not restricted thereto. $CD34^+$ cells are transfected with a gene which is obtained by cloning a target gene into a vector by a standard method in the art, and incubating the vector and $CD34^+$ cells in the presence of the compound of the present invention. The kinds of the target gene and the vector, the transfection method and the culture method may be selected appropriately from those disclosed herein by the person in charge, but are not restricted thereto.

After culturing, the total cell count is measured by trypan blue assay or the like, while the cell culture is stained with an anti CD34 antibody and an anti CD38 antibody labeled with a fluorescent dye such as FITC (fluorescein isothiocyanate), PE (phycoerythrin) or APC (allophycocyanin), and the proportion of $CD34^+CD38^-$ cells is analyzed by flow cytometry. Thus, it is possible to determine how much hematopoietic stem cells and hematopoietic progenitor cells are expanded in the cell culture. The proportion of the least differentiated cells can be determined by subjecting part of the cell culture to colony assay and counting the resulting HPP-CFC colonies. The transgene can be detected by analyzing DNA or RNA extracted from the cells by southern blotting, northern blotting, RT-PCR (Reverse Transcriptase Polymerase Chain Reaction) or the like. The efficiency of transfer of the target gene is determined by detecting the protein expressed by the transgene by ELISA (Enzyme Linked ImmunoSorvent Assay) or flow cytometry using a specific antibody or by measuring the functional activity of the protein by an enzyme assay.

Expanded or transfected hematopoietic stem cells and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. In the case of treatment of myocardial infarction or nerve or muscle injury, cells may be transplanted by injection to diseased, injured or suture sites or into the spinal cavity, or by local injection after loaded onto a non-antigenic support such as atelocollagen gel. When cells are transplanted, the disease to be treated, the pretreatment and the cell transplantation method are selected appropriately by the person in charge. The engraftment of transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carryout transplantation therapy and gene therapy safely and easily in a short term by using the expanded cells.

Because hematopoietic stem cells and/or hematopoietic progenitor cells can be expanded efficiently by using the compounds of the present invention, the compounds of the present invention can be used as a reagent for research on hematopoietic stem cells and/or hematopoietic progenitor cells. For example, in a study to elucidate the factor regulating differentiation and growth of hematopoietic stem cells by identifying the colony forming cells in a culture of hematopoietic stem cells and analyzing the change in cell surface differentiation markers and gene expression, when hematopoietic stem cells are cultured in the presence of a putative factor, addition of a compound of the present invention makes it possible to expand the hematopoietic stem cells and/or hematopoietic progenitor cells to be analyzed efficiently. The incubation conditions, the incubator and the culture medium, the species and amount of the compound of the present invention, the kinds and amounts of additives and the incubation time and temperature used to elucidate such a factor may be selected appropriately from those disclosed herein by the person in charge. The colony forming cells emerging in the culture can be observed under a microscope normally used in the art, optionally after staining them using an antibody specific for the colony forming cells. The change in gene expression caused by such a putative factor can be detected by analyzing DNA or RNA extracted from the cells by southern blotting, northern blotting, RT-PCR or the like. The cell surface differentiation markers can be detected by ELISA or flow cytometry using a specific antibody to examine the effect of the putative factor on differentiation and growth of the cells.

Now, the compounds to be used in the present invention will be described in terms of the definitions of terms used for it and its best mode.

In the compounds to be used in the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py"

denotes pyridyl, "Naphthyl" denotes naphthyl, "Me" denotes methyl, "Et" denotes ethyl, "Pr" denotes propyl, and "Bu" denotes butyl.

First, the terms in the respective substituents $R^1$ to $R^{20}$ and $V^1$ to $V^7$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and as specific examples, in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and as specific examples, in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and as specific examples, ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-14}$ aryl group may be a $C_{6-14}$ aryl group containing no hetero atoms as ring constituting atoms, a $C_{2-9}$ aromatic heterocyclic group or a $C_{2-14}$ fused polycyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

As a 5 to 7-membered $C_{2-6}$ heteromonocyclic group, a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 1-1,2,4-triazole group, a 3-1,2,4-triazole group, a 5-1,2,4-triazole group, a 1-1,2,3-triazole group, a 4-1,2,3-triazole group, a 5-1,2,3-triazole group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3, 4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like may be mentioned.

As a 8 to 10-membered $C_{5-9}$ fused heterocyclic group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like may be mentioned.

A $C_{2-14}$ fused polycyclic group is a fused bicyclic or fused tricyclic group consisting of a $C_{6-14}$ aryl group containing no hetero atoms and at most 12 carbon atoms as mentioned above or a $C_{2-9}$ aromatic heterocyclic group fused with a $C_{2-9}$ heterocyclyl group, and:

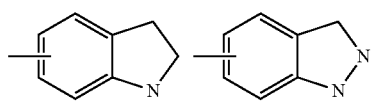

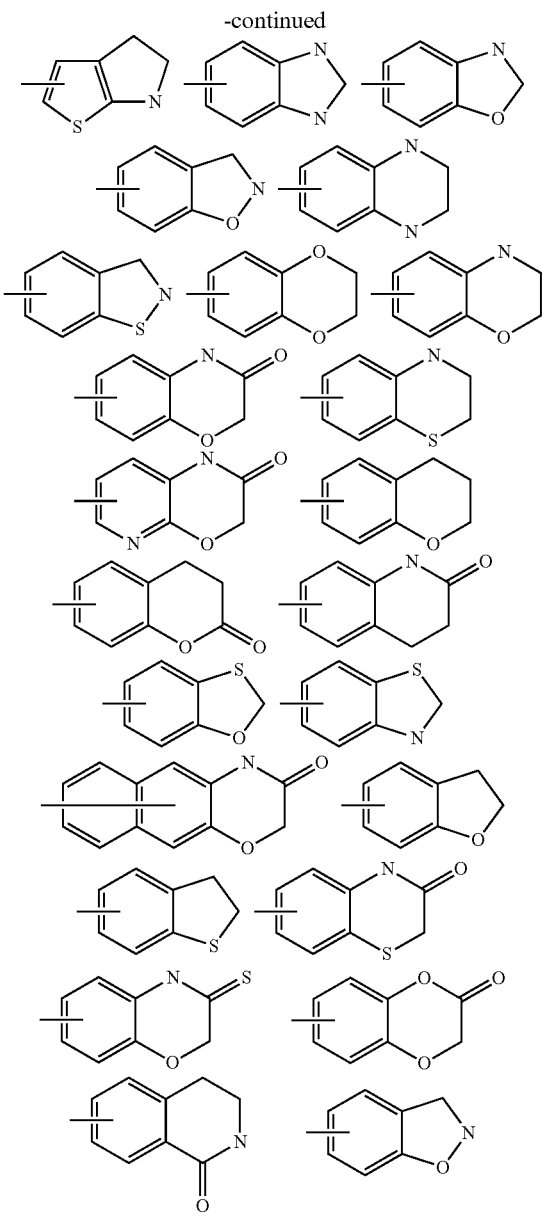

may be mentioned specifically.

An N-oxide of an nitrogen-containing $C_{2-14}$ aryl group is a group obtained by oxidizing a nitrogen atom in the $C_{2-14}$ aryl group with oxygen, and specifically, a 1-pyrrole-N-oxide group, a 2-pyrrole-N-oxide group, 3-pyrrole-N-oxide, a 1-imidazole-N-oxide group, a 2-imidazole-N-oxide group, a 4-imidazole-N-oxide group, a 1-pyrazole-N-oxide group, a 3-pyrazole-N-oxide group, a 4-pyrazole-N-oxide group, a 2-thiazole-N-oxide group, a 4-thiazole-N-oxide group, a 5-thiazole-N-oxide group, a 3-isothiazole-N-oxide group, a 4-isothiazole-N-oxide group, a 5-isothiazole-N-oxide group, a 2-oxazole-N-oxide group, a 4-oxazole-N-oxide group, a 5-oxazole-N-oxide group, a 3-isoxazole-N-oxide group, a 4-isoxazole-N-oxide group, a 5-isooxazole-N-oxide group, a 2-pyridine-N-oxide group, a 3-pyridine-N-oxide group, a 4-pyridine-N-oxide group or the like may be mentioned.

A $C_{1-10}$ thioalkyl group may linear, branched or a $C_{3-10}$ cyclothioalkyl group, and as specific examples, methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-3}$ alkylsulfonyl group may be linear, branched or a $C_3$ cycloalkylsulfonyl group, and as specific examples, methylsulfonyl, ethylsulfonyl, n-propylsulfonyl, i-propylsulfonyl, c-propylsulfonyl or the like may be mentioned.

A $C_{1-10}$ alkylsulfonyl group may be linear, branched or a $C_{3-10}$ cycloalkylsulfonyl group, and as specific examples, in addition to those mentioned above, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl or the like may be mentioned.

A $C_{1-10}$ alkylsulfonylamino group may be linear, branched or a $C_{3-10}$ cycloalkylsulfonylamino group, and as specific examples, methylsulfonylamino, ethylsulfonylamino, n-propylsulfonylamino, i-propylsulfonylamino, c-propylsulfonylamino, n-butylsulfonylamino, i-butylsulfonylamino, s-butylsulfonylamino, t-butylsulfonylamino, c-butylsulfonylamino, 1-methyl-c-propylsulfonylamino, 2-methyl-c-propylsulfonylamino, n-pentylsulfonylamino, 1-methyl-n-butylsulfonylamino, 2-methyl-n-butylsulfonylamino, 3-methyl-n-butylsulfonylamino, 1,1-dimethyl-n-propylsulfonylamino, 1,2-dimethyl-n-propylsulfonylamino, 2,2-dimethyl-n-propylsulfonylamino, 1-ethyl-n-propylsulfonylamino, c-pentylsulfonylamino, 1-methyl-c-butylsulfonylamino, 2-methyl-c-butylsulfonylamino, 3-methyl-c-butylsulfonylamino, 1,2-dimethyl-c-propylsulfonylamino, 2,3-dimethyl-c-propylsulfonylamino, 1-ethyl-c-propylsulfonylamino, 2-ethyl-c-propylsulfonylamino, n-hexylsulfonylamino, 1-methyl-n-pentylsulfonylamino, 2-methyl-n-pentylsulfonylamino, 3-methyl-n-pentylsulfonylamino, 4-methyl-n-pentylsulfonylamino, 1,1-dimethyl-n-butylsulfonylamino, 1,2-dimethyl-n-butylsulfonylamino, 1,3-dimethyl-n-butylsulfonylamino, 2,2-dimethyl-n-butylsulfonylamino, 2,3-dimethyl-n-butylsulfonylamino, 3,3-dimethyl-n-butylsulfonylamino, 1-ethyl-n-butylsulfonylamino, 2-ethyl-n-butylsulfonylamino, 1,1,2-trimethyl-n-propylsulfonylamino, 1,2,2-trimethyl-n-propylsulfonylamino, 1-ethyl-1-methyl-n-propylsulfonylamino, 1-ethyl-2-methyl-n-propylsulfonylamino, c-hexylsulfonylamino, 1-methyl-c-pentylsulfonylamino, 2-methyl-c-pentylsulfonylamino, 3-methyl-c-pentylsulfonylamino, 1-ethyl-c-butylsulfonylamino, 2-ethyl-c-butylsulfonylamino, 3-ethyl-c-butylsulfonylamino, 1,2-dimethyl-c-butylsulfonylamino, 1,3-dimethyl-c-butylsulfonylamino, 2,2-dimethyl-c-butylsulfonylamino, 2,3-dimethyl-c-butylsulfonylamino, 2,4-dimethyl-c-butylsulfonylamino, 3,3-dimethyl-c-butylsulfonylamino, 1-n-propyl-c-propylsulfonylamino, 2-n-propyl-c-propylsulfonylamino, 1-i-propyl-c-propylsulfonylamino, 2-i-propyl-c-propylsulfonylamino, 1,2,2-trimethyl-c-propylsulfonylamino, 1,2,3-trimethyl-c-propylsulfonylamino, 2,2,3-trimethyl-c-propylsulfonylamino, 1-ethyl-2-methyl-c-propylsulfonylamino, 2-ethyl-1-methyl-c-propylsulfonylamino, 2-ethyl-2-methyl-c-propylsulfonylamino, 2-ethyl-3-methyl-c-propylsulfonylamino, 1-methyl-1-ethyl-n-pentylsulfonylamino, 1-heptylsulfonylamino, 2-heptylsulfonylamino, 1-ethyl-1,2-dimethyl-n-propylsulfonylamino, 1-ethyl-2,2-dimethyl-n-propylsulfonylamino, 1-octylsulfonylamino, 3-octylsulfonylamino, 4-methyl-3-n- heptylsulfonylamino, 6-methyl-2-n-heptylsulfonylamino, 2-propyl-1-n-heptylsulfonylamino, 2,4,4-trimethyl-1-n-pentylsulfonylamino, 1-nonylsulfonylamino, 2-nonylsulfonylamino, 2,6-dimethyl-4-n-heptylsulfonylamino, 3-ethyl-2,2-dimethyl-3-n-pentylsulfonylamino, 3,5,5-trimethyl-1-n-hexylsulfonylamino, 1-decylsulfonylamino, 2-decylsulfonylamino, 4-decylsulfonylamino, 3,7-dimethyl-1-n-octylsulfonylamino, 3,7-dimethyl-3-n-octylsulfonylamino, c-heptylsulfonylamino, c-octylsulfonylamino, 1-methyl-c-hexylsulfonylamino, 2-methyl-c-hexylsulfonylamino, 3-methyl-c-hexylsulfonylamino, 1,2-dimethyl-c-hexylsulfonylamino, 1-ethyl-c-hexylsulfonylamino, 1-methyl-c-pentylsulfonylamino, 2-methyl-c-pentylsulfonylamino, 3-methyl-c-pentylsulfonylamino or the like may be mentioned.

A $C_{1-3}$ alkoxy group may be linear, branched or a $C_3$ cycloalkoxy group, and as specific examples, methoxy, ethoxy, n-propoxy, i-propoxy, c-propoxy or the like may be mentioned.

A $C_{1-6}$ alkoxy group may be linear, branched or a $C_{3-6}$ cycloalkoxy group, and as specific examples, in addition to those mentioned above, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-10}$ alkoxy group may be linear, branched or a $C_{3-10}$ cycloalkoxy group, and as specific examples, in addition to those mentioned above, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ alkoxycarbonyl group may be linear, branched or a $C_{3-10}$ cycloalkoxycarbonyl group, and as specific examples, methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-3}$ alkylcarbonyl group may linear, branched or a $C_3$ cycloalkylcarbonyl group, and as specific examples, methylcarbonyl, ethylcarbonyl, n-propylcarbonyl, i-propylcarbonyl, c-propylcarbonyl or the like may be mentioned.

A $C_{1-10}$ alkylcarbonyl group may linear, branched or a $C_{3-10}$ cycloalkylcarbonyl group, and as specific examples, in addition to those mentioned above, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-1-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-10}$ alkylcarbonyloxy group may be linear, branched or a $C_{3-10}$ cycloalkylcarbonyloxy group, and as specific examples, methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonylxoy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and as specific examples, methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propyl-carbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and specific examples, methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A di-$C_{1-10}$ alkylamino group may be symmetric or asymmetric. A symmetric di-$C_{1-10}$ alkylamino group may be linear, branched or a $C_{3-10}$ cycloalkylamino group, and as specific examples, dimethylamino, diethylamino, di-n-propylamino, di-1-propylamino, di-c-propylamino, di-n-butylamino, di-1-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, d i-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl) amino or the like may be mentioned.

An asymmetric di-$C_{1-10}$ alkylamino group may be linear, branched or a $C_{3-10}$ cycloalkylamino group, and as specific examples, (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, 1-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl) amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl) amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl) amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl) amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl) amino, (c-pentyl, c-hexyl)amino, (n-hexyl, c-hexyl)amino, (methyl, n-heptyl)amino, (methyl, n-octyl)amino, (methyl, n-nonanyl)amino, (methyl, n-decyl)amino, (ethyl, n-heptyl) amino, (ethyl, n-octyl)amino, (ethyl, n-nonanyl)amino, (ethyl, n-decyl)amino or the like may be mentioned.

A $C_{1-10}$ alkylaminocarbonyl group may be linear, branched or a $C_{1-10}$ cycloalkylaminocarbonyl group and may be a di-$C_{1-10}$ alkylaminocarbonyl group, and as specific examples, methylaminocarbonyl, ethylaminocarbonyl, n-propylaminocarbonyl, propylaminocarbonyl, c-propylaminocarbonyl, n-butylaminocarbonyl, butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7-dimethyl-1-n-octylaminocarbonyl, 3,7-dimethyl-3-n-octylaminocarbonyl or the like may be mentioned.

A di-$C_{1-10}$ alkylaminocarbonyl group may be symmetric or asymmetric. A symmetric di-$C_{1-10}$ alkylaminocarbonyl group may be linear, branched or a $C_{3-10}$ cycloalkylaminocarbonyl group, and as specific examples, dimethylaminocarbonyl, diethylaminocarbonyl, di-n-propylaminocarbonyl, di-1-propylaminocarbonyl, di-c-propylaminocarbonyl, di-n-butylaminocarbonyl, di-1-butylaminocarbonyl, di-s-butylaminocarbonyl, di-t-butylaminocarbonyl, di-c-butylaminocarbonyl, di-(1-methyl-c-propyl)aminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propyl)aminocarbonyl, di-(1,2-dimethyl-n-propyl)aminocarbonyl, di-(2,2-dimethyl-n-propyl)aminocarbonyl, di-(1-ethyl-n-propyl)aminocarbonyl, di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propyl)aminocarbonyl, di-(2-ethyl-c-propyl)aminocarbonyl, di-n-hexylaminocarbonyl, di-(1-methyl-n-pentyl)aminocarbonyl, di-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl, di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonyl)aminocarbonyl, di-(2,6-dimethyl-4-n-heptyl)aminocarbonyl, di-(3-ethyl-2,2-dimethyl-3-n-pentyl)aminocarbonyl, di-(3,5,5-trimethyl-1-n-hexyl)aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

An asymmetric $C_{1-10}$ dialkylaminocarbonyl group may be linear, branched or a $C_{3-10}$ cycloalkylaminocarbonyl group, and as specific examples, (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonanyl)aminocarbonyl, (methyl, n-decyl)aminocarbonyl, (ethyl, n-heptyl)aminocarbonyl, (ethyl, n-octyl)aminocarbonyl, (ethyl, n-nonanyl)aminocarbonyl, (ethyl, n-decyl)aminocarbonyl or the like may be mentioned.

A $C_{1-10}$ alkylaminosulfonyl group may be linear, branched, a $C_{3-10}$ cycloalkylsulfonylamino group or a di-$C_{1-10}$ alkylaminosulfonyl group, and as specific examples, methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyl-n-propylaminosulfonyl, 2,2-dimethyl-n-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosulfonyl, 1,1-dimethyl-n-butylaminosulfonyl, 1,2-dimethyl-n-butylaminosulfonyl, 1,3-dimethyl-n-butylaminosulfonyl, 2,2-dimethyl-n-butylaminosulfonyl, 2,3-dimethyl-n-butylaminosulfonyl, 3,3-dimethyl-n-butylaminosulfonyl, 1-ethyl-n-butylaminosulfonyl, 2-ethyl-n-butylaminosulfonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimethyl-1-n-octylaminosulfonyl, 3,7-dimethyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

A di-$C_{1-10}$ alkylaminosulfonyl group may be symmetric or asymmetric. A symmetric di-$C_{1-10}$ dialkylaminosulfonyl group may be linear, branched or a $C_{3-10}$ cycloalkylaminosulfonyl group, and as specific examples, dimethylaminosulfonyl, diethylaminosulfonyl, di-n-propylaminosulfonyl, di-1-propylaminosulfonyl, di-c-propylaminosulfonyl, di-n-butylaminosulfonyl, di-1-butylaminosulfonyl, di-s-butylaminosulfonyl, di-t-butylaminosulfonyl, di-c-butylaminosulfonyl, di-(1-methyl-c-propyl)aminosulfonyl, di-(2-methyl-c-propyl)aminosulfonyl, di-n-pentylaminosulfonyl, di-(1-methyl-n-butyl)aminosulfonyl, di-(2-methyl-n-butyl)aminosulfonyl, di-(3-methyl-n-butyl)aminosulfonyl, di-(1,1-dimethyl-n-propyl)aminosulfonyl, di-(1,2-dimethyl-n-propyl)aminosulfonyl, di-(2,2-dimethyl-n-propyl)aminosulfonyl, di-(1-ethyl-n-propyl)aminosulfonyl, di-c-pentylaminosulfonyl, di-(1-methyl-c-butyl)aminosulfonyl, di-(2-methyl-c-butyl)aminosulfonyl, di-(3-methyl-c-butyl)aminosulfonyl, di-(1,2-dimethyl-c-propyl)aminosulfonyl, di-(2,3-dimethyl-c-propyl)aminosulfonyl, di-(1-ethyl-c-propyl)aminosulfonyl, di-(2-ethyl-c-propyl)aminosulfonyl, di-n-hexylaminosulfonyl, di-(1-methyl-n-pentyl)aminosulfonyl, di-(2-methyl-n-pentyl)aminosulfonyl, di-(3-methyl-n-pentyl)aminosulfonyl, di-(4-methyl-n-pentyl)aminosulfonyl, di-(1,1-dimethyl-n-butyl)aminosulfonyl, di-(1,2-dimethyl-n-butyl)aminosulfonyl, di-(1,3-dimethyl-n-butyl)aminosulfonyl, di-(2,2-dimethyl-n-butyl)aminosulfonyl, di-(2,3-dimethyl-n-butyl)aminosulfonyl, di-(3,3-dimethyl-n-butyl)aminosulfonyl, di-(1-ethyl-n-butyl)aminosulfonyl, di-(2-ethyl-n-butyl)aminosulfonyl, di-(1,1,2-trimethyl-n- propyl)aminosulfonyl, di-(1,2,2-trimethyl-n-propyl)aminosulfonyl, di-(1-ethyl-1-methyl-n-propyl)aminosulfonyl, di-(1-ethyl-2-methyl-n-propyl)aminosulfonyl, di-c-hexylaminosulfonyl, di-(1-methyl-c-pentyl)aminosulfonyl, di-(2-methyl-c-pentyl)aminosulfonyl, di-(3-methyl-c-pentyl)aminosulfonyl, di-(1-ethyl-c-butyl)aminosulfonyl, di-(2-ethyl-c-butyl)aminosulfonyl, di-(3-ethyl-c-butyl)aminosulfonyl, di-(1,2-dimethyl-c-butyl)aminosulfonyl, di-(1,3-dimethyl-c-butyl)aminosulfonyl, di-(2,2-dimethyl-c-butyl)aminosulfonyl, di-(2,3-dimethyl-c-butyl)aminosulfonyl, di-(2,4-dimethyl-c-butyl)aminosulfonyl, di-(3,3-dimethyl-c-butyl)aminosulfonyl, di-(1-n-propyl-c-propyl)aminosulfonyl, di-(2-n-propyl-c-propyl)aminosulfonyl, di-(1-i-propyl-c-propyl)aminosulfonyl, di-(2-i-propyl-c-propyl)aminosulfonyl, di-(1,2,2-trimethyl-c-propyl)aminosulfonyl, di-(1,2,3-trimethyl-c-propyl)aminosulfonyl, di-(2,2,3-trimethyl-c-propyl)aminosulfonyl, di-(1-ethyl-2-methyl-c-propyl)aminosulfonyl, di-(2-ethyl-1-methyl-c-propyl)aminosulfonyl, di-(2-ethyl-2-methyl-c-propyl)aminosulfonyl, di-(2-ethyl-3-methyl-c-propyl)aminosulfonyl, di-(1-methyl-1-ethyl-n-pentyl)aminosulfonyl, di-(1-heptyl)aminosulfonyl, di-(2-heptyl)aminosulfonyl, di-(1-ethyl-1,2-dimethyl-n-propyl)aminosulfonyl, di-(1-ethyl-2,2-dimethyl-n-propyl)aminosulfonyl, di-(1-octyl)aminosulfonyl, di-(3-octyl)aminosulfonyl, di-(4-methyl-3-n-heptyl)aminosulfonyl, di-(6-methyl-2-n-heptyl)aminosulfonyl, di-(2-propyl-1-n-heptyl)aminosulfonyl, di-(2,4,4-trimethyl-1-n-pentyl)aminosulfonyl, di-(1-nonyl)aminosulfonyl, di-(2-nonyl)aminosulfonyl, di-(2,6-dimethyl-4-n-heptyl)aminosulfonyl, di-(3-ethyl-2,2-dimethyl-3-n-pentyl)aminosulfonyl, di-(3,5,5-trimethyl-1-n-hexyl)aminosulfonyl, di-(1-decyl)aminosulfonyl, di-(2-decyl)aminosulfonyl, di-(4-decyl)aminosulfonyl, di-(3,7-dimethyl-1-n-octyl)aminosulfonyl, di-(3,7-dimethyl-3-n-octyl)aminosulfonyl or the like may be mentioned.

An asymmetric di-$C_{1-10}$ alkylaminosulfonyl group may be linear, branched or a $C_{3-10}$ cycloalkylaminosulfonyl group, and as specific examples, (methyl, ethyl)aminosulfonyl, (methyl, n-propyl)aminosulfonyl, (methyl, i-propyl)aminosulfonyl, (methyl, c-propyl)aminosulfonyl, (methyl, n-butyl)aminosulfonyl, (methyl, i-butyl)aminosulfonyl, (methyl, s-butyl)aminosulfonyl, (methyl, t-butyl)aminosulfonyl, (methyl, n-pentyl)aminosulfonyl, (methyl, c-pentyl)aminosulfonyl, (methyl, n-hexyl)aminosulfonyl, (methyl, c-hexyl)aminosulfonyl, (ethyl, n-propyl)aminosulfonyl, (ethyl, i-propyl)aminosulfonyl, (ethyl, c-propyl)aminosulfonyl, (ethyl, n-butyl)aminosulfonyl, (ethyl, i-butyl)aminosulfonyl, (ethyl, s-butyl)aminosulfonyl, (ethyl, t-butyl)aminosulfonyl, (ethyl, n-pentyl)aminosulfonyl, (ethyl, c-pentyl)aminosulfonyl, (ethyl, n-hexyl)aminosulfonyl, (ethyl, c-hexyl)aminosulfonyl, (n-propyl, i-propyl)aminosulfonyl, (n-propyl, c-propyl)aminosulfonyl, (n-propyl, n-butyl)aminosulfonyl, (n-propyl, i-butyl)aminosulfonyl, (n-propyl, s-butyl)aminosulfonyl, (n-propyl, t-butyl)aminosulfonyl, (n-propyl, n-pentyl)aminosulfonyl, (n-propyl, c-pentyl)aminosulfonyl, (n-propyl, n-hexyl)aminosulfonyl, (n-propyl, c-hexyl)aminosulfonyl, (i-propyl, c-propyl)aminosulfonyl, (i-propyl, n-butyl)aminosulfonyl, (i-propyl, i-butyl)aminosulfonyl, (i-propyl, s-butyl)aminosulfonyl, (i-propyl, t-butyl)aminosulfonyl, (i-propyl, n-pentyl)aminosulfonyl, (i-propyl, c-pentyl)aminosulfonyl, (i-propyl, n-hexyl)aminosulfonyl, (i-propyl, c-hexyl)aminosulfonyl, (c-propyl, n-butyl)aminosulfonyl, (c-propyl, i-butyl)aminosulfonyl, (c-propyl, s-butyl)aminosulfonyl, (c-propyl, t-butyl)aminosulfonyl, (c-propyl, n-pentyl)aminosulfonyl, (c-propyl, c-pentyl)aminosulfonyl, (c-propyl, n-hexyl)aminosulfonyl, (c-propyl, c-hexyl)aminosulfonyl, (n-butyl, i-butyl)aminosulfonyl, (n-butyl, s-butyl)aminosulfonyl, (n-butyl, t-butyl)aminosulfonyl, (n-butyl, n-pentyl)aminosulfonyl, (n-butyl, c-pentyl)aminosulfonyl, (n-butyl, n-hexyl)aminosulfonyl, (n-butyl, c-hexyl)aminosulfonyl, (i-butyl, s-butyl)aminosulfonyl, (i-butyl, t-butyl)aminosulfonyl, (i-butyl, n-pentyl)aminosulfonyl, (i-butyl, c-pentyl)aminosulfonyl, (i-butyl, n-hexyl)aminosulfonyl, (i-butyl, c-hexyl)aminosulfonyl, (s-butyl, t-butyl)aminosulfonyl, (s-butyl, n-pentyl)aminosulfonyl, (s-butyl, c-pentyl)aminosulfonyl, (s-butyl, n-hexyl)aminosulfonyl, (s-butyl, c-hexyl)aminosulfonyl, (t-butyl, n-pentyl)aminosulfonyl, (t-butyl, c-pentyl)aminosulfonyl, (t-butyl, n-hexyl)aminosulfonyl, (t-butyl, c-hexyl)aminosulfonyl, (n-pentyl, c-pentyl)aminosulfonyl, (n-pentyl, n-hexyl)aminosulfonyl, (n-pentyl, c-hexyl)aminosulfonyl, (c-pentyl, n-hexyl)aminosulfonyl, (c-pentyl, c-hexyl)aminosulfonyl, (n-hexyl, c-hexyl)aminosulfonyl, (methyl, n-heptyl)aminosulfonyl, (methyl, n-octyl)aminosulfonyl, (methyl, n-nonanyl)aminosulfonyl, (methyl, n-decyl)aminosulfonyl, (ethyl, n-heptyl)aminosulfonyl, (ethyl, n-octyl)aminosulfonyl, (ethyl, n-nonanyl)aminosulfonyl, (ethyl, n-decyl)aminosulfonyl or the like may be mentioned.

A $C_{2-14}$ arylene group is a bivalent group formed by removing a hydrogen atom from a ring-constituting atom in a $C_{2-14}$ aryl group, and as specific examples,

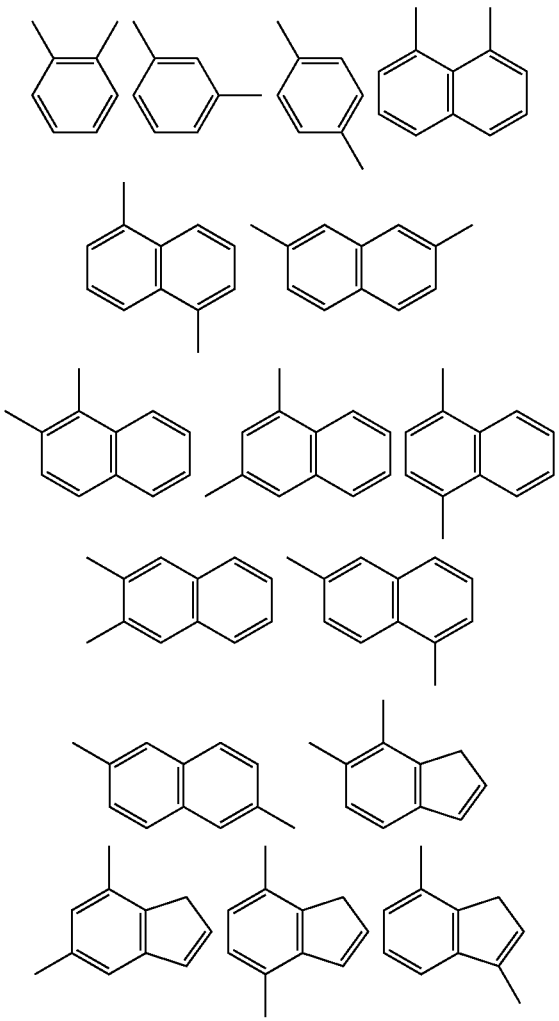

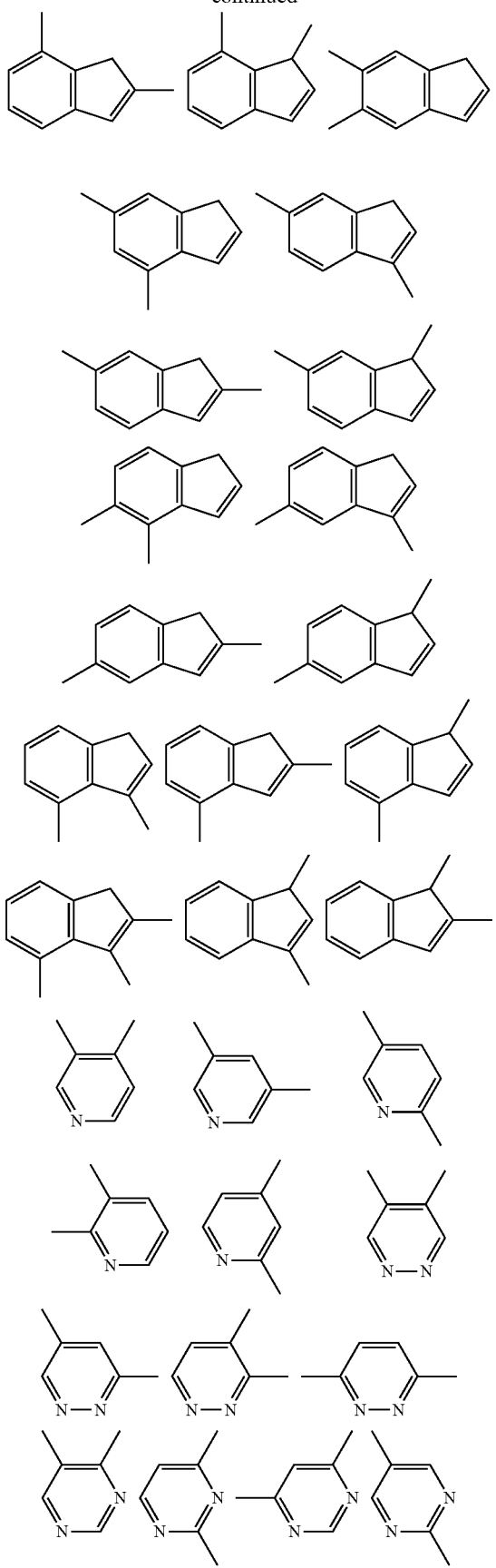
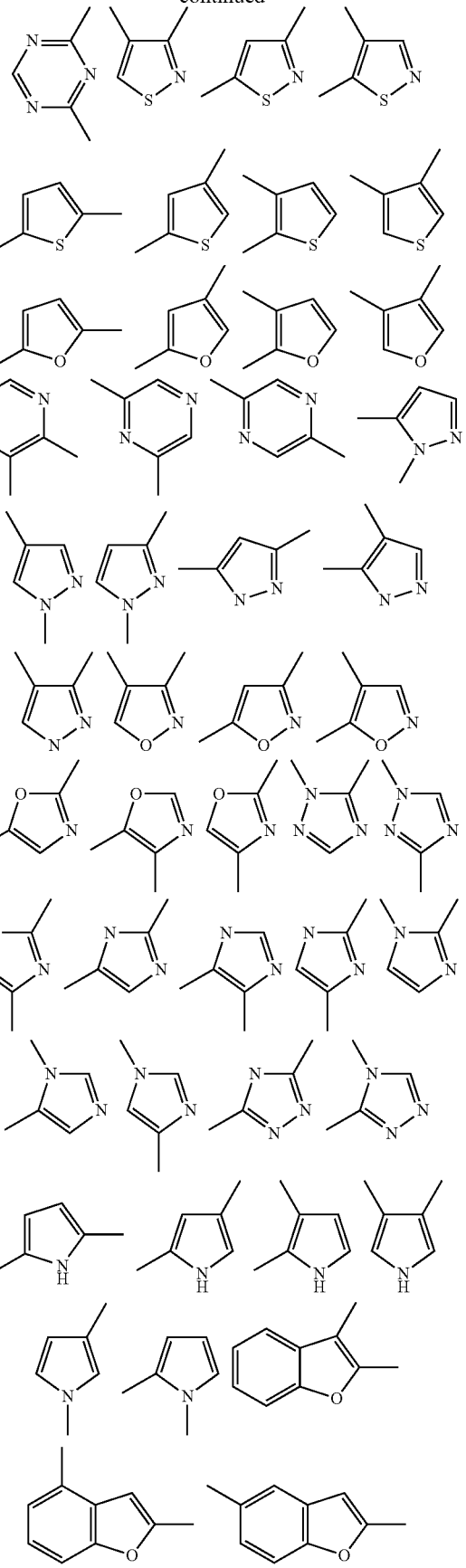

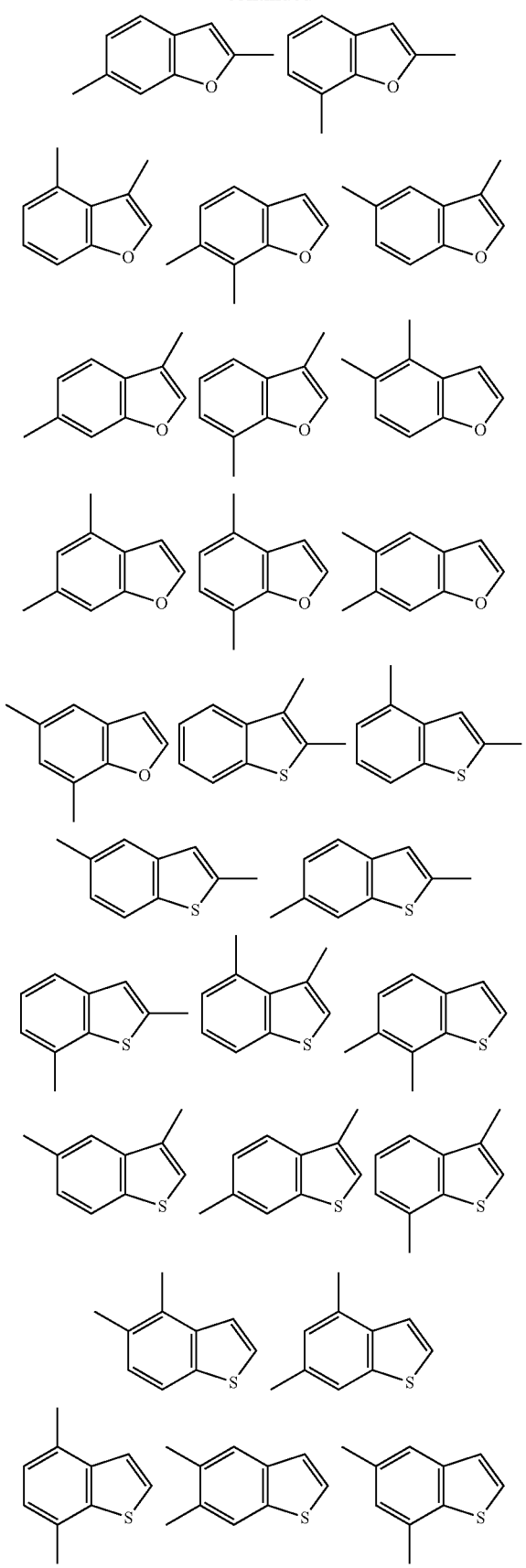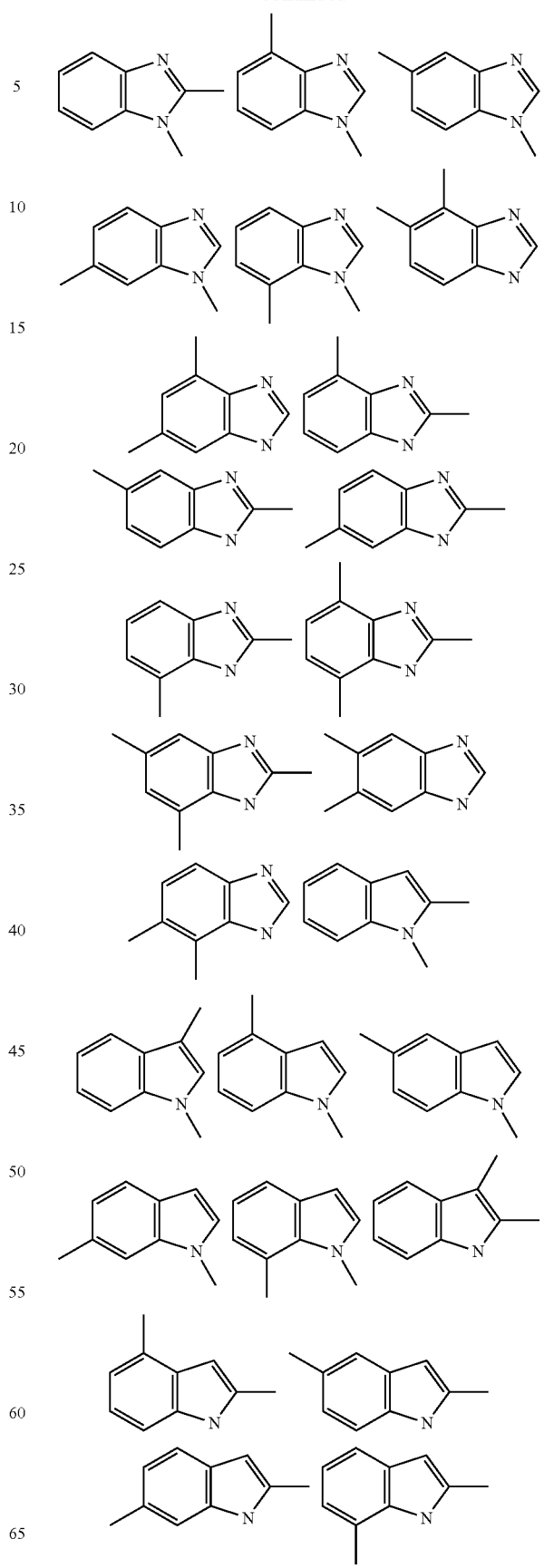

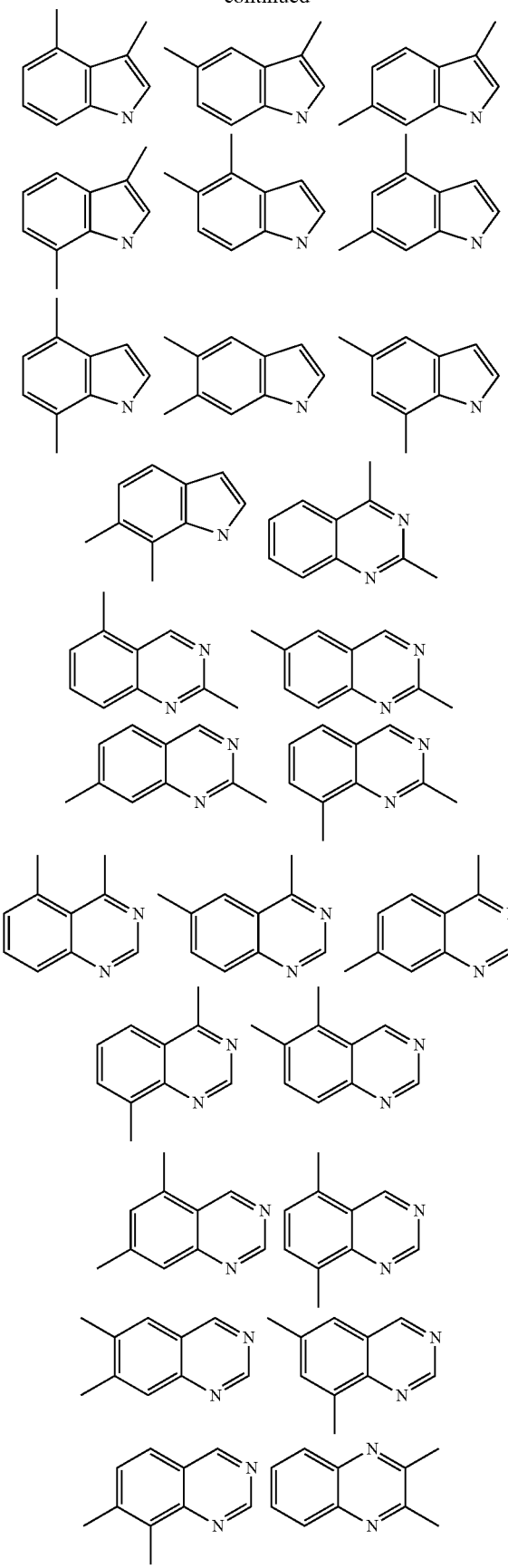
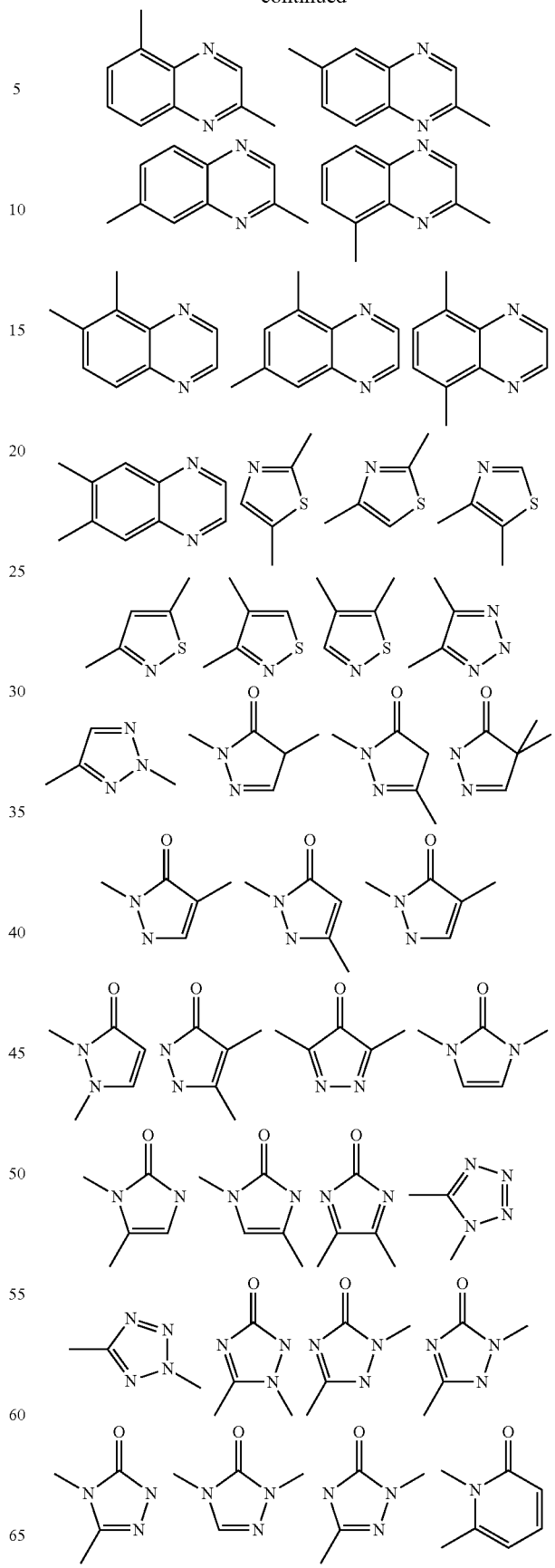

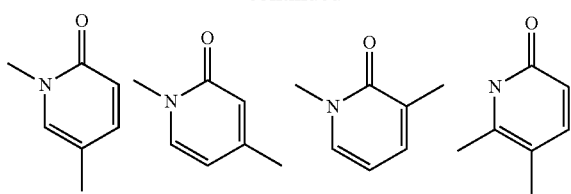
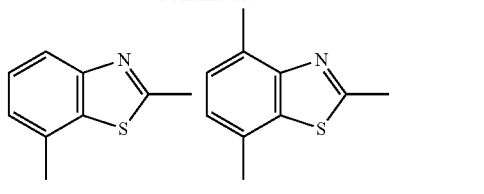
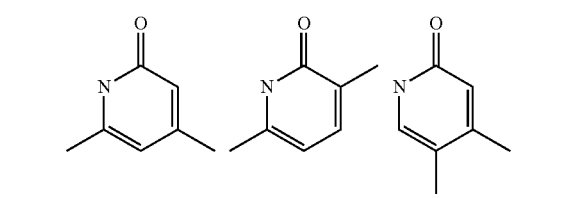
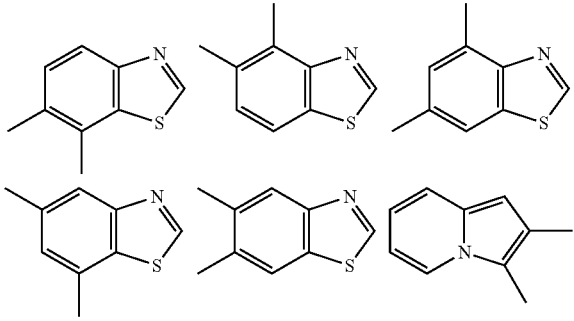
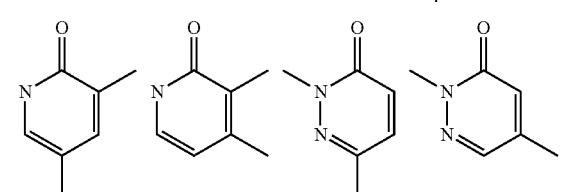
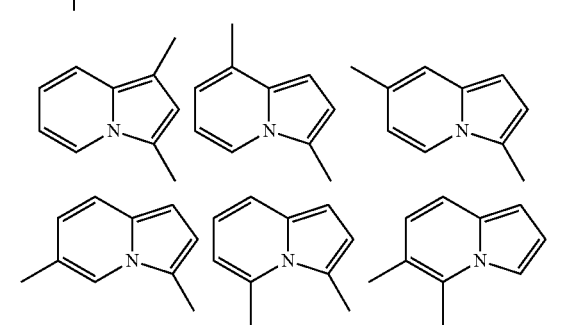
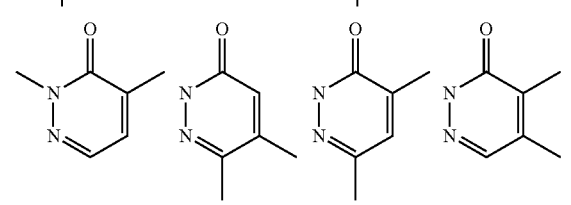
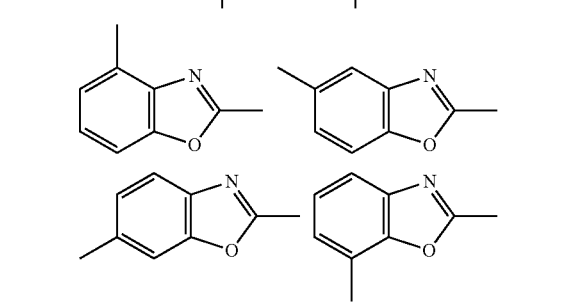
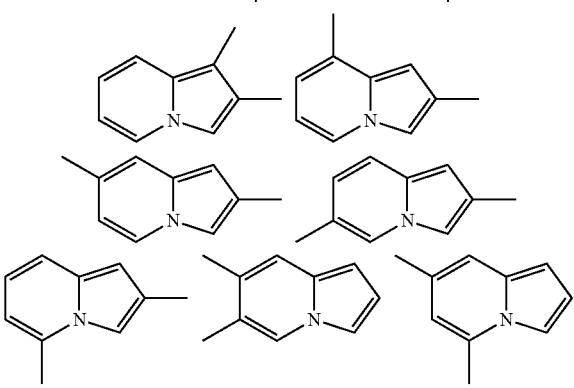
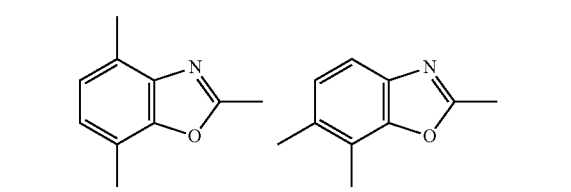
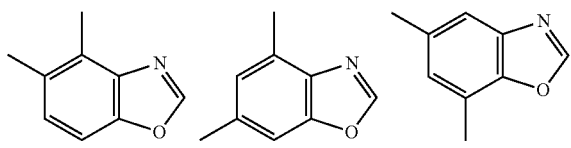
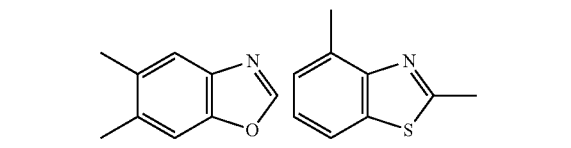
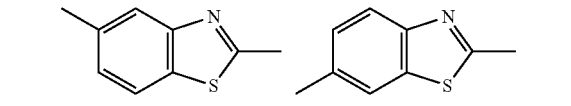

51
-continued
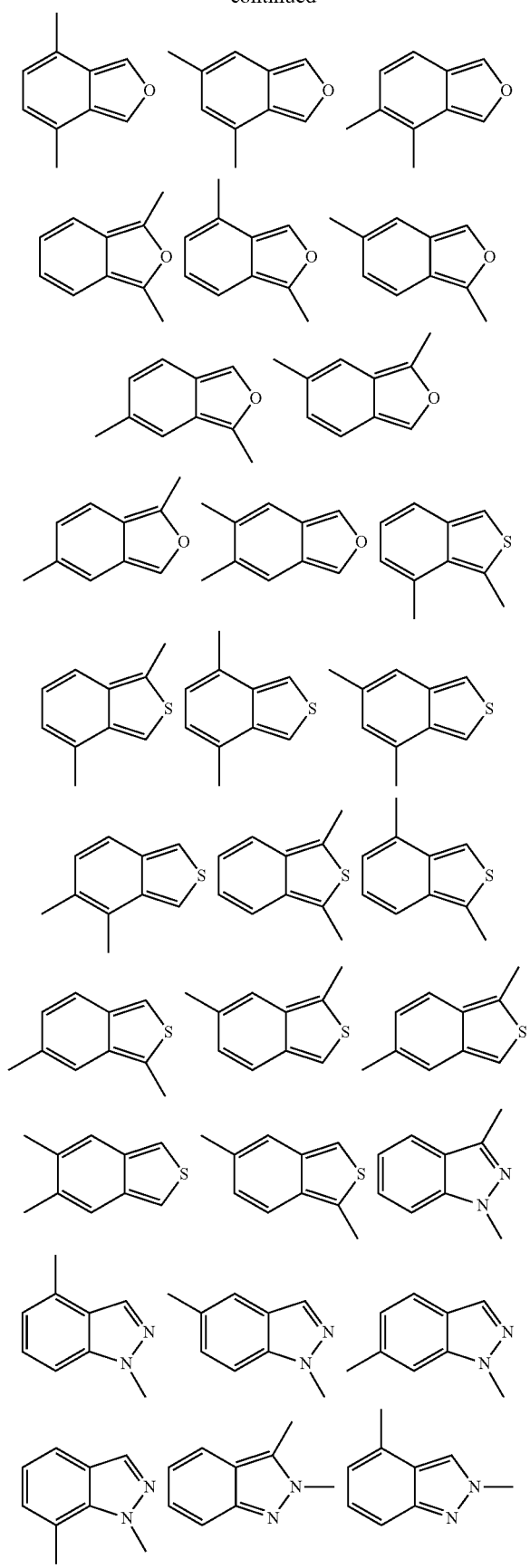
52
-continued
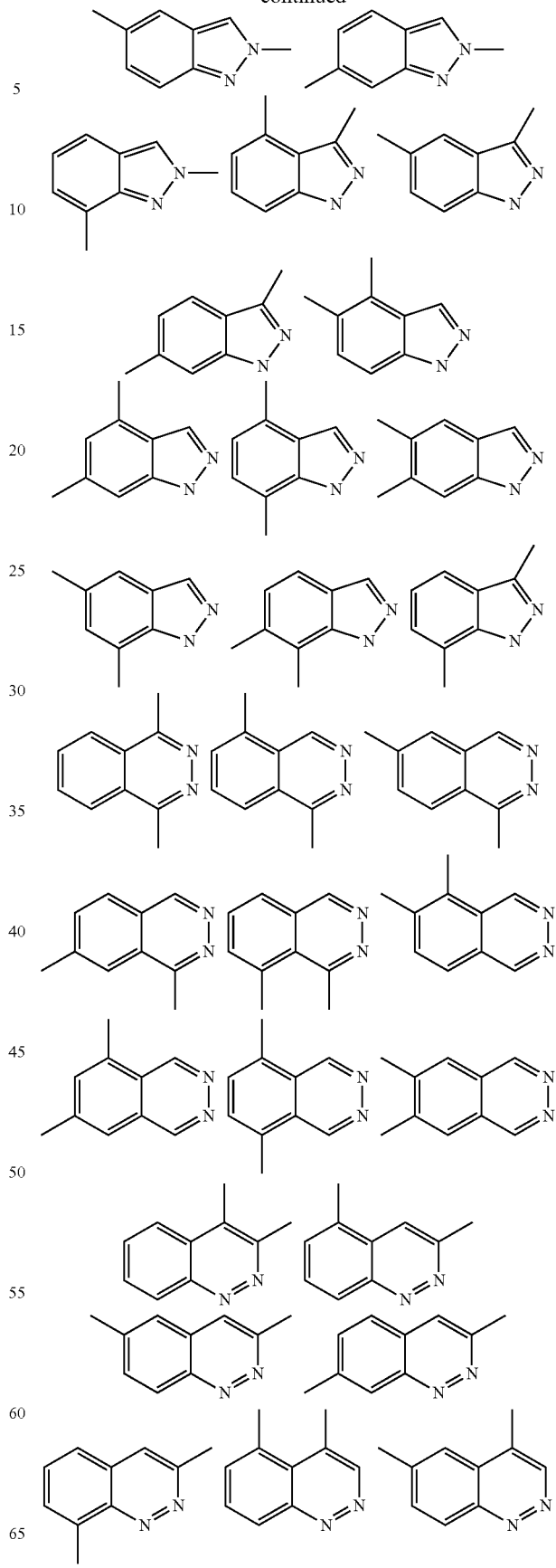

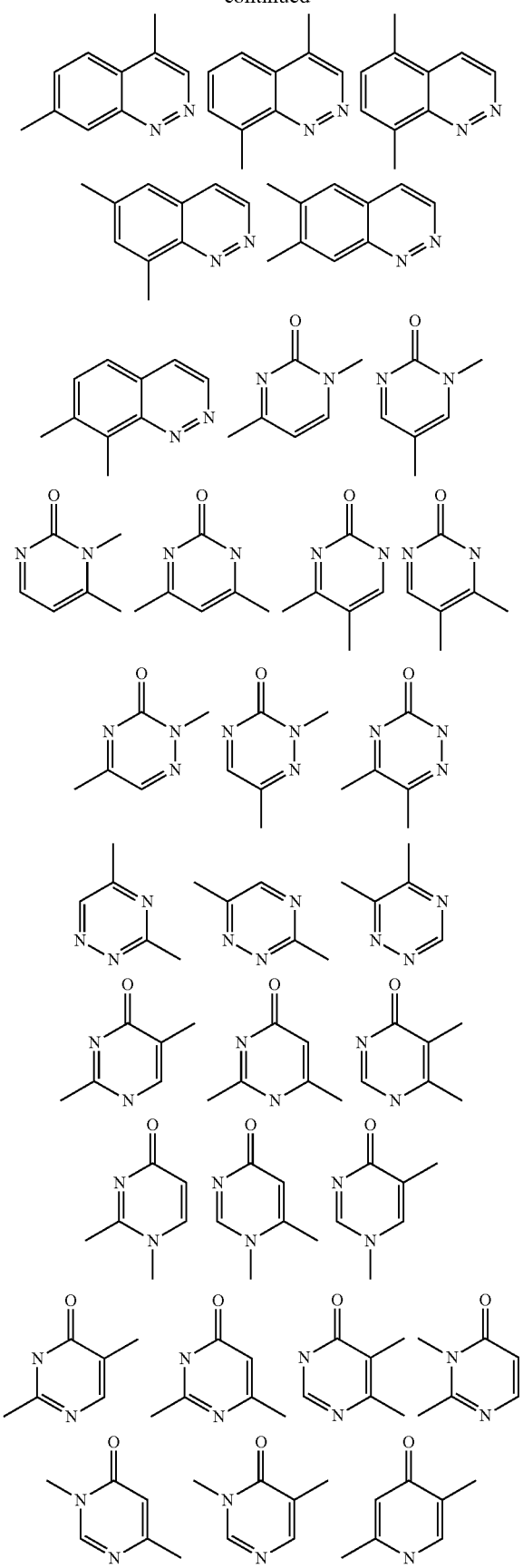
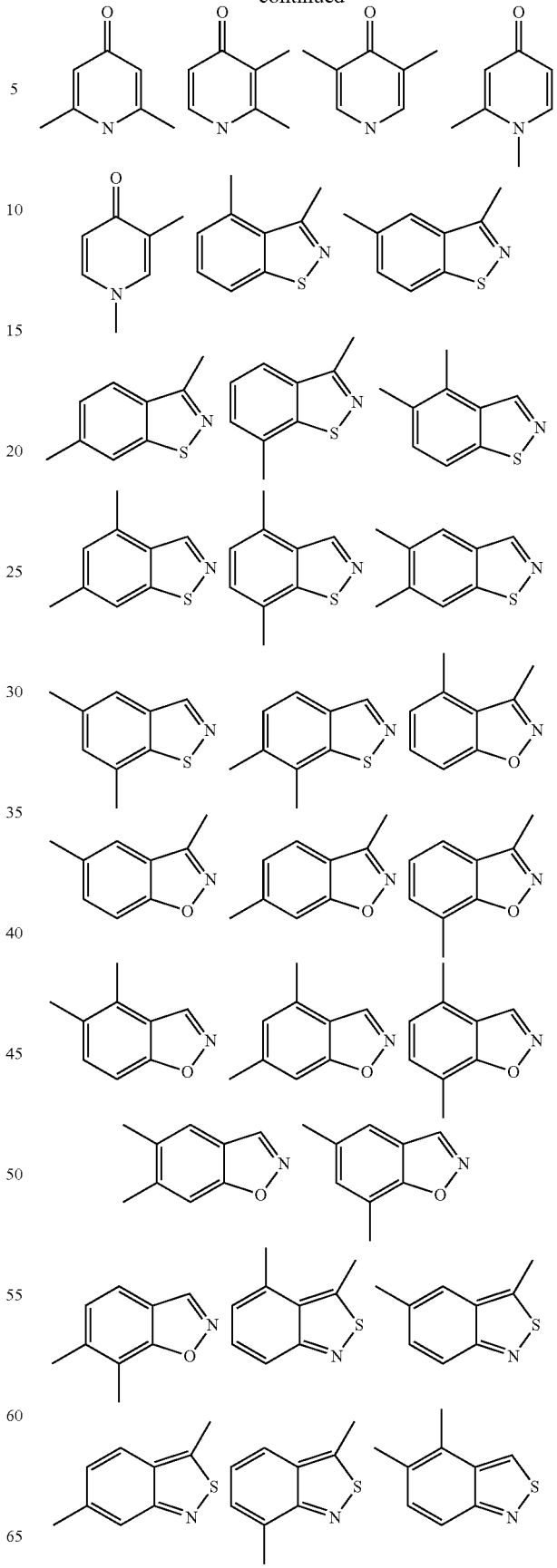

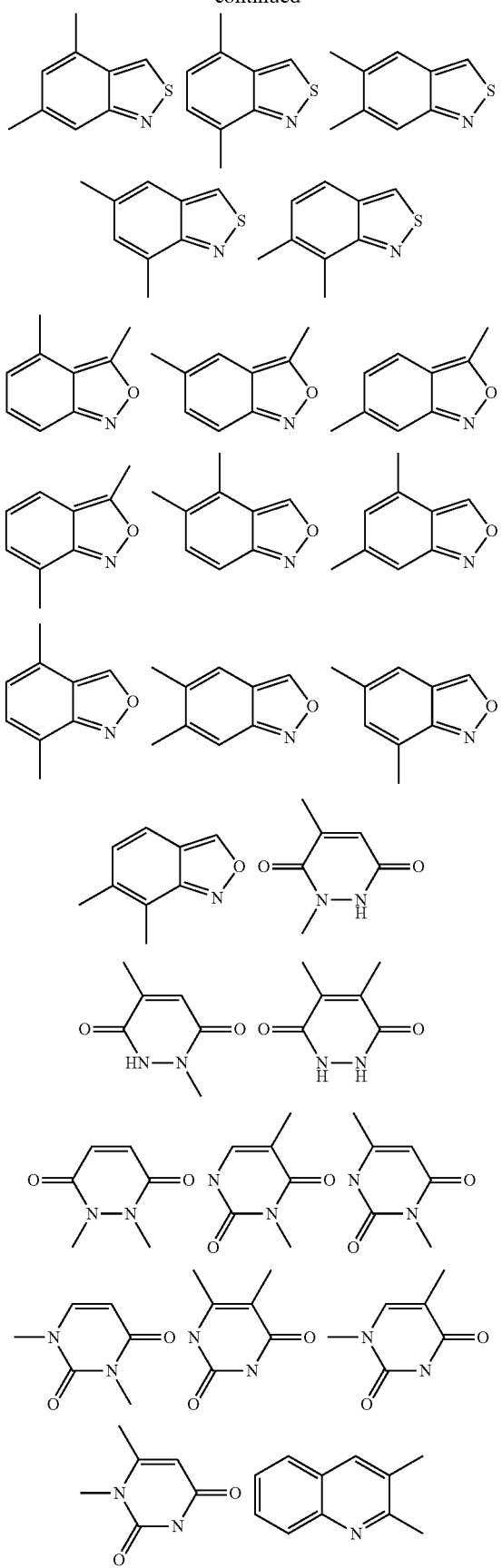
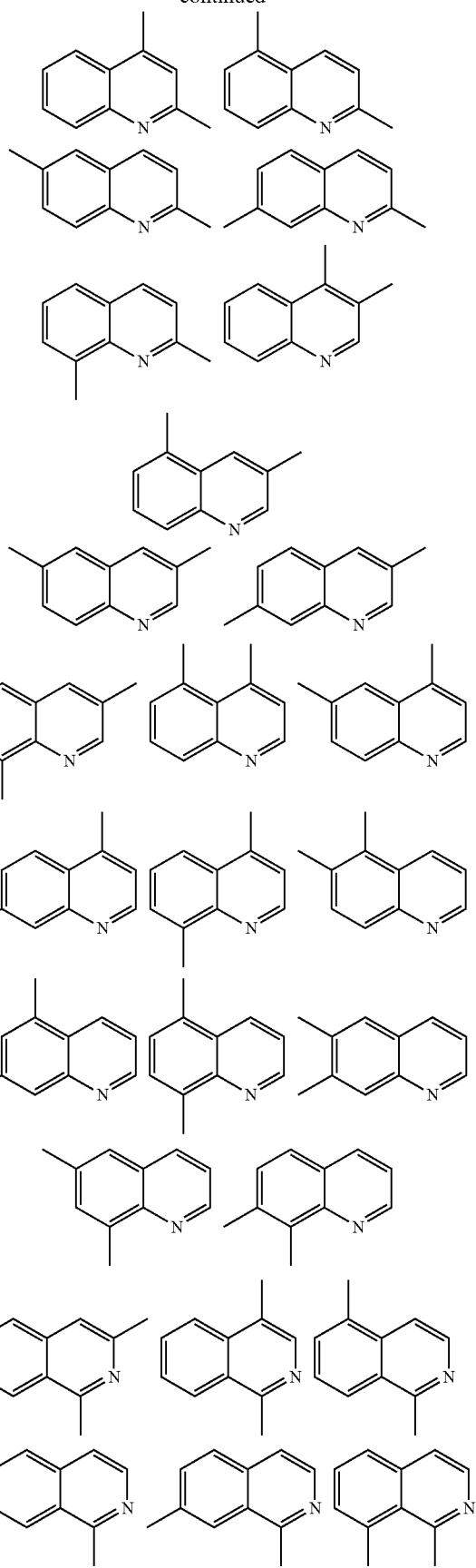

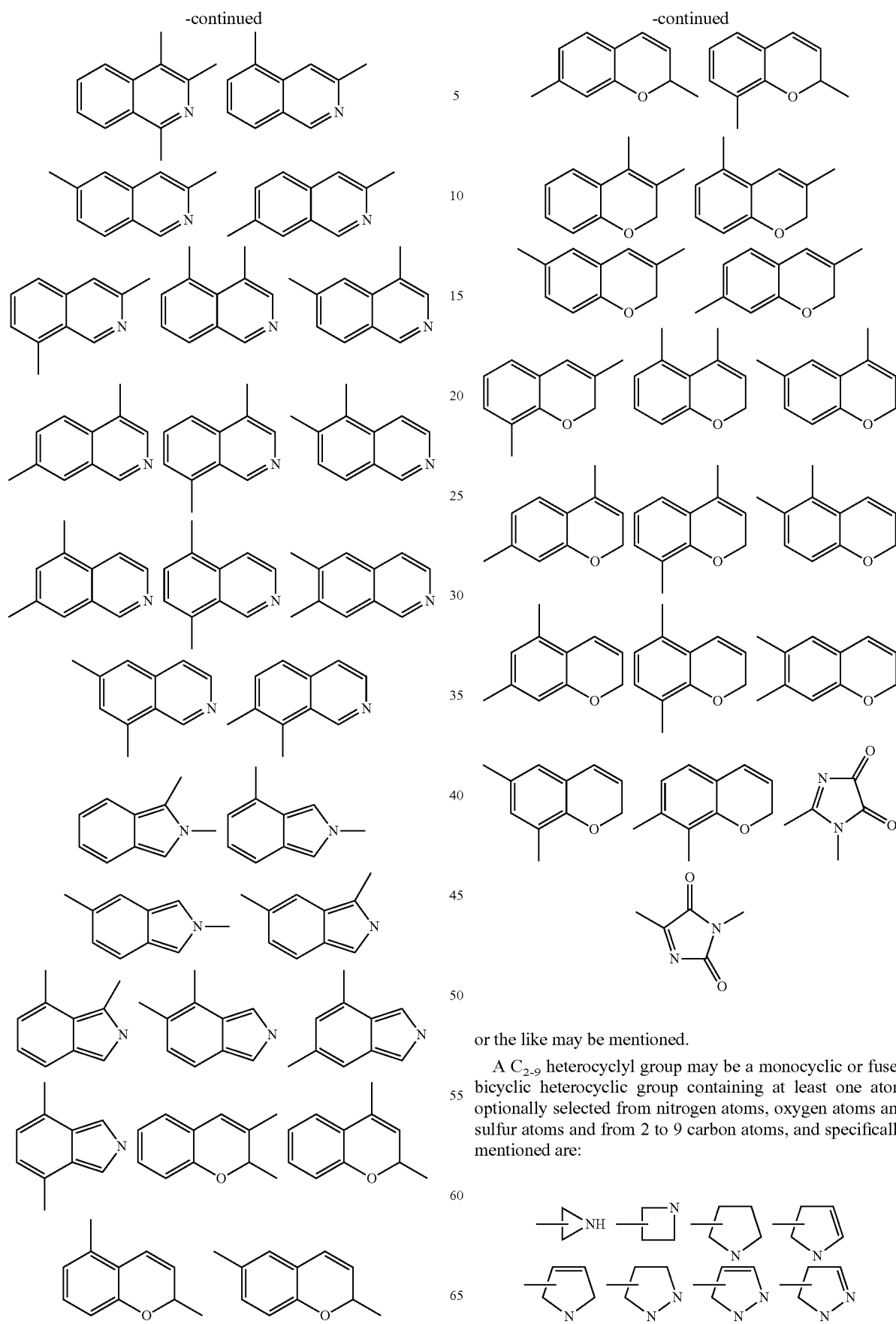
or the like may be mentioned.
A $C_{2-9}$ heterocyclyl group may be a monocyclic or fused bicyclic heterocyclic group containing at least one atom optionally selected from nitrogen atoms, oxygen atoms and sulfur atoms and from 2 to 9 carbon atoms, and specifically mentioned are:
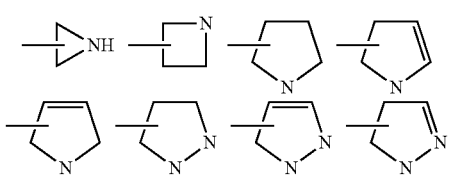

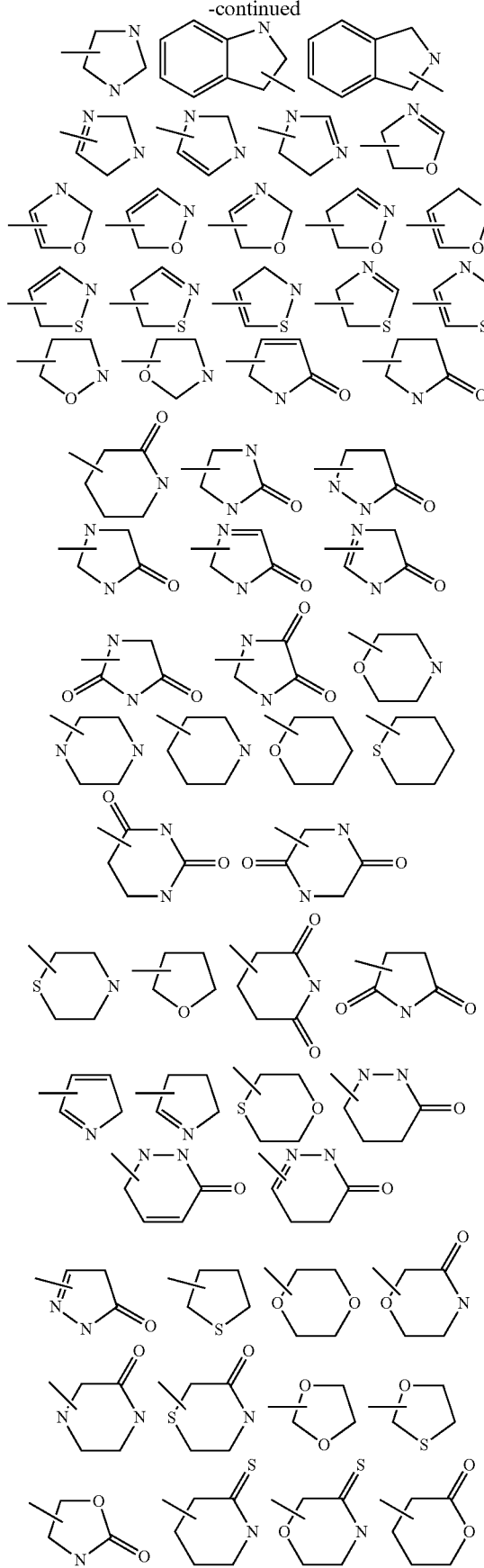
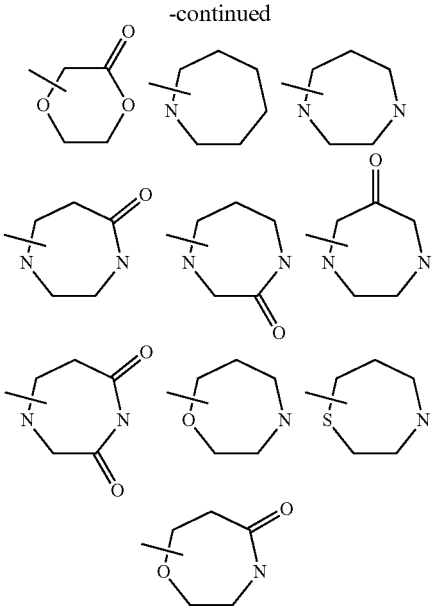

The protecting group in a protected hydroxyl group, a protected amino group or a protected thiol group or as an amino-protecting group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, P-AOM: p-anisyloxymethyl and the like, preferably benzyloxymethyl), a $C_{1-4}$ alkylaminomethyl group (such as dimethylaminomethyl), a substituted acetamidomethyl group (such as Acm: acetamidomethyl, Tacm: trimethylacetamidomethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, p-bromobenzoyl, p-nitrobenzoyl, 2,4-dinitrobenzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, o-nitrobenzenesulfonyl, p-nitrobenzenesulfonyl, 2,4-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

In addition, a 1-methyl-1-methoxyethyl group, a 1-ethoxyethyl group, a 2,2,2-trichloroethyl group, a 2-trimethylsilylethoxy group, a t-butyl group, an allyl group, a benzyl group, a p-methoxybenzyl group, a 2,4-dinitrophenyl group, a p-chlorophenyl group, a p-methoxyphenyl group, a tetrahydropyranyl group, a tetrahydrofuranyl group or the like may be mentioned.

Preferred examples of the substituents in the compounds to be used in the present invention are given below.

Preferred examples of $R^1$ are a hydrogen atom and a $C_{1-6}$ alkyl group (the $C_{1-6}$ alkyl group may be substituted with one or more halogen atoms), a more preferred example is a hydrogen atom and a $C_{1-3}$ alkyl group, and a particularly preferred example is a methyl group.

Preferred examples of $R^2$, $R^3$ and $R^6$ are a hydrogen atom and a $C_{1-3}$ alkyl group (the $C_{1-3}$ alkyl group may be substituted with one or more halogen atoms), and a more preferred example is a hydrogen atom.

Preferred examples of $R^4$ are a hydrogen atom and a $C_{1-6}$ alkyl group (the $C_{1-6}$ alkyl group may be substituted with one or more halogen atoms), more preferred examples are a hydrogen atom and a $C_{1-6}$ alkyl group, and a more preferred example is a hydrogen atom.

Preferred examples of $R^5$ are a phenyl group, a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 1-1,2,4-triazole group, a 3-1,2,4-triazole group, a 5-1,2,4-triazole group, a 1-1,2,3-triazole group, a 4-1,2,3-triazole group, a 5-1,2,3-triazole group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group and a 3-1,2,5-thiadiazolyl group (the phenyl group, the 2-thienyl group, the 3-thienyl group, the 2-furyl group, the 3-furyl group, the 2-pyranyl group, the 3-pyranyl group, the 4-pyranyl group, the 1-pyrrolyl group, the 2-pyrrolyl group, the 3-pyrrolyl group, the 1-imidazolyl group, the 2-imidazolyl group, the 4-imidazolyl group, the 1-pyrazolyl group, the 3-pyrazolyl group, the 4-pyrazolyl group, the 2-thiazolyl group, the 4-thiazolyl group, the 5-thiazolyl group, the 3-isothiazolyl group, the 4-isothiazolyl group, the 5-isothiazolyl group, the 1-1,2,4-triazole group, the 3-1,2,4-triazole group, the 5-1,2,4-triazole group, the 1-1,2,3-triazole group, the 4-1,2,3-triazole group, the 5-1,2,3-triazole group, the 2-oxazolyl group, the 4-oxazolyl group, the 5-oxazolyl group, the 3-isoxazolyl group, the 4-isoxazolyl group, the 5-isoxazolyl group, the 2-pyridyl group, the 3-pyridyl group, the 4-pyridyl group, the 2-pyrazinyl group, the 2-pyrimidinyl group, the 4-pyrimidinyl group, the 5-pyrimidinyl group, the 3-pyridazinyl group, the 4-pyridazinyl group, the 2-1,3,4-oxadiazolyl group, the 2-1,3,4-thiadiazolyl group, the 3-1,2,4-oxadiazolyl group, the 5-1,2,4-oxadiazolyl group, the 3-1,2,4-thiadiazolyl group, the 5-1,2,4-thiadiazolyl group, the 3-1,2,5-oxadiazolyl group and the 3-1,2,5-thiadiazolyl group are substituted with one or more substituents represented by any of the following formulae (V), (VI), (VII), (VIII), (IX), (X), (XI), (XII), (XIII), (XIV), (XV), (XVI), (XVII), (XVIII), (XIX), (XX), (XXI) and (XXII)).

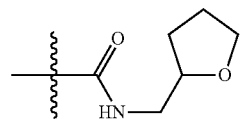

(V)

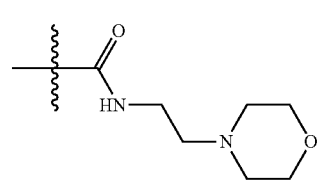

(VI)

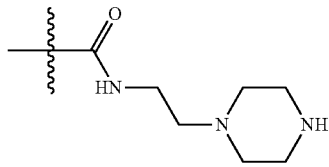

(VII)

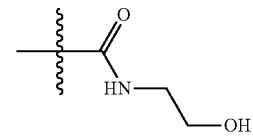

(VIII)

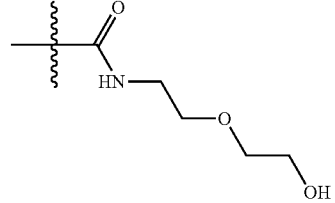

(IX)

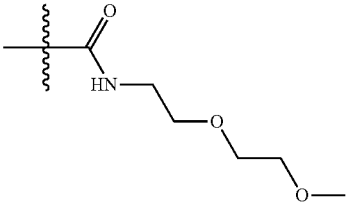

(X)

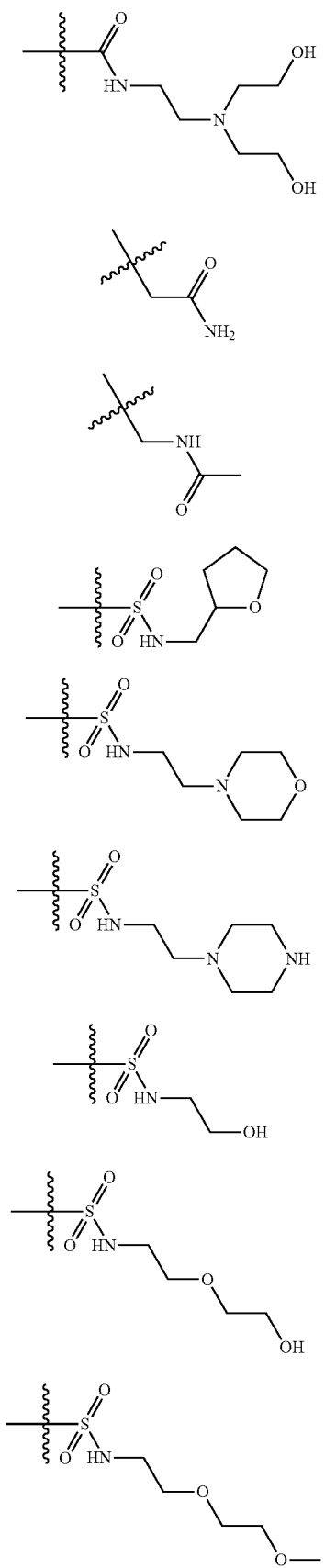
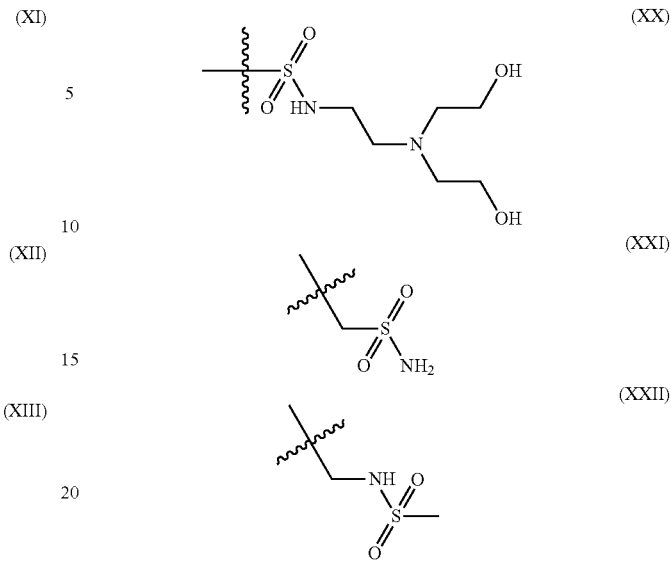

More preferred examples of $R^5$ are a phenyl group, a 2-thienyl group, a 3-thienyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group and a 4-pyridazinyl group (the phenyl group, the 2-thienyl group, the 3-thienyl group, the 2-pyridyl group, the 3-pyridyl group, the 4-pyridyl group, the 2-pyrazinyl group, the 2-pyrimidinyl group, the 4-pyrimidinyl group, the 5-pyrimidinyl group, the 3-pyridazinyl group and the 4-pyridazinyl group are substituted with one or more substituents represented by any of the above formulae (V), (VI), (VII), (VIII), (IX), (X), (XI), (XII), (XIII), (XIV), (XV), (XVI), (XVII), (XVIII), (XIX), (XX), (XXI) and (XXII)).

A particularly preferred example of $R^5$ is a phenyl group (the phenyl group is substituted with one or more substituents represented by any of the above formulae (V), (VI), (VII), (VIII), (IX), (X), (XI), (XII), (XIII), (XIV), (XV), (XVI), (XVII), (XVIII), (XIX), (XX), (XXI) and (XXII)).

Preferred examples of $R^7$ are a $C_{2-14}$ aryl group (the $C_{2-14}$ aryl group may optionally be substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), and a more preferred examples is a phenyl group (the phenyl group may optionally be substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)).

A particularly preferred example is a phenyl group (the phenyl group may optionally be substituted with one or more $C_{1-6}$ alkyl groups, one or more $C_{1-3}$ alkyl groups (the $C_{1-3}$ alkyl groups are optionally substituted with one or more halogen atoms), one or more halogen atoms, one or more $C_{1-3}$ alkoxy groups or one or more $C_{1-3}$ alkoxy groups (the $C_{1-3}$ alkoxy groups are optionally substituted with one or more halogen atoms)).

Specifically speaking, a particularly preferred example is a phenyl group (the phenyl group is optionally substituted with one or more methyl groups, one or more t-butyl groups, one or more halogen atoms, one or more methoxy groups, one or more trifluoromethyl groups or one or more trifluoromethoxy groups).

A preferred example of $Ar^1$ is the structure represented by the following formula (IV).

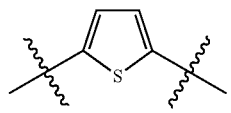
(IV)

A preferred example of X is OH.

A preferred example of Y is an oxygen atom.

A preferred example of Z is an oxygen atom.

Favorable compounds to be used for the present invention are shown below in Table 1-1 to Table 1-4.

Compounds wherein Ra, A and Q are any of the following combinations shown in Table 1, tautomers or pharmaceutically acceptable salts of the compounds or solvates thereof. The symbols in Table 1-1 to Table 1-4 denote the following substituents.

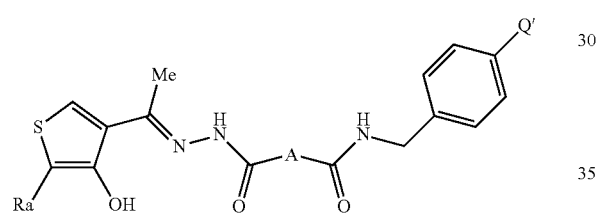

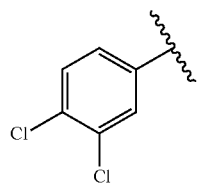
$Ra^1$

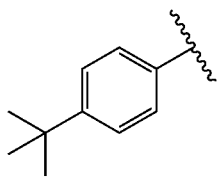
$Ra^2$

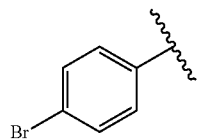
$Ra^3$

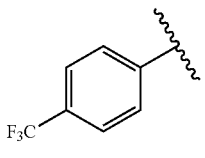
$Ra^4$

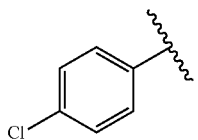
$Ra^5$

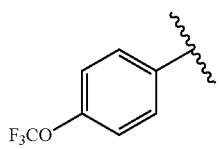
$Ra^6$

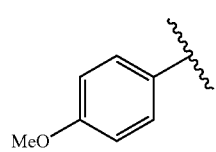
$Ra^7$

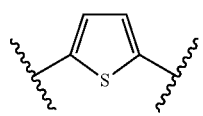
$A^1$

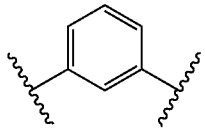
$A^2$

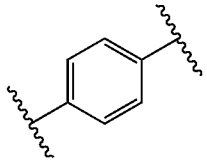
$A^3$

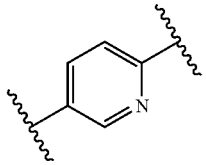
$A^4$

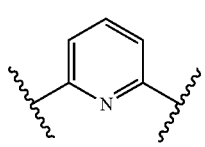
$A^5$

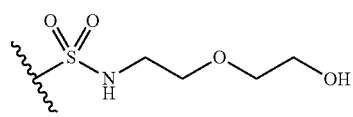
$Q^1$

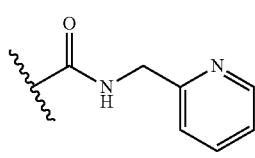
$Q^2$

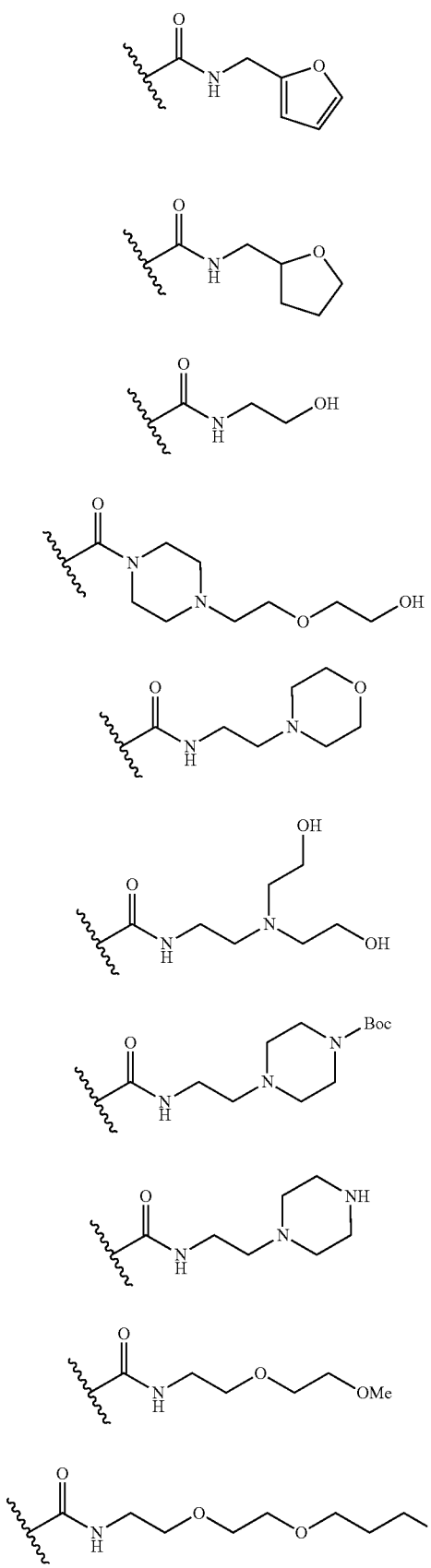
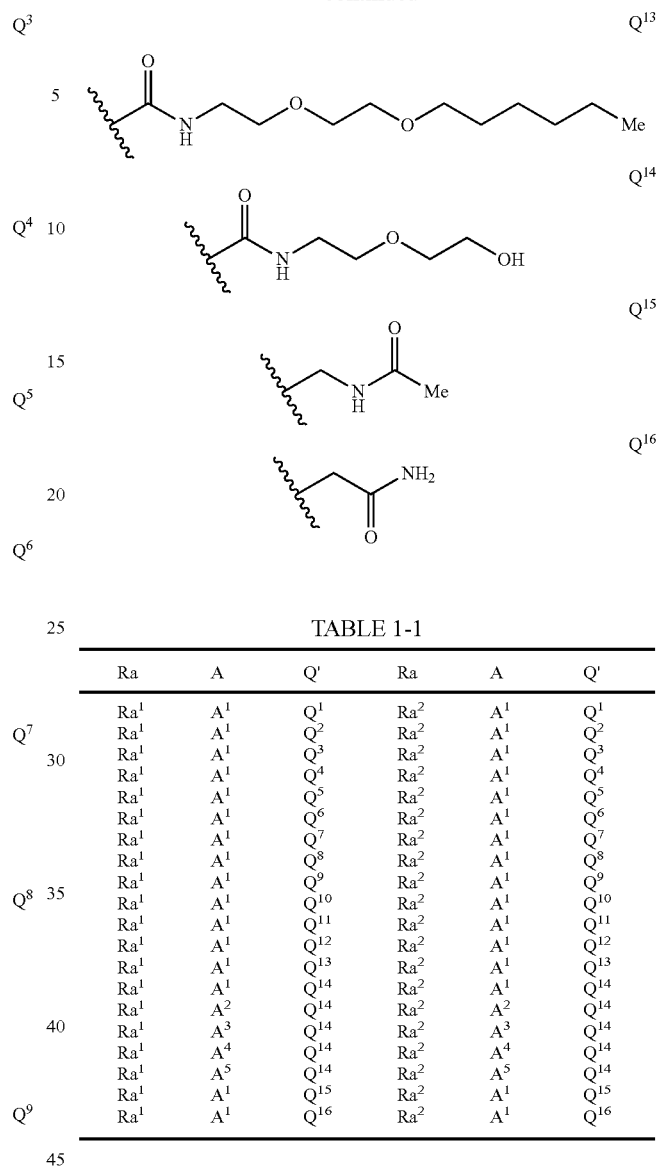

TABLE 1-1

| Ra | A | Q' | Ra | A | Q' |
|---|---|---|---|---|---|
| Ra¹ | A¹ | Q¹ | Ra² | A¹ | Q¹ |
| Ra¹ | A¹ | Q² | Ra² | A¹ | Q² |
| Ra¹ | A¹ | Q³ | Ra² | A¹ | Q³ |
| Ra¹ | A¹ | Q⁴ | Ra² | A¹ | Q⁴ |
| Ra¹ | A¹ | Q⁵ | Ra² | A¹ | Q⁵ |
| Ra¹ | A¹ | Q⁶ | Ra² | A¹ | Q⁶ |
| Ra¹ | A¹ | Q⁷ | Ra² | A¹ | Q⁷ |
| Ra¹ | A¹ | Q⁸ | Ra² | A¹ | Q⁸ |
| Ra¹ | A¹ | Q⁹ | Ra² | A¹ | Q⁹ |
| Ra¹ | A¹ | Q¹⁰ | Ra² | A¹ | Q¹⁰ |
| Ra¹ | A¹ | Q¹¹ | Ra² | A¹ | Q¹¹ |
| Ra¹ | A¹ | Q¹² | Ra² | A¹ | Q¹² |
| Ra¹ | A¹ | Q¹³ | Ra² | A¹ | Q¹³ |
| Ra¹ | A¹ | Q¹⁴ | Ra² | A¹ | Q¹⁴ |
| Ra¹ | A² | Q¹⁴ | Ra² | A² | Q¹⁴ |
| Ra¹ | A³ | Q¹⁴ | Ra² | A³ | Q¹⁴ |
| Ra¹ | A⁴ | Q¹⁴ | Ra² | A⁴ | Q¹⁴ |
| Ra¹ | A⁵ | Q¹⁴ | Ra² | A⁵ | Q¹⁴ |
| Ra¹ | A¹ | Q¹⁵ | Ra² | A¹ | Q¹⁵ |
| Ra¹ | A¹ | Q¹⁶ | Ra² | A¹ | Q¹⁶ |

TABLE 1-2

| Ra | A | Q' | Ra | A | Q' |
|---|---|---|---|---|---|
| Ra³ | A¹ | Q¹ | Ra⁴ | A¹ | Q¹ |
| Ra³ | A¹ | Q² | Ra⁴ | A¹ | Q² |
| Ra³ | A¹ | Q³ | Ra⁴ | A¹ | Q³ |
| Ra³ | A¹ | Q⁴ | Ra⁴ | A¹ | Q⁴ |
| Ra³ | A¹ | Q⁵ | Ra⁴ | A¹ | Q⁵ |
| Ra³ | A¹ | Q⁶ | Ra⁴ | A¹ | Q⁶ |
| Ra³ | A¹ | Q⁷ | Ra⁴ | A¹ | Q⁷ |
| Ra³ | A¹ | Q⁸ | Ra⁴ | A¹ | Q⁸ |
| Ra³ | A¹ | Q⁹ | Ra⁴ | A¹ | Q⁹ |
| Ra³ | A¹ | Q¹⁰ | Ra⁴ | A¹ | Q¹⁰ |
| Ra³ | A¹ | Q¹¹ | Ra⁴ | A¹ | Q¹¹ |
| Ra³ | A¹ | Q¹² | Ra⁴ | A¹ | Q¹² |
| Ra³ | A¹ | Q¹³ | Ra⁴ | A¹ | Q¹³ |
| Ra³ | A¹ | Q¹⁴ | Ra⁴ | A¹ | Q¹⁴ |
| Ra³ | A² | Q¹⁴ | Ra⁴ | A² | Q¹⁴ |
| Ra³ | A³ | Q¹⁴ | Ra⁴ | A³ | Q¹⁴ |
| Ra³ | A⁴ | Q¹⁴ | Ra⁴ | A⁴ | Q¹⁴ |
| Ra³ | A⁵ | Q¹⁴ | Ra⁴ | A⁵ | Q¹⁴ |
| Ra³ | A¹ | Q¹⁵ | Ra⁴ | A¹ | Q¹⁵ |
| Ra³ | A¹ | Q¹⁶ | Ra⁴ | A¹ | Q¹⁶ |

TABLE 1-3

| Ra | A | Q' | Ra | A | Q' |
|---|---|---|---|---|---|
| $Ra^5$ | $A^1$ | $Q^1$ | $Ra^6$ | $A^1$ | $Q^1$ |
| $Ra^5$ | $A^1$ | $Q^2$ | $Ra^6$ | $A^1$ | $Q^2$ |
| $Ra^5$ | $A^1$ | $Q^3$ | $Ra^6$ | $A^1$ | $Q^3$ |
| $Ra^5$ | $A^1$ | $Q^4$ | $Ra^6$ | $A^1$ | $Q^4$ |
| $Ra^5$ | $A^1$ | $Q^5$ | $Ra^6$ | $A^1$ | $Q^5$ |
| $Ra^5$ | $A^1$ | $Q^6$ | $Ra^6$ | $A^1$ | $Q^6$ |
| $Ra^5$ | $A^1$ | $Q^7$ | $Ra^6$ | $A^1$ | $Q^7$ |
| $Ra^5$ | $A^1$ | $Q^8$ | $Ra^6$ | $A^1$ | $Q^8$ |
| $Ra^5$ | $A^1$ | $Q^9$ | $Ra^6$ | $A^1$ | $Q^9$ |
| $Ra^5$ | $A^1$ | $Q^{10}$ | $Ra^6$ | $A^1$ | $Q^{10}$ |
| $Ra^5$ | $A^1$ | $Q^{11}$ | $Ra^6$ | $A^1$ | $Q^{11}$ |
| $Ra^5$ | $A^1$ | $Q^{12}$ | $Ra^6$ | $A^1$ | $Q^{12}$ |
| $Ra^5$ | $A^1$ | $Q^{13}$ | $Ra^6$ | $A^1$ | $Q^{13}$ |
| $Ra^5$ | $A^1$ | $Q^{14}$ | $Ra^6$ | $A^1$ | $Q^{14}$ |
| $Ra^5$ | $A^2$ | $Q^{14}$ | $Ra^6$ | $A^2$ | $Q^{14}$ |
| $Ra^5$ | $A^3$ | $Q^{14}$ | $Ra^6$ | $A^3$ | $Q^{14}$ |
| $Ra^5$ | $A^4$ | $Q^{14}$ | $Ra^6$ | $A^4$ | $Q^{14}$ |
| $Ra^5$ | $A^5$ | $Q^{14}$ | $Ra^6$ | $A^5$ | $Q^{14}$ |
| $Ra^5$ | $A^1$ | $Q^{15}$ | $Ra^6$ | $A^1$ | $Q^{15}$ |
| $Ra^5$ | $A^1$ | $Q^{16}$ | $Ra^6$ | $A^1$ | $Q^{16}$ |

TABLE 1-4

| Ra | A | Q' | Ra | A | Q' |
|---|---|---|---|---|---|
| $Ra^7$ | $A^1$ | $Q^1$ | $Ra^7$ | $A^1$ | $Q^{11}$ |
| $Ra^7$ | $A^1$ | $Q^2$ | $Ra^7$ | $A^1$ | $Q^{12}$ |
| $Ra^7$ | $A^1$ | $Q^3$ | $Ra^7$ | $A^1$ | $Q^{13}$ |
| $Ra^7$ | $A^1$ | $Q^4$ | $Ra^7$ | $A^1$ | $Q^{14}$ |
| $Ra^7$ | $A^1$ | $Q^5$ | $Ra^7$ | $A^2$ | $Q^{14}$ |
| $Ra^7$ | $A^1$ | $Q^6$ | $Ra^7$ | $A^3$ | $Q^{14}$ |
| $Ra^7$ | $A^1$ | $Q^7$ | $Ra^7$ | $A^4$ | $Q^{14}$ |
| $Ra^7$ | $A^1$ | $Q^8$ | $Ra^7$ | $A^5$ | $Q^{14}$ |
| $Ra^7$ | $A^1$ | $Q^9$ | $Ra^7$ | $A^1$ | $Q^{15}$ |
| $Ra^7$ | $A^1$ | $Q^{10}$ | $Ra^7$ | $A^1$ | $Q^{16}$ |

The compounds of the present invention represented by the formula (I) or pharmaceutically acceptable salts thereof may be in the form of arbitrary crystals or arbitrary hydrates, depending on the production conditions. The present invention covers these crystals, hydrates and mixtures thereof. They may be in the form of solvates with organic solvents such as acetone, ethanol and tetrahydrofuran, and the present invention covers any of these forms.

The compounds of the present invention represented by the formula (I) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases or amino acids. They may be salts with inorganic acids (such as hydrochloric acid, hydrobromic acid, phosphoric acid and sulfuric acid) or organic acids (such as acetic acid, citric acid, maleic acid, fumaric acid, benzenesulfonic acid and p-toluenesulfonic acid).

In the present invention, the compounds of the present invention represented by the formula (I) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —OCO(t-Bu), —$OCOC_{15}H_{31}$, —$OCO(m-CO_2Na-Ph)$, —$OCOCH_2CH_2CO_2Na$, —$OCOCH(NH_2)CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_2OCH_3$, —$NHCOCH(NH_2)CH_3$ and the like. When the compound of the present invention has a carboxyl group, carboxylic acid esters with aliphatic alcohols or carboxylic acid esters obtained by the reaction with an alcoholic free hydroxyl group of 1,2- or 1,3-digylcerides may, for example, be mentioned as prodrugs. Particularly preferred prodrugs are methyl esters and ethyl esters.

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

In the Examples, LC/MS means liquid chromatography-mass spectrography, (v/v) means (volume/volume), THF means tetrahydrofuran, and DMSO means dimethyl sulfoxide. LC/MS was measured under the following conditions.
Column: Waters ACQUITY UPLC BEH C18 1.7 μm, 2.1×50 mm Column
Eluent: 0.1 v/v % aqueous formic acid/0.1 v/v % formic acid in acetonitrile=(90/10→10/90)
Flow rate: 0.4 ml/min (Fixed)

Reference Synthetic Example 1

Synthesis of AD13-06
1) Synthesis of AD 13-03
1.0 g (5 mmol) of 4-cyanobenzenesulfonyl chloride AD13-01 in 25 mL of methylene chloride was mixed with 595 μL (6 mmol) of 2-(2-aminoethoxy)ethanol AD13-02 and 832 μL (6 mmol) of triethylamine and stirred overnight. The reaction solution was diluted with 25 mL of water and allowed to separate. The aqueous layer was extracted with 50 mL of methylene chloride. After combined with the extract, the organic layer was washed with 30 mL of 1 mol/L hydrochloric acid twice and then with 30 mL of water and with 30 mL of saturated aqueous sodium chloride, dried over anhydrous sodium sulfate and filtered. The filtrate was concentrated under reduced pressure. The resulting residue was purified by intermediate pressure silica gel chromatography (silica gel 30 g, hexane:ethyl acetate=50:50 to 0:100) to obtain 1.19 g (4.4 mmol, yield 88%) of AD13-03.
2) Synthesis of AD13-04
920 mg (3.4 mmol) of AD13-03 in 17 mL of ethanol was mixed with 3.4 mL of 28% aqueous ammonia and then with 1.7 mL of Raney Nickel in an argon atmosphere and stirred at room temperature in a hydrogen atmosphere for 20 hours. The atmosphere in the system was replaced with argon, and the reaction solution was filtered through Celite. The filter cake was washed with 100 mL of ethanol, and after combined with the washings, the filtrate was concentrated under reduced pressure to obtain AD13-04.

3) Synthesis of AD 13-05

750 mg (2.73 mmol) of AD13-04 suspended in 10 mL of tetrahydrofuran (THF) was mixed with 20 mL of saturated aqueous sodium hydrogen carbonate and 671 mg (3.28 mmol) of methyl 5-(chlorocarbonyl)thiophene-2-carboxylate (TEC) and stirred at room temperature overnight. After 40 mL of 1 mol/L hydrochloric acid was added over 5 minutes, the reaction solution was extracted with 50 mL of ethyl acetate twice. The organic layers were combined, washed with 20 mL of saturated aqueous sodium chloride, dried over anhydrous sodium sulfate and filtered. The filtrate was concentrated under reduced pressure. The resulting residue was purified by intermediate pressure silica gel chromatography (silica gel 30 g, methylene chloride:methanol=98:2 to 95:5) to obtain 806 mg (1.82 mmol, yield 67%) of AD13-05.

4) Synthesis of AD13-06

800 mg (1.8 mmol) of AD13-05 in 10 mL of ethanol was mixed with 2.5 mL of hydrazine monohydrate and stirred at 70° C. for 15 hours. The reaction solution was concentrated under reduced pressure, and the resulting residue was purified by silica gel chromatography (silica gel 60 g, methylene chloride:methanol=98:2 to 90:10), washed by suspending in 10 ml of ethyl acetate and dried under reduced pressure to obtain 453 mg (1.0 mmol, yield 57%) of AD13-06.

Reference Synthetic Example 2

Synthesis of AD14-06

1) Synthesis of AD 14-02

15 g (100 mmol) of 4-aminomethylbenzoic acid AD14-01 suspended in 150 ml of water was mixed with 30 g of potassium carbonate, and 28 mL (120 mmol) of di-tert-butyl carbonate was added dropwise under cooling with ice. The reaction solution was stirred at 40° C. for 3 hours and at room temperature overnight. After addition of 50 mL of water and 40 g of citric acid, the precipitated crystals were collected by filtration, washed with 50 mL of water and dried under reduced pressure to obtain 29.71 g (calculated) of crude AD14-02.

2) Synthesis of AD14-03

1.0 g (4.0 mmol) of AD14-02 suspended in 20 mL of methylene chloride (for peptide synthesis) was stirred at room temperature with 800 mg (5.0 mmol) of carbonylbisimidazole (CDI) for 40 minutes and then with 1.0 mL (10 mmol) of 2-picolylamine overnight. The reaction solution was separated between 20 mL of saturated aqueous sodium hydrogen carbonate and 30 mL of methylene chloride, and the organic layer was washed with 20 mL of saturated aqueous sodium chloride, dried over anhydrous sodium sulfate and filtered. The filtrate was concentrated under reduced pressure. The resulting residue was dissolved in 5 mL of methylene chloride and 5 mL of methanol and concentrated with 3 g of silica gel under reduced pressure. From the silica gel, 1.16 g (3.4 mmol, yield 85%) of AD14-03 was purified by silica gel column chromatography (silica gel 20 g, methylene chloride:methanol=100:0 to 10:1).

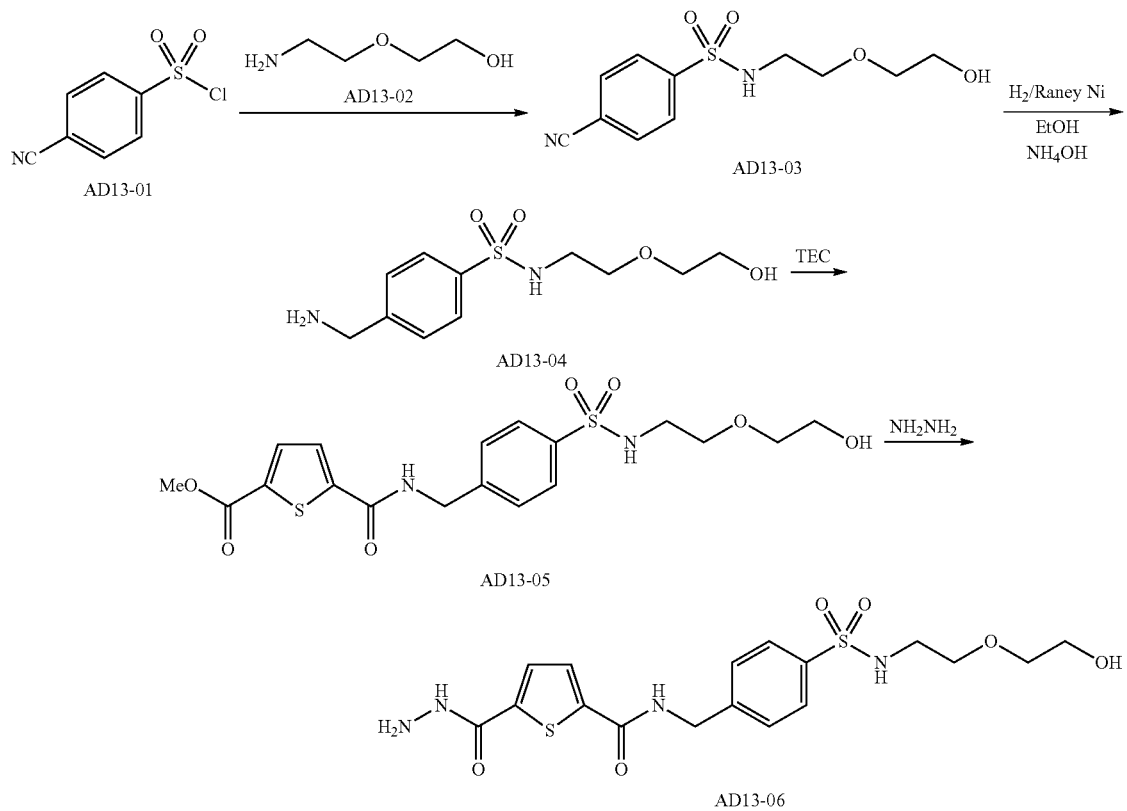

3) Synthesis of AD14-05

1.16 g (3.4 mmol) of AD14-03 in 20 mL of 1,4-dioxane was stirred with 20 mL of 4

M hydrochloric acid/1,4-dioxane at room temperature for 17 hours and concentrated under reduced pressure to obtain AD14-04. AD14-04 was mixed with 20 mL of saturated aqueous sodium hydrogen carbonate and 20 mL of tetrahydrofuran (THF) and stirred with 690 mg (3.4 mmol) of methyl 5-(chlorocarbonyl)thiophene-2-carboxylate (TEC) at room temperature for 18 hours. The precipitated crystals were collected by filtration, washed with 50 mL of water and dried under reduced pressure to obtain 850 mg (2.1 mmol, yield 62%) of AD14-05.

4) Synthesis of AD14-06

730 mg (1.8 mmol) of AD14-05 in 15 mL of ethanol was mixed with 2.0 mL of hydrazine monohydrate and stirred at 80° C. overnight. The resulting crystals were collected by filtration, washed with 40 mL of ethanol and dried under reduced pressure. The crystals were washed by suspending in 10 mL of water and dried under reduced pressure to obtain 545 mg (1.3 mmol, yield 72%) of AD14-06.

separated between 20 mL of saturated aqueous sodium hydrogen carbonate and 30 mL of methylene chloride, and the organic layer was washed with 20 mL of saturated aqueous sodium chloride, dried over anhydrous sodium sulfate and filtered. The filtrate was concentrated under reduced pressure. The resulting residue was dissolved in 5 mL of methylene chloride and 5 mL of methanol and concentrated with 3 g of silica gel under reduced pressure. From the silica gel, 1.05 g (3.2 mmol, yield 80%) of AD15-01 was purified by silica gel column chromatography (silica gel 20 g, methylene chloride:methanol=100:0 to 10:1).

2) Synthesis of AD15-03

1.05 g (3.2 mmol) of AD15-01 in 20 mL of 1,4-dioxane was stirred with 20 mL of 4 M hydrochloric acid/1,4-dioxane for 17 hours and concentrated under reduced pressure to obtain AD15-02. AD15-02 was mixed with 20 mL of saturated aqueous sodium hydrogen carbonate and 20 mL of tetrahydrofuran (THF) and stirred with 650 mg (3.2 mmol) of methyl 5-(chlorocarbonyl)thiophene-2-carboxylate (TEC) at room temperature for 18 hours. The precipitated crystals were collected by filtration, washed with 50 mL of water and dried under reduced pressure to obtain 960 mg (2.4 mmol, yield 75%) of AD15-03.

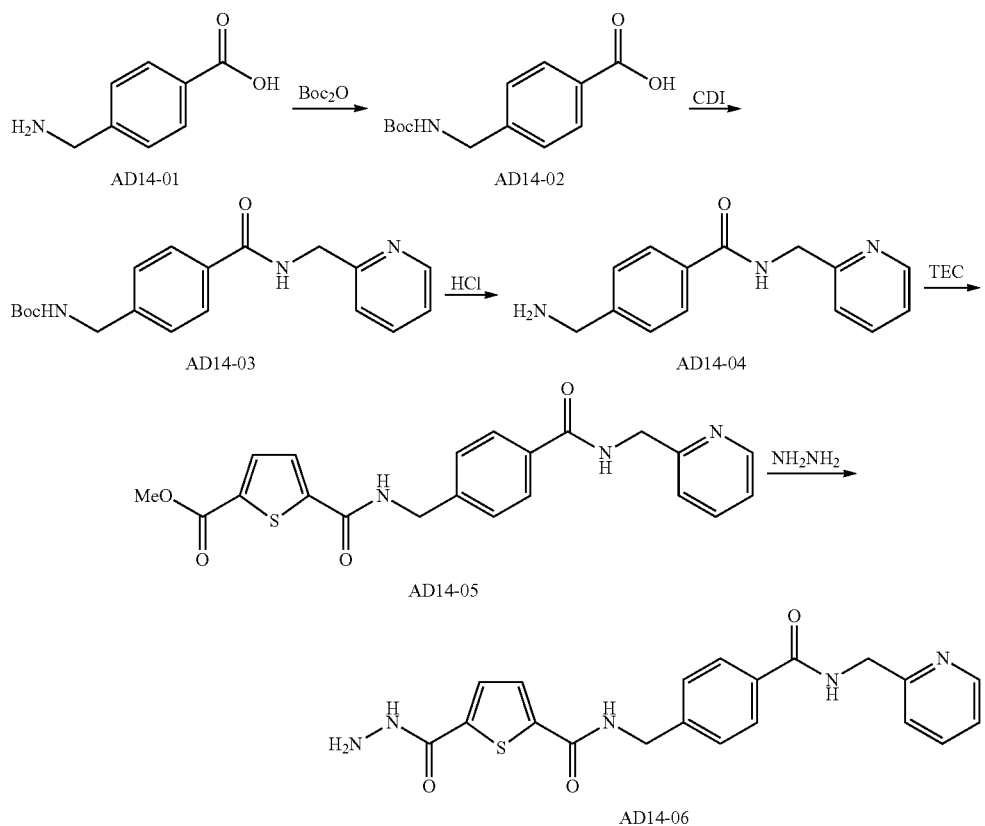

Reference Synthetic Example 3

Synthesis of AD15-04

1) Synthesis of AD 15-01

1.0 g (4.0 mmol) of AD14-02 suspended in 20 mL of methylene chloride (for peptide synthesis) was stirred at room temperature with 800 mg (5.0 mmol) of carbonylbisimidazole (CDI) for 40 minutes and then with 920 μL (10 mmol) of furfurylamine overnight. The reaction solution was 3) Synthesis of AD15-04

840 mg (2.1 mmol) of AD15-03 in 15 mL of ethanol was mixed with 2.0 mL of hydrazine monohydrate and stirred at 80° C. for two nights. The resulting crystals were collected by filtration, washed with 40 mL of ethanol and dried under reduced pressure. The crystals were washed by suspending in 10 mL of water and dried under reduced pressure to obtain 644 mg (1.6 mmol, yield 76%) of AD15-04.

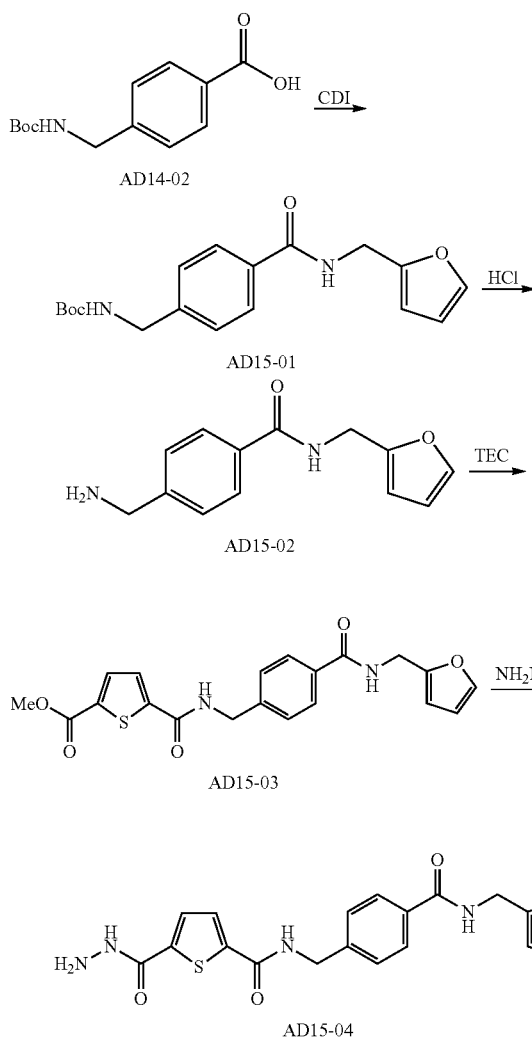

Reference Synthetic Example 4

Synthesis of AD16-04
1) Synthesis of AD16-01
1.0 g (4.0 mmol) of AD14-02 suspended in 20 mL of methylene chloride (for peptide synthesis) was stirred at room temperature with 800 mg (5.0 mmol) of carbonylbisimidazole (CDI) for 40 minutes and then with 1.0 mL (10 mmol) of tetrahydrofurfurylamine overnight. The reaction solution was separated between 20 mL of saturated aqueous sodium hydrogen carbonate and 30 mL of methylene chloride, and the organic layer was washed with 20 mL of saturated aqueous sodium chloride, dried over anhydrous sodium sulfate and filtered. The filtrate was concentrated under reduced pressure. The resulting residue was dissolved in 5 mL of methylene chloride and 5 mL of methanol and concentrated with 3 g of silica gel under reduced pressure. From the silica gel, 1.09 g (3.3 mmol, yield 86%) of AD16-01 was purified by silica gel column chromatography (silica gel 20 g, methylene chloride:methanol=100:0 to 10:1).

2) Synthesis of AD16-03
1.0 g (3.0 mmol) of AD16-01 in 20 mL of 1,4-dioxane was stirred with 20 mL of 4 M hydrochloric acid/1,4-dioxane for 17 hours and concentrated under reduced pressure to obtain AD16-02. AD16-02 was mixed with 20 mL of saturated aqueous sodium hydrogen carbonate and 20 mL of tetrahydrofuran (THF) and stirred with 610 mg (3.0 mmol) of methyl 5-(chlorocarbonyl)thiophene-2-carboxylate (TEC) at room temperature for 18 hours. The precipitated crystals were collected by filtration, washed with 50 mL of water and dried under reduced pressure to obtain 807 mg (2.0 mmol, yield 67%) of AD 16-03.

3) Synthesis of AD16-04
680 mg (1.7 mmol) of AD16-03 in 15 mL of ethanol was mixed with 2.0 mL of hydrazine monohydrate and stirred at 80° C. for two nights. The resulting crystals were collected by filtration, washed with 40 mL of ethanol and dried under reduced pressure to obtain 425 mg (1.1 mmol, yield 65%) of AD16-04.

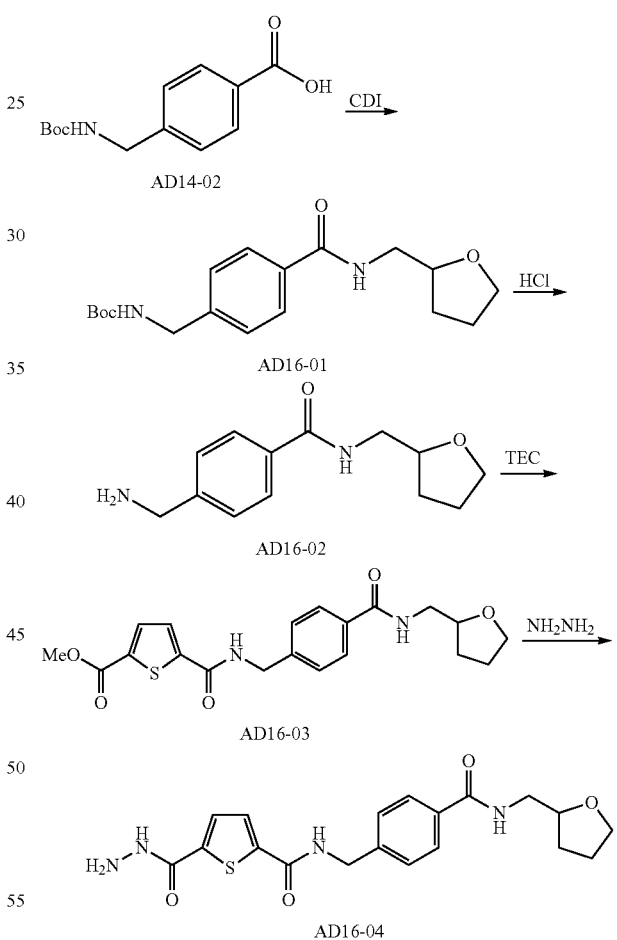

Reference Synthetic Example 5

Synthesis of AD17-04
1) Synthesis of AD17-01
2.0 g (8.0 mmol) of AD14-02 suspended in 40 mL of methylene chloride was stirred with 1.6 g (10 mmol) of carbonylbisimidazole (CDI) at room temperature for 1 hour. The reaction solution was stirred with 1.8 mL (30 mmol) of 2-aminoethanol overnight, and after addition of 40 mL of saturated aqueous sodium hydrogen carbonate, 20 mL of water and 200 mL of methylene chloride, was allowed to separate, and the organic layer was washed with 40 mL of 2 mol/L hydrochloric acid, 40 mL of saturated aqueous sodium hydrogen carbonate and 20 mL of saturated aqueous sodium chloride, dried over anhydrous sodium sulfate and filtered. The filtrate was concentrated under reduced pressure. Separately, the aqueous layer was extracted with 200 mL of ethyl acetate, and the extract was washed, dried and concentrated similarly. The residues were combined and dissolved in 5 mL of methylene chloride and 5 mL of methanol and concentrated with 3 g of silica gel under reduced pressure. From the silica gel, 1.67 g (5.7 mmol, yield 71%) of AD17-01 was purified by column chromatography (silica gel 50 g, methylene chloride:methanol=1:0 to 10:1).

2) Synthesis of AD17-03

1.67 g (5.67 mmol) of AD17-01 in 20 mL of 1,4-dioxane was stirred with 20 mL of 4 M hydrochloric acid/1,4-dioxane overnight and concentrated under reduced pressure to obtain AD17-02 hydrochloride.

AD17-02 hydrochloride was mixed with 50 mL of saturated aqueous sodium hydrogen carbonate, 50 mL of tetrahydrofuran (THF) and 1.16 g (5.67 mmol) of methyl 5-(chlorocarbonyl)thiophene-2-carboxylate (TEC) and stirred at room temperature for 24 hours. 100 mL of water was added to the reaction solution, and the precipitated crystals were collected by filtration, washed with 50 mL of water and dried under reduced pressure to obtain 1.37 g (3.8 mmol, overall yield over two steps 67%) of AD 17-03.

3) Synthesis of AD17-04

1.35 g (3.7 mmol) of AD17-03 in 30 mL of ethanol was mixed with 4 mL (80 mmol) of hydrazine monohydrate at room temperature and stirred at 80° C. overnight. The reaction solution was cooled with ice, and tie precipitated crystals were collected by filtration and washed with 40 mL of ethanol The crystals were washed by suspending in 20 mL of water and dried under reduced pressure. The reaction and the workout were repeated three times (four times in total) to 1.11 g (3.1 mmol, yield 84%) of AD17-04.

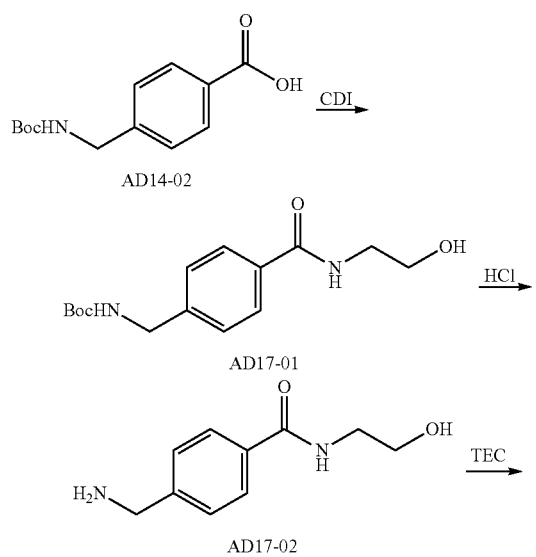

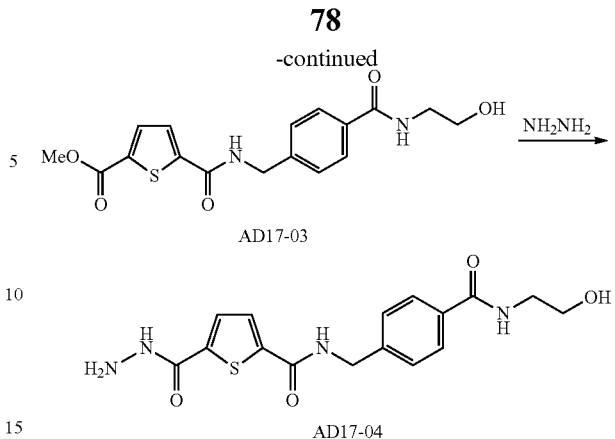

Reference Synthetic Example 6

Synthesis of AD20-04

1) Synthesis of AD20-01

1.0 g (4.0 mmol) of AD14-02 suspended in 20 mL of methylene chloride (for peptide synthesis) was stirred at room temperature with 800 mg (5.0 mmol) of carbonylbisimidazole (CDI) for 40 minutes and then with 1.6 mL (10 mmol) of 1-[2-(2-hydroxyethoxy)ethyl]piperazine overnight. The reaction solution was separated between 20 mL of saturated aqueous sodium hydrogen carbonate and 30 mL of methylene chloride, and the organic layer was washed with 20 mL of saturated aqueous sodium chloride, dried over anhydrous sodium sulfate and filtered. The filtrate was concentrated under reduced pressure. The resulting residue was dissolved in 5 mL of methylene chloride and 5 mL of methanol and concentrated with 3 g of silica gel under reduced pressure. From the silica gel, 947 mg (2.3 mmol, yield 58%) of AD20-01 was purified by silica gel column chromatography (silica gel 20 g, methylene chloride:methanol=100:0 to 10:1).

2) Synthesis of AD-20-03

940 mg (2.31 mmol) of AD20-01 in 20 mL of 1,4-dioxane was stirred with 20 mL of 4 M hydrochloric acid/1,4-dioxane at room temperature for 19 hours and concentrated under reduced pressure to obtain AD20-02. AD20-02 was mixed with 20 mL of saturated aqueous sodium hydrogen carbonate and 20 mL of tetrahydrofuran (THF) and then with 460 mg (2.31 mmol) of methyl 5-(chlorocarbonyl)thiophene-2-carboxylate (TEC) and stirred at room temperature overnight. After addition of 50 mL of water, the precipitated crystals were collected by filtration, washed with 20 mL of water, dried under reduced pressure and purified by silica gel column chromatography (silica gel 10 g, methylene chloride:methanol=100:0 to 10:1) to obtain 352 mg (0.74 mmol, yield 32%) of AD20-03.

3) Synthesis of AD20-04

850 mg (1.8 mmol) of AD20-03 in 15 mL of ethanol was mixed with 2.0 mL of hydrazine monohydrate and stirred at 80° C. for three nights. The reaction solution was concentrated under reduced pressure, and silica gel was added. From the silica gel, 585 mg (1.2 mmol, yield 68%) of AD20-04 was purified by silica gel column chromatography (silica gel 20 g, methylene chloride:methanol:ammonia=10:1:0 to 10:2:0.2).

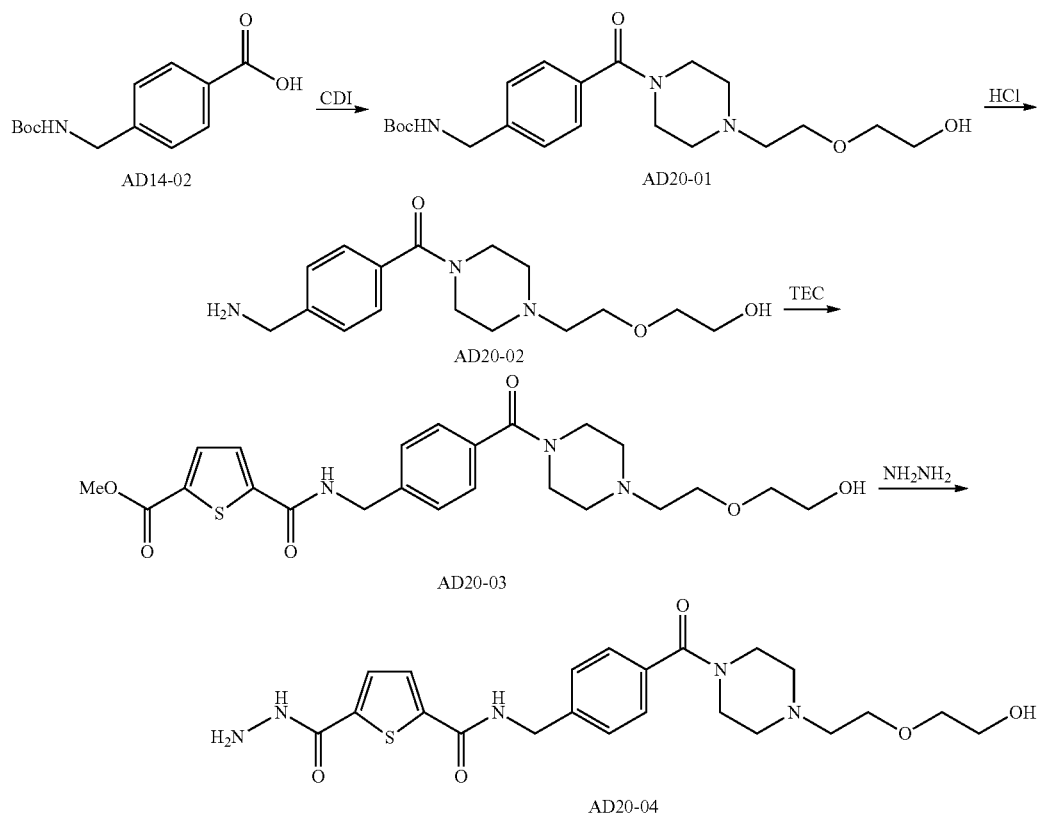

Reference Synthetic Example 7

Synthesis of AD21-04

1) Synthesis of AD21-01

1.0 g (4.0 mmol) of AD14-02 suspended in 20 mL of methylene chloride (for peptide synthesis) was stirred at room temperature with 800 mg (5.0 mmol) of carbonylbisimidazole (CDI) for 40 minutes and then with 1.3 mL (10 mmol) of N-(2-aminoethyl)morpholine overnight. The reaction solution was separated between 20 mL of saturated aqueous sodium hydrogen carbonate and 30 mL of methylene chloride, and the organic layer was washed with 20 mL of saturated aqueous sodium chloride, dried over anhydrous sodium sulfate and filtered. The filtrate was concentrated under reduced pressure. The resulting residue was dissolved in 5 mL of methylene chloride and 5 mL of methanol and concentrated with 3 g of silica gel under reduced pressure. From the silica gel, 1.05 mg (2.9 mmol, yield 73%) of AD21-01 was purified by silica gel column chromatography (silica gel 20 g, methylene chloride:methanol=100:0 to 10:1).

2) Synthesis of AD21-03

1.0 g (2.75 mmol) of AD21-01 in 20 mL of 1,4-dioxane was stirred with 20 mL of 4 M hydrochloric acid/1,4-dioxane at room temperature for 19 hours and concentrated under reduced pressure to obtain AD21-02. AD21-02 was mixed with 20 mL of saturated aqueous sodium hydrogen carbonate and 20 mL of tetrahydrofuran (THF) and stirred with 560 mg (2.0 mmol) of methyl 5-(chlorocarbonyl)thiophene-2-carboxylate (TEC) at room temperature overnight. After addition of 50 mL of water, the precipitated crystals were collected by filtration, washed with 20 mL of water and dried under reduced pressure to obtain 843 mg (2.0 mmol, yield 73%) of AD21-03.

3) Synthesis of AD21-04

827 mg (1.9 mmol) of AD21-03 in 15 mL of ethanol was mixed with 2.0 mL of hydrazine monohydrate and stirred at 80° C. for two nights. The resulting crystals were collected by filtration, washed with 40 mL of ethanol and dried under reduced pressure. The crystals were washed by suspending in 10 mL of water and dried under reduced pressure to obtain 429 mg (1.0 mmol, yield 53%) of AD21-04.

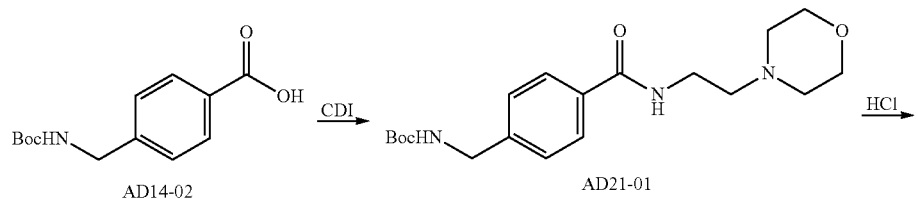

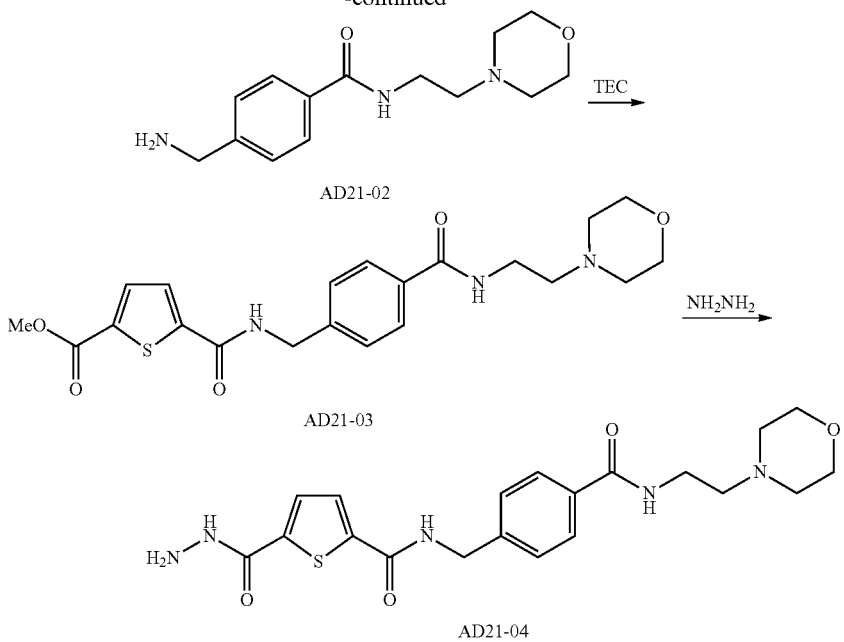

Reference Synthetic Example 8

Synthesis of AD22-04
1) Synthesis of AD22-01

600 mg (4.0 mmol) of N,N-bis(2-hydroxyethyl)ethylenediamine in 50 mL of DMF was stirred with 1.0 g (4.0 mmol) of AD14-02 and 1.25 g (4.0 mmol) of 4-(4,6-dimethoxy-1,3,5-triazin-2-yl)-4-methylmorpholinium chloride (DMT-MM) at room temperature for 16 hours and concentrated under reduced pressure. The resulting residue was dissolved in 5 mL of methanol and concentrated with 5 g of silica gel under reduced pressure. From the silica gel, 732 mg (1.9 mmol, yield 48%) of AD22-01 was purified by silica gel column chromatography (silica gel 50 g, methylene chloride:methanol=100:0 to 2:1).

2) Synthesis of AD22-03

630 mg (1.6 mmol) of AD22-01 was stirred with 15 mL of trifluoroacetic acid at room temperature for 1 hour and concentrated under reduced pressure. The resulting residue was dissolved in 5 mL of methanol and concentrated with 3 g of silica gel under reduced pressure. From the silica gel, 565 mg of AD22-02 was purified by silica gel column chromatography (silica gel 20 g, methylene chloride:methanol=1:1). AD22-02 was dissolved in 20 mL of DMF, stirred with 573 mg (2.0 mmol) of separately synthesized AD18-03 and 628 mg (2.0 mmol) of 4-(4,6-dimethoxy-1,3,5-triazin-2-yl)-4-methylmorpholinium chloride (DMT-MM) at room temperature overnight and concentrated under reduced pressure. The resulting residue was dissolved in 5 mL of methylene chloride and 5 mL of methanol and concentrated with 5 g of silica gel under reduced pressure. From the silica gel, 595 mg (1.1 mmol, overall yield over two steps 69%) of AD22-03 was purified by silica gel column chromatography (silica gel 50 g, methylene chloride:methanol=1:1).

3) Synthesis of AD22-04

360 mg (0.7 mmol) of AD22-03 was stirred with 3 mL of trifluoroacetic acid at room temperature for 2 hours and concentrated under reduced pressure. The resulting residue was dissolved in 10 mL of methanol and concentrated with 1 g of silica gel under reduced pressure. From the silica gel, 234 mg (0.5 mmol, yield 74%) of AD22-04 was purified by silica gel column chromatography (silica gel 20 g, methylene chloride:methanol=1:1).

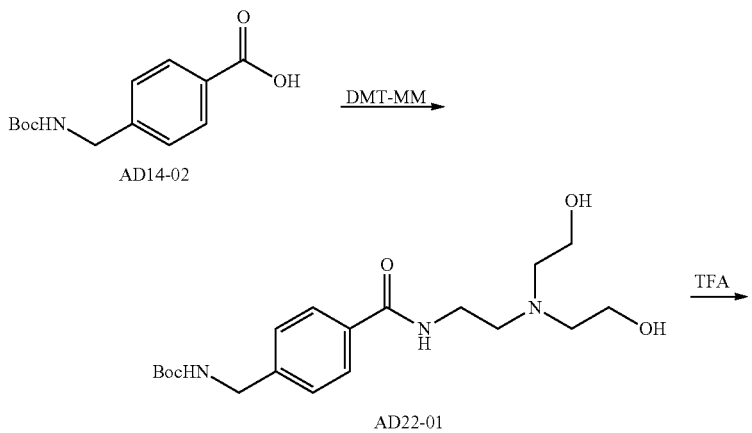

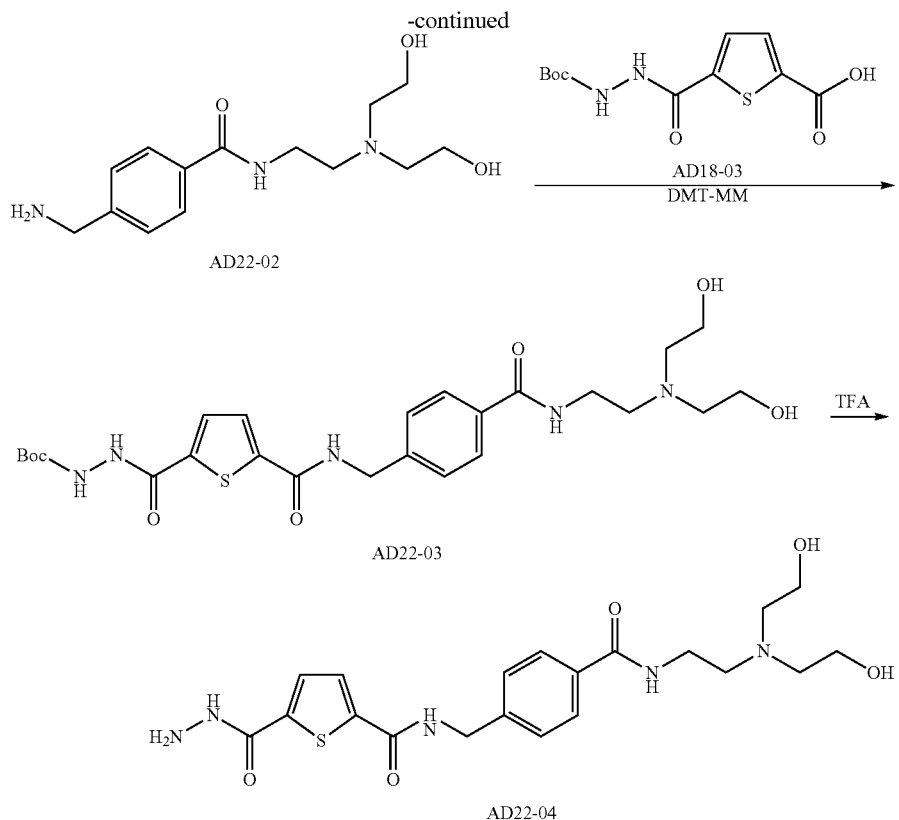

Reference Synthetic Example 9

Synthesis of AD23-04

1) Synthesis of AD23-01

5.0 g (17.5 mmol) of AD18-04 was heated with 50 mL of thionyl chloride for 1 hour with reflux, and the reaction solution was concentrated under reduced pressure. The resulting acid chloride was used directly in the subsequent reaction. 3.4 g (15 mmol) of tert-butyl 4-(2-aminoethyl)tetrahydro-1(2H)-pyrazinecarboxylate in 100 mL of methylene chloride was stirred with 100 mL of water, 2 g of sodium hydrogen carbonate and the acid chloride at room temperature for 1 day. After addition of 100 mL of methylene chloride, the reaction solution was allowed to separate, and the organic layer was dried over anhydrous sodium sulfate and filtered. The filter cake was mixed with 10 g of silica gel, and from the silica gel mixture, 4.24 mg (8.5 mmol, yield 49%) of AD23-01 was purified by column chromatography (silica gel 125 g, methylene chloride:methanol=1:0 to 5:1).

2) Synthesis of AD23-02

4.24 g (8.5 mmol) of AD23-01 in 100 mL of methanol was mixed with 2.0 g of 10% palladium on carbon (50% wet) in an argon atmosphere and stirred in a hydrogen atmosphere overnight. The atmosphere in the system was replaced with argon, and the reaction solution was filtered. The filter cake was washed with 100 mL of methanol, and after combined with the washings, the filtrate was concentrated under reduced pressure. The residue was purified by column chromatography (silica gel 50 g, methylene chloride:methanol=1:0 to 20:1) to obtain 2.71 g (7.5 mmol, yield 88%) of AD23-02.

3) Synthesis of AD23-03

AD23-02 suspended in 50 mL of tetrahydrofuran (THF) was mixed with 50 mL of saturated aqueous sodium hydrogen carbonate and 1.84 g (9 mmol) of methyl 5-(chlorocarbonyl)thiophene-2-carboxylate (TEC) and stirred overnight. After addition of 100 mL of water, the precipitated crystals were collected by filtration, washed with 100 mL of water and dried under reduced pressure to obtain 3.02 g (5.7 mmol, yield 76%) of AD23-03.

4) Synthesis of AD23-04

1 g (1.9 mmol) of AD23-03 in 20 mL of ethanol was mixed with 2 mL of hydrazine monohydrate at room temperature and stirred at 70° C. for 20 hours. The reaction solution was cooled with ice, and the precipitated crystals were collected by filtration, washed with 20 mL of ethanol and with 30 mL of water and dried under reduced pressure to obtain 540 mg (1.0 mmol, yield 53%) of AD23-04.

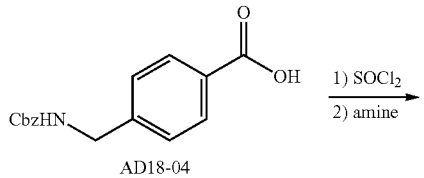

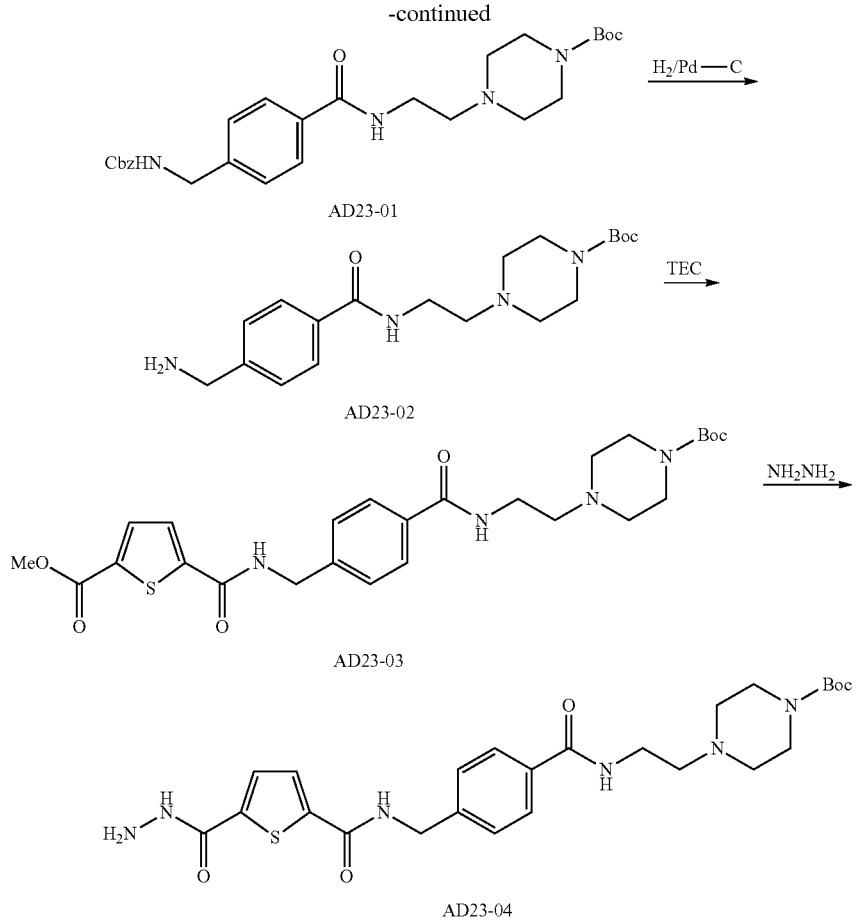

Reference Synthetic Example 10

Synthesis of AD24-01

597 mg (1.1 mmol) of AD23-04 synthesized in Reference Synthetic Example 9 was stirred with 10 mL of trifluoroacetic acid at room temperature for 1 hour. The reaction solution was bubbled with argon gas and concentrated under reduced pressure. The resulting residue was boiled with 10 mL of methanol three times. The resulting residue was mixed with 3 g of silica gel and purified by column chromatography (silica gel 20 g, methylene chloride:methanol=1:1), and the eluate was washed by suspending in 20 mL of ethylene chloride and dried under reduced pressure to obtain 450 mg (1.0 mmol, yield 91%) of AD24-01.

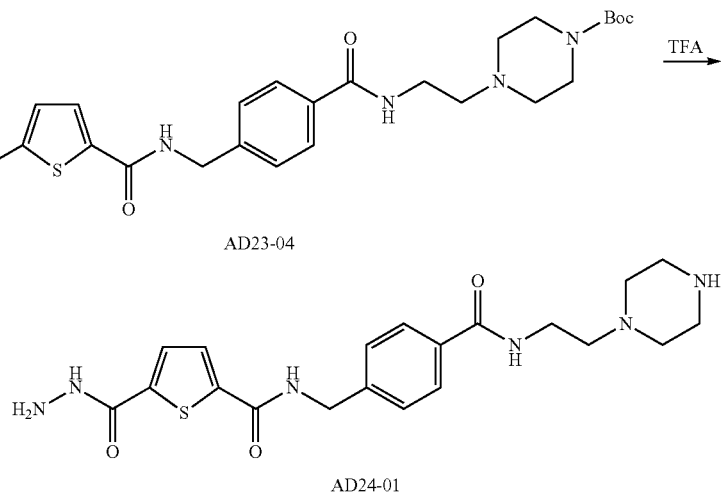

Reference Synthetic Example 11

Synthesis of AD25-08
1) Synthesis of AD25-02

11.8 g of (100 mmol) of diethylene glycol monomethyl ether (AD25-01) in 100 mL of methylene chloride was stirred with 20 mL (250 mmol) of pyridine and 24 g of (125 mmol) of p-toluenesulfonyl chloride at room temperature for 3 hours. The reaction solution was diluted with 30 mL of methylene chloride, washed with 200 mL of water and 200 mL of saturated aqueous sodium chloride, dried over anhydrous sodium sulfate and filtered. The filtrate was concentrated under reduced pressure, and the resulting residue was purified by silica gel chromatography (silica gel 300 g, hexane:ethyl acetate=3:1 to 2:1) to obtain 22.8 g of (82.8 mmol, yield 83%) of AD25-02.

2) Synthesis of AD25-03

22.8 g of (82.8 mmol) of AD25-02 in 150 mL of DMF was stirred with 6.5 g of sodium azide at 50° C. for 23 hours. The reaction solution was allowed to cool and separated between 300 mL of water and 150 mL of ethyl acetate. The aqueous layer was extracted with 150 mL of ethyl acetate twice, and after combined with the extracts, the organic layer was washed with 100 mL of water three times and then with 100 mL of saturated aqueous sodium chloride, dried over anhydrous sodium sulfate and filtered. The filtrate was concentrated under reduced pressure to obtain 9.33 g of (64 mmol, yield 78%) of AD25-03.

3) Synthesis of AD25-04

1.0 g of (6.9 mmol) of AD25-03 in 60 mL of tetrahydrofuran (THF) was heated with 0.5 mL of water and 9 g (10 mmol) of triphenylphosphine polystyrene for 2.5 hours with reflux. The reaction solution was allowed to cool, and the resin was filtered off and washed with 100 mL of ethyl acetate. After combined with the washings, the filtrate was concentrated under reduced pressure to obtain 896 mg of AD25-04.

4) Synthesis of AD25-05

896 mg of AD25-04 in 35 mL of methylene chloride was stirred with 2.08 g (8.28 mmol) of separately synthesized AD14-02 and 1.59 g (8.28 mmol) of 1-ethyl-3-(3-dimethylaminopropyl)carbodiimide hydrochloride (EDCI) at room temperature for 5 hours. The reaction solution was diluted with 70 mL of methylene chloride, washed with 20 mL of 1 mol/L hydrochloric acid, 20 mL of water, 20 mL of saturated aqueous sodium hydrogen carbonate, 20 mL of water and 20 mL of saturated aqueous sodium chloride, dried over anhydrous sodium sulfate and filtered, and the filtrate was concentrated under reduced pressure. The resulting residue was purified by intermediate pressure silica gel chromatography (silica gel 100 g, hexane:ethyl acetate=50:50 to 0:100) to obtain 1.33 g (3.8 mmol, overall yield over two steps 55%) of AD25-05.

5) Synthesis of AD25-06

1.33 g (3.8 mmol) of AD25-05 in 10 mL of 1,4-dioxane was stirred with 20 mL of 4 M hydrochloric acid/1,4-dioxane at room temperature overnight. The reaction solution was concentrated under reduced pressure to obtain AD25-06.

6) Synthesis of AD25-07

AD25-06 suspended in 18 mL of tetrahydrofuran (THF) was mixed with 72 mL of saturated aqueous sodium hydrogen carbonate and 1.13 g (5.5 mmol) of methyl 5-(chlorocarbonyl)thiophene-2-carboxylate (TEC) and stirred overnight. 100 mL of water was added to the reaction solution, and the precipitated crystals were collected by filtration, washed with 100 mL of water and dried under reduced pressure to obtain 1.28 g (3.06 mmol, overall yield over two steps 81%) of AD25-07.

7) Synthesis of AD25-08

420 mg (1 mmol) of AD25-07 in 5 mL of ethanol was mixed with 1 mL of hydrazine monohydrate at room temperature and stirred at 70° C. for 15 hours. The reaction solution was concentrated under reduced pressure, and 20 mL of water was added. The precipitated crystals were collected by filtration, washed with 30 mL of water and dried under reduced pressure to obtain 316 mg (0.75 mmol, yield 75%) of AD25-08.

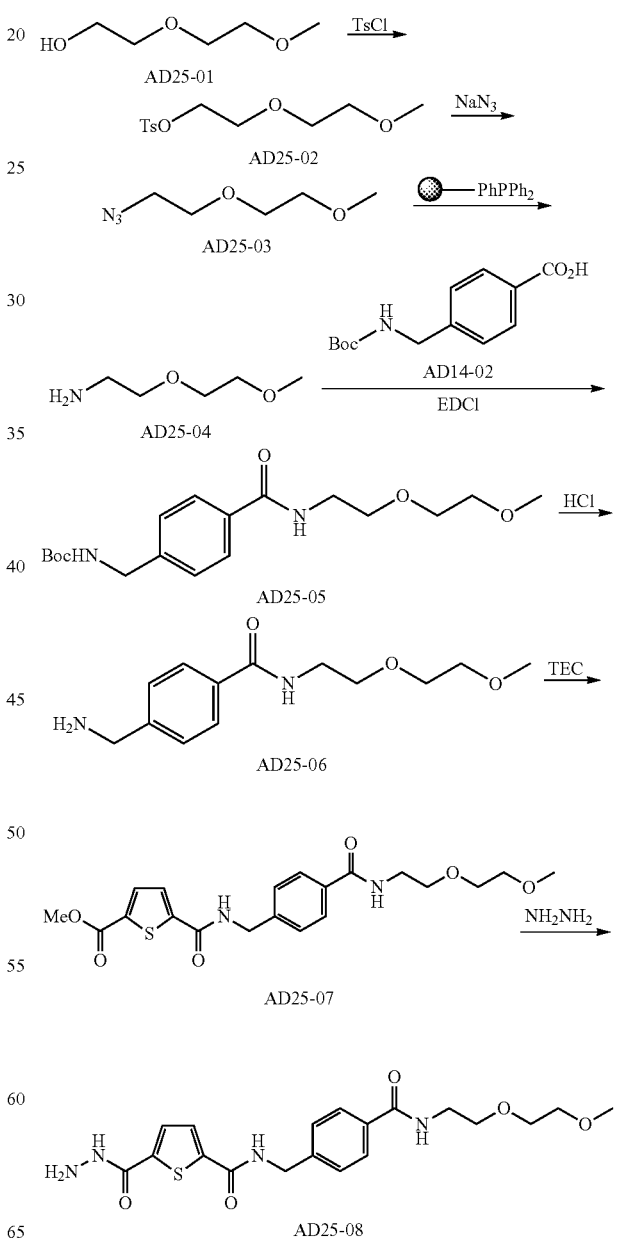

Reference Synthetic Example 12

Synthesis of AD26-08
1) Synthesis of AD26-02
3.4 g (20 mmol) of diethylene glycol monobutyl ether (AD26-01) in 20 mL of methylene chloride was stirred with 4 mL (50 mmol) of pyridine and 4.8 g (25 mmol) of p-toluenesulfonyl chloride at room temperature for 3 hours. The reaction solution was diluted with 100 mL of methylene chloride, washed with 50 mL of water and 50 mL of saturated aqueous sodium hydrogen carbonate, dried over anhydrous sodium sulfate and filtered. The filtrate was concentrated under reduced pressure, and the resulting residue was purified by silica gel column chromatography (silica gel 300 g, hexane:ethyl acetate=3:1 to 2:1) to obtain 3.61 g (11.4 mmol, yield 57%) of AD26-02.
2) Synthesis of AD26-03
3.6 g (11.4 mmol) of AD26-02 in 23 mL of DMF was stirred with 890 mg (13.7 mmol) of sodium azide at 50° C. for 1 day. The reaction solution was allowed to cool and separated between 56 mL of water and 50 mL of diethyl ether. The aqueous layer was extracted with 50 mL of diethyl ether twice, and after combined with the extracts, the organic layer was washed with 30 mL of water three times and with 30 mL of saturated aqueous sodium chloride, dried over anhydrous sodium sulfate and filtered. The filtrate was concentrated under reduced pressure to obtain 2.05 g (10.9 mmol, yield 96%) of AD26-03.
3) Synthesis of AD26-04
1.3 g (6.9 mmol) of AD26-03 in 50 mL of tetrahydrofuran (THF) was heated with 0.5 mL of water and 9 g (10 mmol) of triphenylphosphine polystyrene for 2.5 hours with reflux. The reaction solution was allowed to cool, and the resin was filtered off and washed with 100 mL of ethyl acetate. After combined with the washings, the filtrate was concentrated under reduced pressure to obtain 1.52 g of AD26-04.
4) Synthesis of AD26-05
1.52 g of AD26-04 in 35 mL of methylene chloride was stirred with 2.08 g (8.28 mmol) of separately synthesized AD14-02 and 1.59 g (8.28 mmol) of 1-ethyl-3-(3-dimethylaminopropyl)carbodiimide hydrochloride (EDCI) at room temperature for 4 hours. The reaction solution was diluted with 70 mL of methylene chloride, washed with 20 mL of 1 mol/L hydrochloric acid, 20 mL of water, 20 mL of saturated aqueous sodium hydrogen carbonate, 20 mL of water and 20 mL of saturated aqueous sodium chloride, dried over anhydrous sodium sulfate and filtered, and the filtrate was concentrated under reduced pressure. The resulting residue was purified by intermediate pressure silica gel chromatography (silica gel 100 g, hexane:ethyl acetate=60:40 to 10:90) to obtain 1.93 g (4.9 mmol, overall yield over two steps 71%) of AD26-05.
5) Synthesis of AD26-06
1.93 g (4.9 mmol) of AD26-05 in 10 mL of 1,4-dioxane was stirred with 20 mL of 4 M hydrochloric acid/1,4-dioxane at room temperature overnight. The reaction solution was concentrated under reduced pressure to obtain AD26-06.
6) Synthesis of AD26-07
AD26-06 suspended in 24 mL of tetrahydrofuran (THF) was mixed with 96 mL of saturated aqueous sodium hydrogen carbonate and 1.47 g (7.2 mmol) of methyl 5-(chlorocarbonyl)thiophene-2-carboxylate (TEC) and stirred overnight. 100 mL of water was added to the reaction solution, and the precipitated crystals were collected by filtration, washed with 100 mL of water, then washed by suspending in 50 mL of saturated aqueous sodium hydrogen carbonate and collected by filtration. The crystals were washed with 20 mL of water and dried under reduced pressure to obtain 2.13 g (4.8 mmol, overall yield over two steps 94%) of AD26-07.
7) Synthesis of AD26-08
462 mg (1.0 mmol) of AD26-07 in 5 mL of ethanol was mixed with 2 mL of hydrazine monohydrate at room temperature and stirred at 70° C. for 15 hours. The reaction solution was concentrated under reduced pressure, and 20 mL of water was added. The precipitated crystals were collected by filtration, washed with 40 mL of water and dried under reduced pressure to obtain 400 mg (0.87 mmol, yield 87%) of AD26-08.

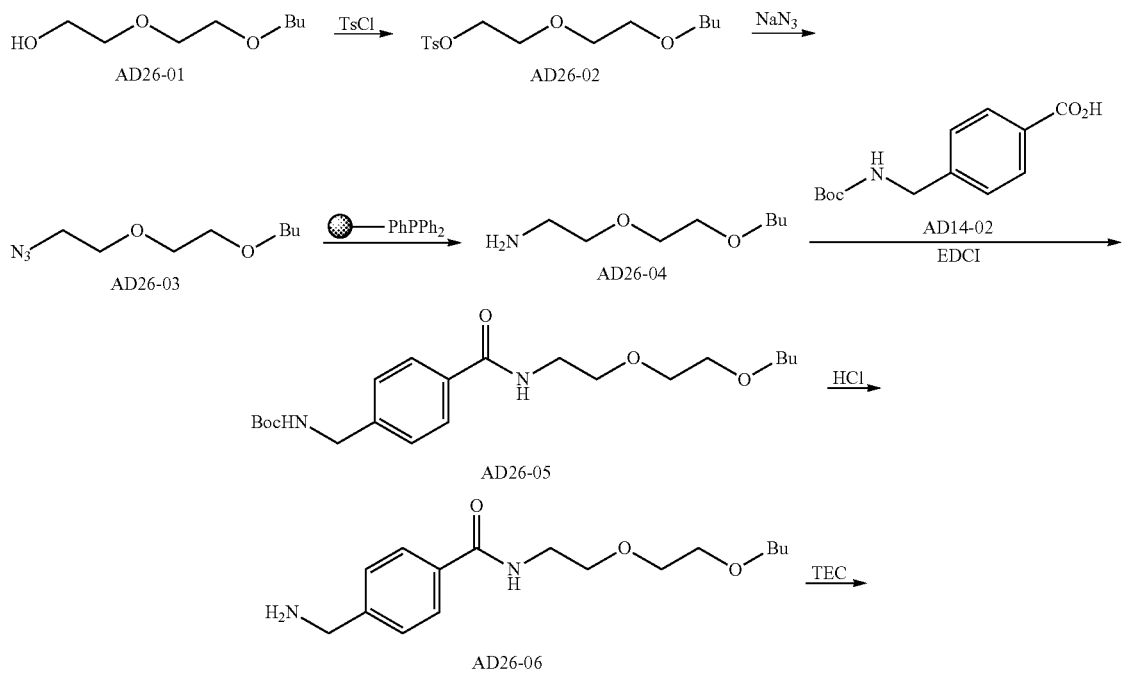

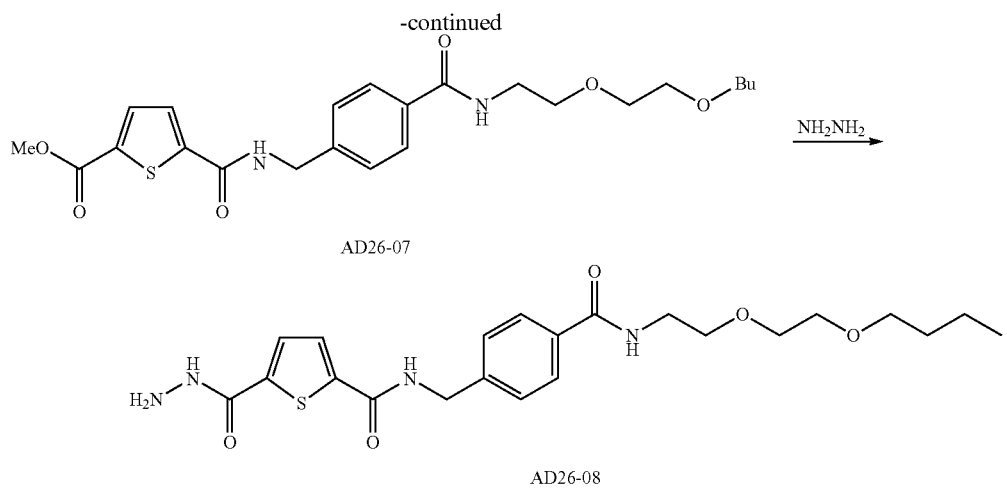

Reference Synthetic Example 13

Synthesis of AD27-08

1) Synthesis of AD27-02

4.0 g (20 mmol) of diethylene glycol monohexyl ether (AD27-01) in 20 mL of methylene chloride was stirred with 4 mL (50 mmol) of pyridine and 4.8 g (25 mmol) of p-toluenesulfonyl chloride at room temperature of 3 hours. The reaction solution was diluted with 100 mL of methylene chloride, washed with 50 mL of water and 50 mL of saturated aqueous sodium chloride, dried over anhydrous sodium sulfate and filtered. The filtrate was concentrated under reduced pressure. The resulting residue was purified by silica gel column chromatography (silica gel 150 g, hexane:ethyl acetate=9:1 to 2:1) to obtain 4.91 g (14.2 mmol, yield 71%) of AD27-02.

2) Synthesis of AD27-03

4.9 g (14.2 mmol) of AD-27-02 in 28 mL of DMF was stirred with 1.1 g (17 mmol) of sodium azide at 50° C. for 1 day. The reaction solution was allowed to cool and separated between 56 mL of water and 50 mL of diethyl ether. The aqueous layer was extracted with 50 mL of diethyl ether twice, and after combined with the extracts, the organic layer was washed with 30 mL of water three times and then with 30 mL of saturated aqueous sodium chloride, dried over anhydrous sodium sulfate and filtered. The filtrate was concentrated under reduced pressure to obtain 2.92 g (13.5 mmol, yield 96%) of AD27-03.

3) Synthesis of AD27-04

1.5 g (6.9 mmol) of AD27-03 in 50 mL of tetrahydrofuran (THF) was heated with 0.5 mL of water and 9 g (10 mmol) of triphenylphosphine polystyrene for 2.5 hours with reflux. The reaction solution was allowed to cool, and the resin was filtered off and washed with 100 mL of ethyl acetate. After combined with the washings, the filtrate was concentrated under reduced pressure to obtain 1.94 g of AD27-04.

4) Synthesis of AD27-05

1.94 g of AD27-04 in 35 mL of methylene chloride was stirred with 2.08 g (8.28 mmol) of separately synthesized AD14-02 and 1.59 g (8.28 mmol) of 1-ethyl-3-(3-dimethylaminopropyl)carbodiimide hydrochloride (EDCI) at room temperature for 4 hours. The reaction solution was diluted with 70 mL of methylene chloride, washed with 20 mL of 1 mol/L hydrochloric acid, 20 mL of water, 20 mL of saturated aqueous sodium hydrogen carbonate, 20 mL of water and 20 mL of saturated aqueous sodium chloride, dried over anhydrous sodium sulfate and filtered, and the filtrate was concentrated under reduced pressure. The resulting residue was purified by intermediate pressure silica gel chromatography (silica gel 100 g, hexane:ethyl acetate=60:40 to 10:90) to obtain 2.16 g (5.1 mmol, overall yield over two steps 74%) of AD27-05.

5) Synthesis of AD27-06

2.16 g (5.1 mmol) of AD27-05 in 10 mL of 1,4-dioxane was stirred with 20 mL of 4 M hydrochloric acid/1,4-dioxane at room temperature overnight. The reaction solution was concentrated under reduced pressure to obtain AD27-06.

6) Synthesis of AD27-07

AD27-06 suspended in 25 mL of tetrahydrofuran (THF) was mixed with 100 mL of saturated aqueous sodium hydrogen carbonate and 1.56 g (7.7 mmol) of methyl 5-(chlorocarbonyl)thiophene-2-carboxylate (TEC) and stirred overnight. 100 mL of water was added to the reaction solution, and the precipitated crystals were collected by filtration, washed with 100 mL of water, then washed by suspending in 50 mL of saturated aqueous sodium hydrogen sulfate and collected by filtration. The crystals were washed with 20 mL of water and dried under reduced pressure to obtain 1.91 g (3.9 mmol, overall yield over two steps 76%) of AD27-07.

7) Synthesis of AD27-08

490 mg (1.0 mmol) of AD27-07 in 5 mL of ethanol was mixed with 1 mL of hydrazine monohydrate and stirred at 70° C. for 15 hours. The reaction solution was allowed to cool to room temperature, and 30 mL of water was added. The precipitated crystals were collected by filtration, washed with 40 mL of water and dried under reduced pressure to obtain 400 mg (0.86 mmol, yield 86%) of AD27-08.

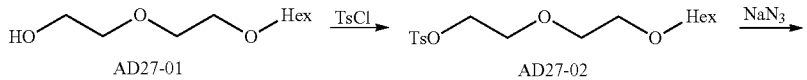

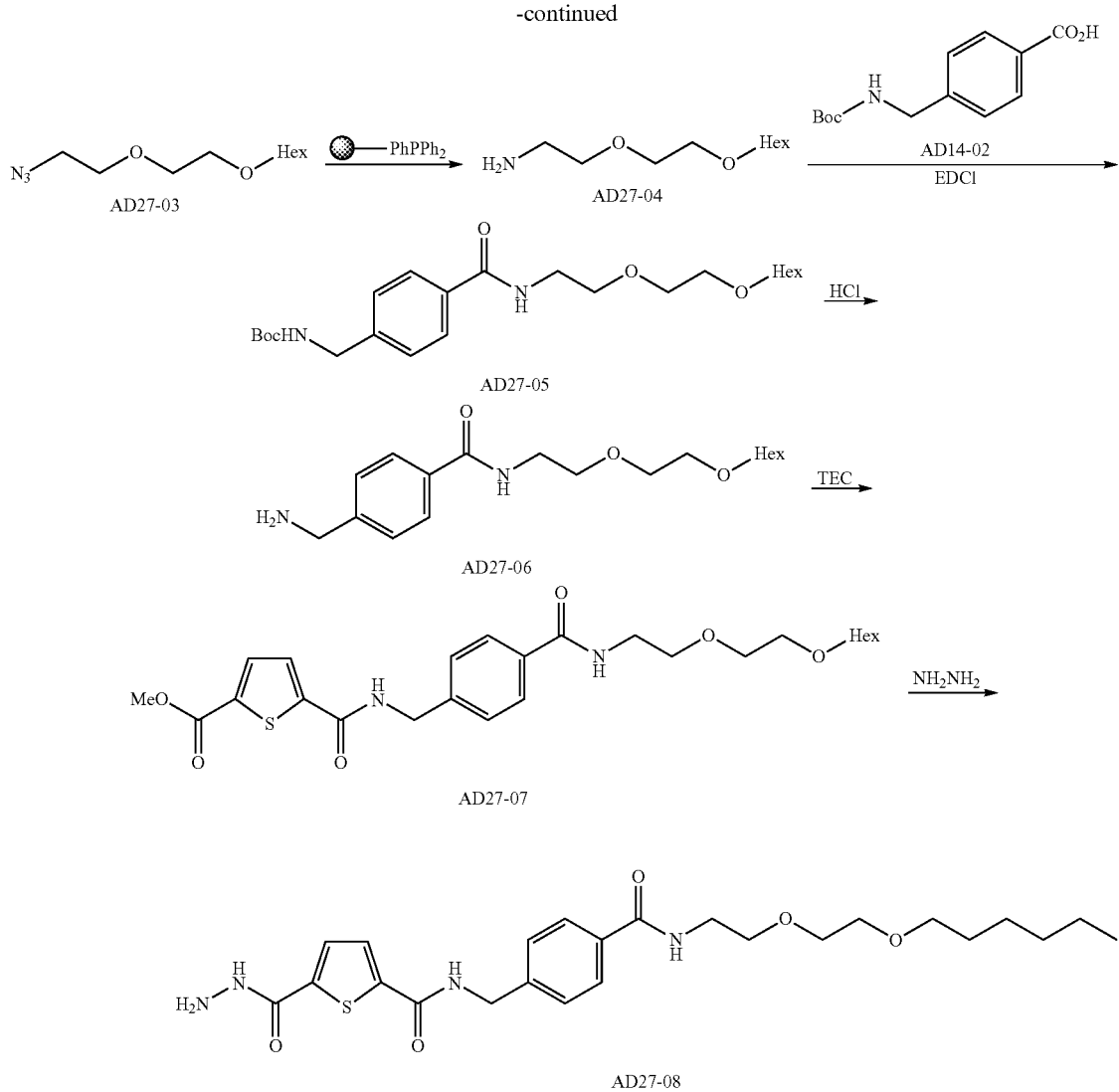

Reference Synthetic Example 14

Synthesis of AD28-05
1) Synthesis of AD28-01

6.0 g (22.8 mmol) of AD14-02 suspended in 120 mL of methylene chloride was mixed with 4.8 g (30 mmol) of carbonyldiimidazole at room temperature. The reaction solution was stirred at the same temperature of 1 hour and then with 6.0 mL (60 mmol) of 2-(2-aminoethoxy)ethanol for 1 hour and separated between 200 mL of saturated aqueous sodium hydrogen carbonate and 400 mL of ethyl acetate, and the organic layer was washed with 200 mL of saturated aqueous sodium chloride, dried over anhydrous sodium sulfate and filtered. The filtrate was concentrated under reduced pressure. The resulting residue was purified by silica gel column chromatography (silica gel 150 g, methylene chloride:methanol=1:0 to 9:1) to obtain 7.9 g (20.3 mmol, yield 89%) of AD28-01.

2) Synthesis of AD28-04

1.0 g (2.96 mmol) of AD28-01 in 20 mL of 1,4-dioxane was stirred with 20 mL of 4 M hydrochloric acid/1,4-dioxane at room temperature for 2 hours, and the reaction solution was concentrated under reduced pressure to obtain AD28-02. AD28-02 was dissolved in 20 mL of saturated aqueous sodium hydrogen carbonate and 5 mL of tetrahydrofuran (THF) and stirred with AD28-03 synthesized from monomethyl isophthalate and thionyl chloride in 15 mL of tetrahydrofuran (THF) overnight. The reaction solution was concentrated under reduced pressure and cooled with ice, and the precipitated crystals were collected by filtration and purified by silica gel column chromatography (silica gel 10 g, methylene chloride:methanol=1:0 to 10:1) to obtain 557 mg (1.4 mmol, overall yield over two steps 47%) of AD28-04.

3) Synthesis of AD28-05

557 mg (1.0 mmol) of AD28-04 in 15 mL of ethanol was mixed with 2 mL of hydrazine monohydrate at room temperature and stirred at 80° C. for 15 hours. The reaction solution was allowed to cool to room temperature and concentrated under reduced pressure. After addition of 20 mL of water, the precipitated crystals were collected by filtration, washed with 10 mL of water and dried under reduced pressure to obtain 399 mg (1.0 mmol, calculated) of AD28-05.

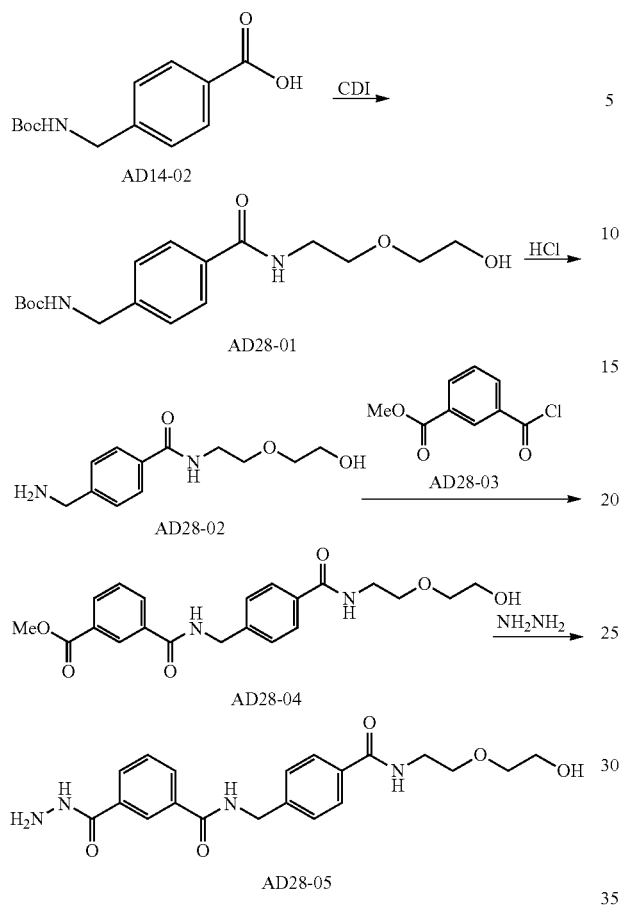

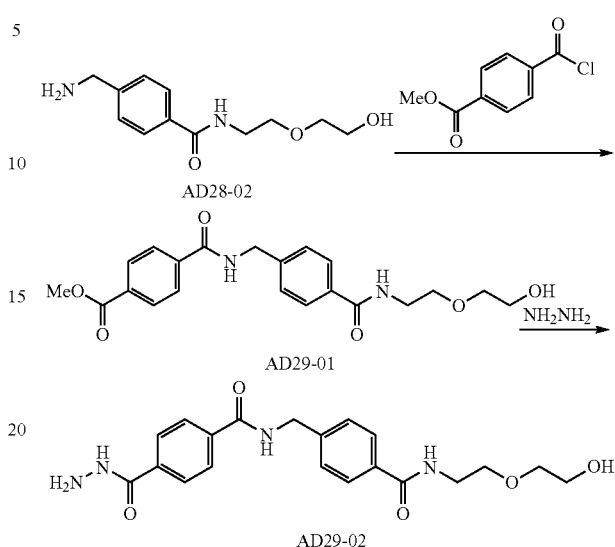

Reference Synthetic Example 15

Synthesis of AD29-02
1) Synthesis of AD29-01

AD28-02 (2.96 mmol) was dissolved in 20 mL of saturated aqueous sodium hydrogen carbonate and 20 mL of tetrahydrofuran (THF) and stirred with 590 mg (2.96 mmol) of monomethyl terephthaloyl chloride at room temperature overnight. After addition of 50 mL of water, the reaction solution was concentrated under reduced pressure. 100 mL of methylene chloride was added, and the precipitated crystals were collected by filtration and washed with 50 mL of water to obtain 620 mg (1.5 mmol, yield 51%) of AD29-01.

2) Synthesis of AD29-02

557 mg 1.0 (mmol) of AD29-01 in 15 mL of ethanol was mixed with 2 mL of hydrazine monohydrate and stirred at 80° C. for 15 hours. The reaction solution was allowed to cool to room temperature, and the precipitated crystals were collected by filtration, washed with 40 mL of ethanol and 20 mL of water and dried under reduced pressure to obtain 394 mg (1.0 mmol, calculated) of AD29-02.

Reference Synthetic Example 16

Synthesis of AD30-04
1) Synthesis of AD30-03

1.0 g (5.5 mmol) of 5-methoxycarbonyl-2-pyridinecarboxylic acid (AD30-01) (KeyOrganics) was mixed with 10 mL of thionyl chloride and stirred at an outer temperature of 110° C. for 1 hour. The reaction solution was concentrated under reduced pressure to obtain AD30-02. AD28-02 (4.44 mmol) suspended in 15 mL of tetrahydrofuran (THF) was stirred with 75 mL of saturated aqueous sodium hydrogen carbonate and AD30-02 at room temperature for 2 days. The reaction solution was concentrated under reduced pressure and separated between 50 mL of water and 100 mL of ethyl acetate, and the aqueous layer was extracted with 50 mL of ethyl acetate twice. After combined with the extracts, the organic layer was washed with 50 mL of saturated aqueous sodium hydrogen carbonate, 50 mL of water and 50 mL of saturated aqueous sodium chloride, dried over anhydrous sodium sulfate and filtered. The filtrate was concentrated under reduced pressure to obtain 997 mg (2.48 mmol, yield 45%) of AD30-03.

2) Synthesis of AD30-04

870 mg (2.2 mmol) of AD30-03 in 15 mL of ethanol was mixed with 2.0 mL of hydrazine monohydrate at room temperature and stirred at 70° C. overnight. The reaction solution was concentrated under reduced pressure, and 20 mL of water was added. The precipitated crystals were collected by filtration, washed with 20 mL of water and dried under reduced pressure to obtain 531 mg (1.32 mmol, yield 60%) of AD30-04.

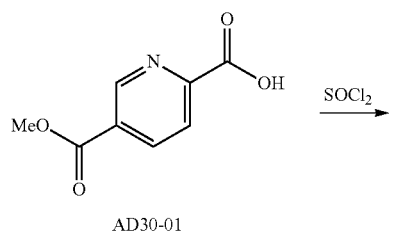

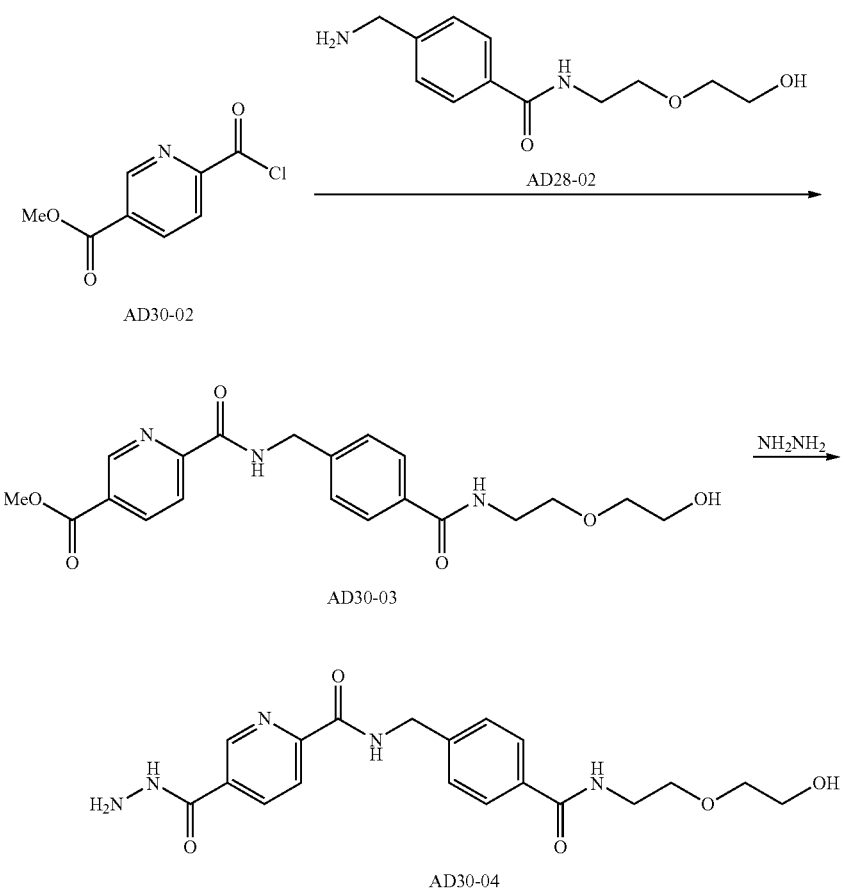

Reference Synthetic Example 17

Synthesis of AD31-02

1) Synthesis of AD31-01

AD28-02 (2.96 mmol) suspended in 15 mL of methylene chloride was mixed with 1 mL (6 mmol) of diisopropylethylamine, 536 mg (3.0 mmol) of 6-methoxycarbonyl-2-pyridinecarboxylic acid, 370 mg (4.5 mmol) of dimethylaminopyridine and 863 mg (4.5 mmol) of 1-ethyl-3-(3-dimethylaminopropyl)carbodiimide hydrochloride (EDCI) at room temperature and stirred at the same temperature. The reaction solution was diluted with 100 mL of methylene chloride, washed with 20 mL of saturated aqueous sodium hydrogen carbonate, 20 mL of water and 20 mL of saturated aqueous sodium chloride, dried over anhydrous sodium sulfate and filtered, and the filtrate was concentrated under reduced pressure. The resulting residue was purified by intermediate pressure silica gel column chromatography (silica gel 50 g, methylene chloride:methanol=99:1 to 90:10) to obtain 487 mg (1.21 mmol, yield 41%) of AD31-01.

2) Synthesis of AD31-02

430 mg 1.07 (mmol) of AD31-01 suspended in 10 mL of ethanol was mixed with 2.0 mL of hydrazine monohydrate at room temperature and stirred at 70° C. overnight. The reaction solution was concentrated under reduced pressure, and 5 mL of water was added. The precipitated crystals were collected by filtration, washed with 20 mL of water and dried under reduced pressure to obtain 379 mg (0.95 mmol, yield 61%) of AD31-02.

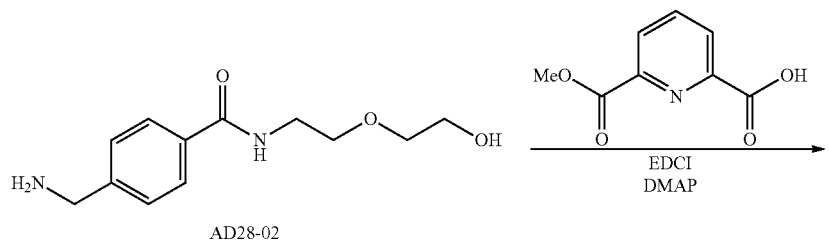

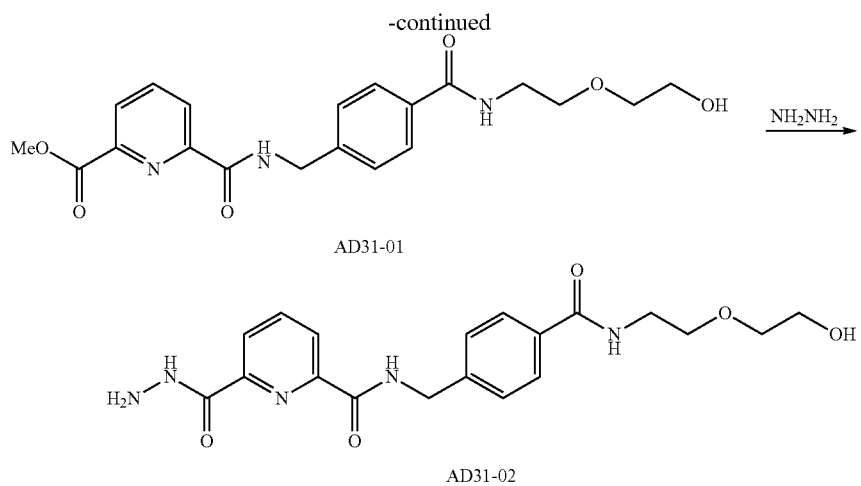

AD31-01

AD31-02

Reference Synthetic Example 18

Synthesis of AD09-05
1) Synthesis of AD09-02

4 g (16.8 mmol) of 1-(N-Boc-aminomethyl)-4-(aminomethyl)benzene in 80 mL of methylene chloride was mixed with 5.6 mL (40 mmol) of triethylamine and 1.9 mL (20 mmol) of acetic anhydride under cooling with ice and stirred at room temperature for 1 hour. The reaction solution was diluted with 100 mL of methylene chloride, washed with 100 mL of water, 100 mL of saturated aqueous sodium hydrogen carbonate and 100 mL of saturated aqueous sodium chloride, dried over anhydrous sodium sulfate and filtered. The filtrate was concentrated under reduced pressure to obtain AD09-02.

2) Synthesis of AD09-03

AD09-02 in 50 mL of 1,4-dioxane was stirred with 50 mL of 4 M hydrochloric acid/1,4-dioxane at room temperature for 2 hours. The precipitated crystals were collected by filtration, washed with 50 mL of dioxane and dried under reduced pressure to obtain 4.31 g (19.2 mmol, calculated) of AD09-03.

3) Synthesis of AD09-04

1.3 g (6.0 mmol) of AD09-03 suspended in 50 mL of methylene chloride was stirred with 50 mL of saturated aqueous sodium hydrogen carbonate and 1 g (4.9 mmol) of methyl 5-(chlorocarbonyl)thiophene-2-carboxylate (TEC) at room temperature for 2 hours. The precipitated crystals were collected by filtration, washed with 100 mL of methylene chloride and dried under reduced pressure to obtain 1.35 g (3.8 mmol, yield 63%) of AD09-04.

4) Synthesis of AD09-05

1.35 g (3.8 mmol) of AD09-04 in 26 mL of ethanol was mixed with 3.8 mL of hydrazine monohydrate and stirred at 70° C. overnight. The precipitated crystals were collected by filtration, washed with 30 mL of ethanol and dried under reduced pressure to obtain 1.21 g (3.4 mmol, yield 90%) of AD09-05.

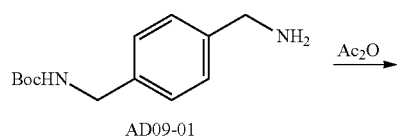

AD09-01

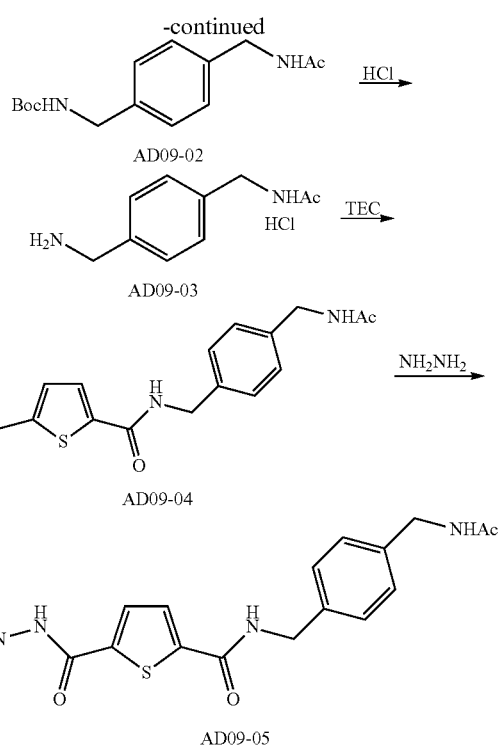

Reference Synthetic Example 19

Synthesis of AD10-02
1) Synthesis of AD10-01

3.72 g (15.6 mmol) of AD28-02 was dissolved in 100 mL of saturated aqueous sodium hydrogen carbonate and 100 mL of tetrahydrofuran (THF), mixed with 3.3 g (16 mmol) of methyl 5-(chlorocarbonyl)thiophene-2-carboxylate (TEC) and stirred for 30 minutes. 200 mL of water was added, and the precipitated crystals were collected by filtration, washed with 150 mL of water and dried under reduced pressure to obtain 4.76 g (11.7 mmol, yield 75%) of AD10-01.

2) Synthesis of AD10-02

4.76 g (11.7 mmol) of AD10-01 in 100 mL of ethanol was mixed with 11 mL of hydrazine monohydrate at room temperature and stirred at 80° C. for 15 hours. The reaction solution was allowed to cool to room temperature and concentrated under reduced pressure, and 100 mL of water was added. The precipitated crystals were collected by filtration, washed with 50 mL of water and dried under reduced pressure to obtain 4.02 g (9.9 mmol, yield 84%) of AD10-02.

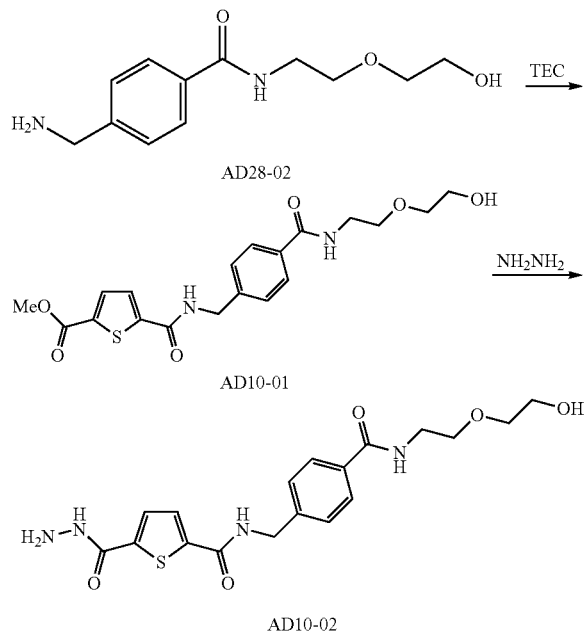

Reference Synthetic Example 20

Synthesis of AD11-07
1) Synthesis of AD11-03
4.37 g (19 mmol) of 4-bromomethylphenylacetic acid was mixed with 90 mL of 7 M ammonia/methanol and stirred at room temperature for 1 hour. The reaction solution was concentrated under reduced pressure, mixed with 60 mL of 1 mol/L sodium hydroxide and concentrated under reduced pressure. The resulting residue was dissolved in 30 mL of 1,4-dioxne and 30 mL of water, mixed with 25 mL of 1 mol/L sodium hydroxide and 4.4 mL of di-tert-butyl carbonate under cooling with ice and stirred at room temperature overnight. The reaction solution was concentrated under reduced pressure adjusted to pH 3 by gradually adding 42 mL of 10% aqueous citric acid and extracted with 200 mL of methylene chloride three times. The organic layers were combined, washed with 100 mL of saturated aqueous sodium chloride, dried over anhydrous sodium sulfate and concentrated under reduced pressure. The resulting residue was purified by silica gel chromatography (silica gel 100 g, methylene chloride: methanol=98:2) to obtain 2.42 g (9.1 mmol, yield 48%) of AD11-03.
2) Synthesis of AD11-04
1.86 g (7.0 mmol) of AD11-03 in 18 mL of methylene chloride was mixed with 1.25 g (7.7 mmol) of carbonylbisimidazole (CDI) at room temperature and stirred at the same temperature for 1 hour. The reaction solution was mixed with 3.5 mL of 28% aqueous ammonia and stirred at the same temperature overnight. The reaction solution was concentrated under reduced pressure, mixed with 30 mL of methanol and then concentrated under reduced pressure again. The resulting residue was washed by suspending in 30 mL of water and dried under reduced pressure to obtain 1.76 g (6.7 mmol, yield 95%) of AD11-04.

3) Synthesis of AD11-05
1.72 g (6.5 mmol) of AD11-04 was stirred with 60 mL of 4 M hydrochloric acid/1,4-dioxane at room temperature overnight. The reaction solution was concentrated under reduced pressure, washed by suspending in ethyl acetate-hexane and dried under reduced pressure to obtain 1.73 g of AD11-05.

4) Synthesis of AD11-06
1.32 g (6.6 mmol) of AD11-05 suspended in 30 mL of tetrahydrofuran (THF) was mixed with 120 mL of saturated aqueous sodium hydrogen carbonate and 2.02 g (9.9 mmol) of methyl 5-(chlorocarbonyl)thiophene-2-carboxylate (TEC) and stirred at room temperature overnight. The reaction solution was adjusted to pH 2 with 100 mL of 1 mol/L hydrochloric acid under cooling with ice and dried under reduced pressure. The resulting solid was subjected to short-path column chromatography (silica gel 20 g, methylene chloride:methanol=9:1) to obtain 2.37 g of crude AD11-05. The crude product was washed by suspending in 100 mL of saturated aqueous sodium hydrogen carbonate to obtain 1.64 g (4.9 mmol, yield 75%) of AD11-06.

5) Synthesis of AD11-07
1.58 g (4.75 mmol) of AD11-06 in 25 mL of ethanol was stirred with 5 mL of hydrazine monohydrate at 80° C. overnight, then with additional 5 mL of hydrazine monohydrate at the same temperature overnight and further with another 5 mL of hydrazine monohydrate at the same temperature overnight (a total of 15 mL of hydrazine monohydrate). The reaction solution was allowed to cool to room temperature, and the precipitated crystals were collected by filtration, washed with 20 mL of ethanol and dried under reduced pressure to obtain 1.47 g (4.42 mmol, yield 93%) of AD11-07.

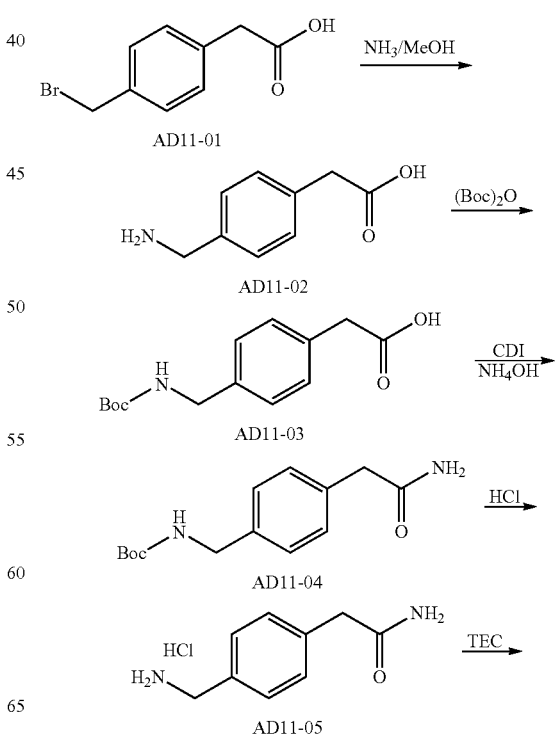

-continued

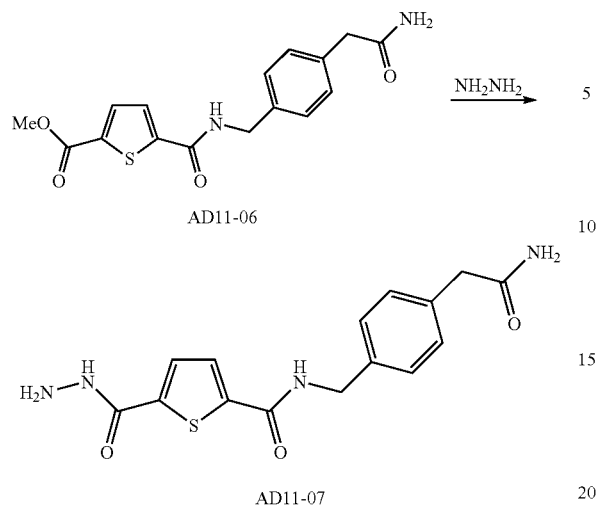

AD11-06

AD11-07

Reference Synthetic Examples 21 to 27

The following compounds (Reference Synthetic Examples 21 to 27) were synthesized in accordance with WO2004/108683 or US2006094694.

Reference Synthetic Example 21 (BC-1)

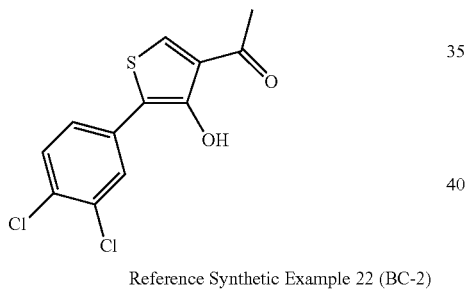

Reference Synthetic Example 22 (BC-2)

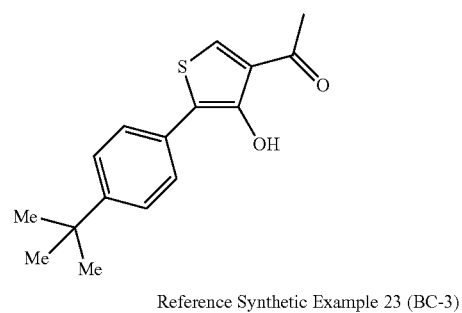

Reference Synthetic Example 23 (BC-3)

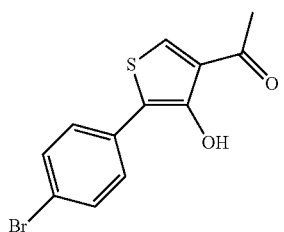

-continued

Reference Synthetic Example 24 (BC-4)

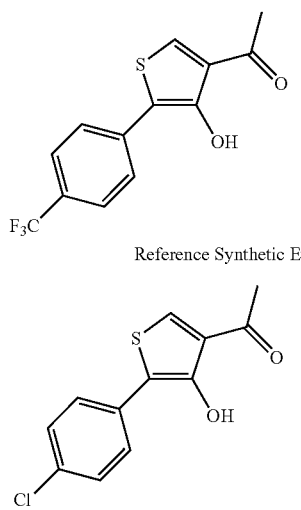

Reference Synthetic Example 25 (BC-5)

Reference Synthetic Example 26 (BC-6)

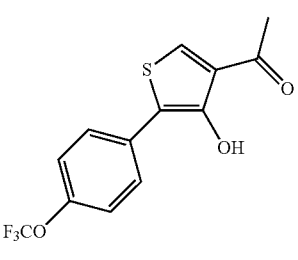

Reference Synthetic Example 27 (BC-7)

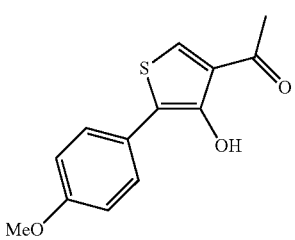

Reference Synthetic Example 28

Synthesis of methyl 5-(chlorocarbonyl)thiophene-2-carboxylate (TEC)

150 g (749 mmol) of dimethyl thiophene-2,5-dicarboxylate in 1350 mL of toluene was azeotropically distilled at 130° C. to evaporate 150 mL of it. The reaction solution was cooled to an inner temperature of 70° C., then stirred with 300 mL of 2.5 M potassium hydroxide/methanol for 40 minutes and cooled to room temperature, and the precipitated solid was washed with ethyl acetate by filtration and dried under reduced pressure to obtain 160 g of potassium 5-(methoxycarbonyl)-thiophene-2-carboxylate. 100 g (446 mmol) of potassium 5-(methoxycarbonyl)-thiophene-2-carboxylate in 700 mL of 1,2-dichloroethane was mixed with 1.73 mL of N,N-dimethylformamide and heated to 90° C., and 68.9 g (119 mmol) of thionyl chloride was added dropwise. The reaction solution was refluxed for 1 hour and then cooled to room temperature, and the resulting crystals were filtered off with 300 mL of 1,2-dichloroethane. The filtrate was concentrated to dryness to obtain 90.4 g (yield 99%) of methyl 5-(chlorocarbonyl)thiophene-2-carboxylate (TEC).
Morphology: pale purple solid Reference Synthetic Example 29

Synthesis of AD18-03
5 g (38 mmol) of tert-butyl carbazate in 100 mL of methylene chloride was mixed with 7 mL (50 mmol) of triethylamine. The reaction solution was mixed with 5 g (24.5 mmol) of methyl 5-(chlorocarbonyl)thiophene-2-carboxylate (TEC) under cooling with ice, stirred at room temperature for 1 hour, diluted with 250 mL of methylene chloride, washed with 100 mL of 2 mol/L hydrochloric acid, 100 mL of saturated aqueous sodium hydrogen carbonate and 100 mL of saturated aqueous sodium chloride, dried over anhydrous sodium sulfate and filtered. The filtrate was concentrated under reduced pressure to obtain AD18-02. AD18-02 was dissolved in 100 mL of methanol and stirred with 100 mL of 2 mol/L aqueous sodium hydroxide at 50° C. for 4 hours. The reaction solution was concentrated under reduced pressure, and 20 g of citric acid was added under cooling with ice. The precipitated crystals were collected by filtration, washed with 50 mL of water and dried under reduced pressure to obtain 5.96 g (21 mmol, overall yield over two steps 55%) of AD18-03.

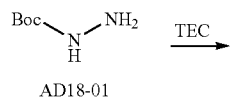

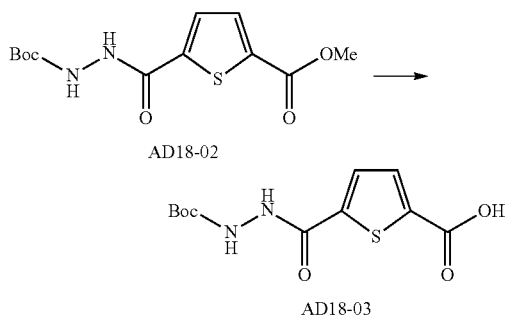

Reference Synthetic Example 30

Synthesis of AD18-04
To 17.23 g (114 mmol) of 4-aminomethylbenzoic acid suspended in 175 mL of water, 13.7 g (342 mmol) of sodium hydroxide was gradually added at room temperature, and then 17.7 mL (125 mmol) of benzyl chloroformate was added dropwise over 20 minutes. The reaction solution was stirred for 1 day and adjusted to pH 1 by adding 175 mL of 2 mol/L hydrochloric acid. The precipitated crystals were collected by filtration, washed with 150 mL of water and dried under reduced pressure to obtain 38.8 g (calculated) of AD18-04.

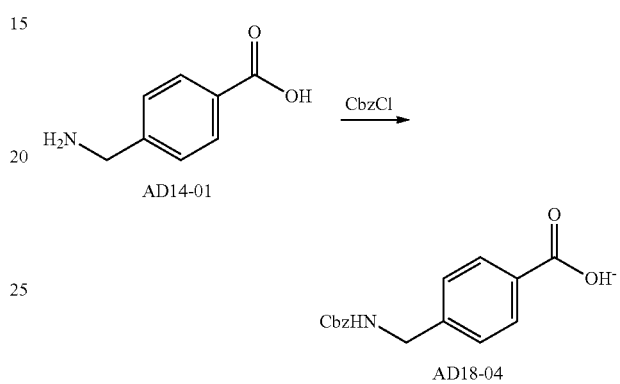

Synthetic Example 1

Synthesis of TCA1-13
66 mg (0.15 mmol) of AD13-06 synthesized in Reference Synthetic Example 1, 43 mg (15 mmol) of BC-1 synthesized in Reference Synthetic Example 21 and 0.5 mL of DMSO were heated in a reaction vessel at an outer temperature of 100° C. for 19 hours with stirring. The reaction solution was cooled to room temperature and mixed with 5 mL of water. The precipitated solid was collected by filtration, rinsed with 20 mL of water and dried under reduced pressure to obtain 94 mg (0.132 mmol, yield 88%) of TCA1-13.
Morphology: pale yellow solid
LC/MS (ESI$^+$) m/z; 711, 713 [M+1]
LC/MS (ESI$^-$) m/z; 709, 711 [M−1]
Retention time 3.47 (min)
In Synthetic Examples 2 to 72, synthesis was carried out in the same manner as in Synthetic Example 1. The morphology of the resulting compounds and the observed peaks and retention times in LC/MS are shown in Tables 2-1 to 2-6.

TABLE 2-1

| Synthetic Example | Morphology | Observed peak (ESI$^+$) | Observed peak (ESI$^-$) | Retention time (min) |
|---|---|---|---|---|
| 2 | Yellow solid | 699 | 697 | 3.58 |
| 3 | Yellow solid | 721, 723 | 719, 721 | 3.33 |
| 4 | Pale yellow solid | 678, 680 | 676, 678 | 3.28 |
| 5 | Yellow solid | 666 | 664 | 3.42 |
| 6 | Pale yellow solid | 688, 690 | 686, 688 | 3.15 |
| 7 | Pale yellow solid | 667, 669 | 665, 667 | 3.67 |
| 8 | Yellow solid | 655 | 653 | 3.77 |
| 9 | Yellow solid | 677, 679 | 675, 677 | 3.54 |
| 10 | Pale yellow solid | 671, 673 | 669, 671 | 3.58 |
| 11 | Yellow solid | 659 | 657 | 3.68 |
| 12 | Yellow solid | 681, 683 | 679, 681 | 3.43 |

TABLE 2-2

| Synthetic Example | Morphology | Observed peak (ESI+) | Observed peak (ESI−) | Retention time (min) |
|---|---|---|---|---|
| 13 | Pale yellow solid | 631, 633 | 629, 631 | 3.36 |
| 14 | Yellow solid | 619 | 617 | 3.48 |
| 15 | Yellow solid | 641, 643 | 639, 641 | 3.22 |
| 16 | Yellowish brown solid | 744, 746 | 742, 744 | 3.00 |
| 17 | Yellowish brown solid | 732 | 730 | 3.11 |
| 18 | Yellowish brown solid | 754, 756 | 752, 754 | 2.88 |
| 19 | Pale yellow solid | 700, 702 | 698, 700 | 3.05 |
| 20 | Yellowish brown solid | 688 | 686 | 3.15 |
| 21 | Yellowish brown solid | 710, 712 | 708, 710 | 2.95 |
| 22 | Brown solid | 718, 720 | 716, 718 | 3.00 |
| 23 | Brown solid | 706 | 704 | 3.11 |
| 24 | Brown solid | 728, 730 | 726, 728 | 2.91 |

TABLE 2-3

| Synthetic Example | Morphology | Observed peak (ESI+) | Observed peak (ESI−) | Retention time (min) |
|---|---|---|---|---|
| 25 | Brown solid | 799, 801 | 797, 799 | 3.25 |
| 26 | Yellow solid | 787 | 785 | 3.33 |
| 27 | Brown solid | 809, 811 | 807, 809 | 3.16 |
| 28 | Brown solid | 699, 701 | 697, 699 | 2.94 |
| 29 | Pale yellow solid | 687 | 685 | 3.04 |
| 30 | Brown solid | 709, 711 | 707, 709 | 2.76 |
| 31 | Pale yellow solid | 689, 691 | 687, 689 | 3.54 |
| 32 | Yellow solid | 677 | 675 | 3.63 |
| 33 | Yellow solid | 699, 701 | 697, 699 | 3.41 |
| 34 | Yellowish brown solid | 731, 733 | 729, 731 | 3.85 |
| 35 | Yellow solid | 719 | 717 | 3.91 |
| 36 | Yellow solid | 741, 743 | 739, 741 | 3.71 |
| 37 | Yellowish brown solid | 759, 761 | 757, 759 | 4.09 |
| 38 | Yellow solid | 747 | 745 | 4.13 |
| 39 | Yellow solid | 769, 771 | 767, 769 | 3.96 |

TABLE 2-4

| Synthetic Example | Morphology | Observed peak (ESI+) | Observed peak (ESI−) | Retention time (min) |
|---|---|---|---|---|
| 40 | Pale yellow solid | 669, 671 | 667, 669 | 3.34 |
| 41 | Yellow solid | 657 | 655 | 3.45 |
| 42 | Yellow solid | 679, 681 | 677, 679 | 3.21 |
| 43 | Pale yellow solid | 669, 671 | 667, 669 | 3.35 |
| 44 | Pale yellow solid | 657 | 655 | 3.46 |
| 45 | Yellowish brown solid | 679, 681 | 677, 679 | 3.21 |
| 46 | Pale yellow solid | 670, 672 | 668, 670 | 3.37 |
| 47 | Pale yellow solid | 658 | 656 | 3.47 |
| 48 | Yellow solid | 680, 682 | 678, 680 | 3.23 |
| 49 | Colorless solid | 670, 672 | 668, 670 | 3.42 |
| 50 | Colorless solid | 658 | 656 | 3.51 |
| 51 | Pale yellow solid | 680, 682 | 678, 680 | 3.27 |

TABLE 2-5

| Synthetic Example | Morphology | Observed peak (ESI+) | Observed peak (ESI−) | Retention time (min) |
|---|---|---|---|---|
| 52 | Pale yellow solid | 615, 617 | 613, 615 | 3.36 |
| 53 | Pale yellow solid | 603 | 601 | 3.56 |
| 54 | Pale yellow solid | 625, 627 | 623, 625 | 3.33 |
| 55 | Pale yellow solid | 615 | 613 | 3.31 |
| 56 | Pale yellow solid | 581, 583 | 579, 581 | 3.26 |
| 57 | Pale yellow solid | 631 | 629 | 3.35 |
| 58 | Pale yellow solid | 577 | 575 | 2.96 |

TABLE 2-5-continued

| Synthetic Example | Morphology | Observed peak (ESI+) | Observed peak (ESI−) | Retention time (min) |
|---|---|---|---|---|
| 59 | Pale yellow solid | 675, 677 | 673, 675 | 3.23 |
| 60 | Yellow solid | 633 | 661 | 3.44 |
| 61 | Yellowish brown solid | 685, 687 | 683, 685 | 3.19 |
| 62 | Yellowish brown solid | 675 | 673 | 3.19 |
| 63 | Yellowish brown solid | 641, 643 | 639, 641 | 3.13 |
| 64 | Yellowish brown solid | 691 | 689 | 3.23 |
| 65 | Yellowish brown solid | 637 | 635 | 2.85 |

TABLE 2-6

| Synthetic Example | Morphology | Observed peak (ESI+) | Observed peak (ESI−) | Retention time (min) |
|---|---|---|---|---|
| 66 | Pale yellow solid | 601 | 599 | 3.33 |
| 67 | Pale yellow solid | 589 | 587 | 3.42 |
| 68 | Yellow solid | 611, 613 | 69, 611 | 3.19 |
| 69 | Pale yellow solid | 601 | 599 | 3.18 |
| 70 | Pale yellow solid | 567, 569 | 565, 567 | 3.13 |
| 71 | Pale yellow solid | 617 | 615 | 3.22 |
| 72 | Yellowish brown solid | 563 | 561 | 2.84 |

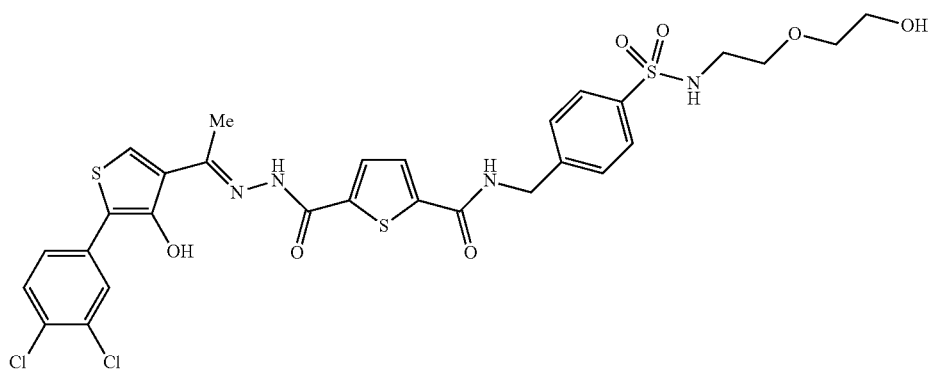

(TCA1-13)

No. 1

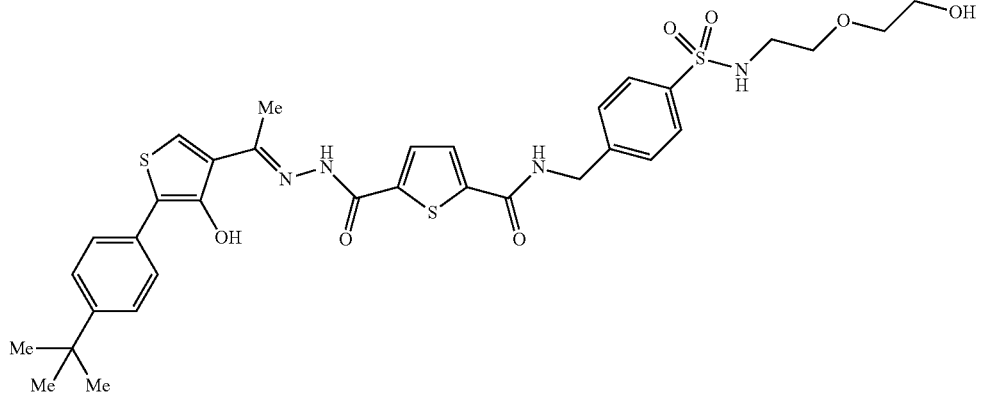

(TCA2-13)

No. 2

-continued
No. 3
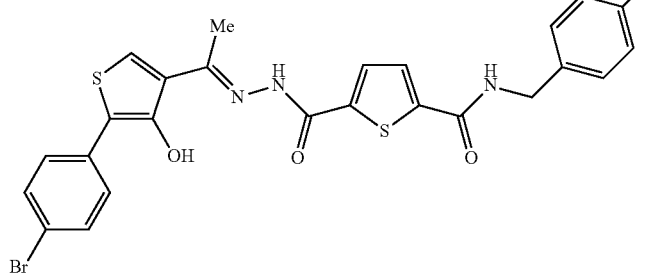
(TCA3-13)
No. 4
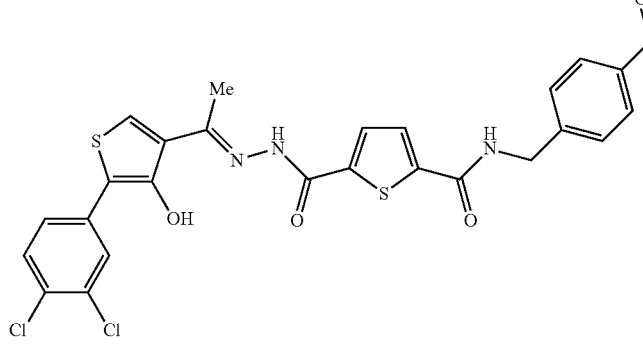
(TCA1-14)
No. 5
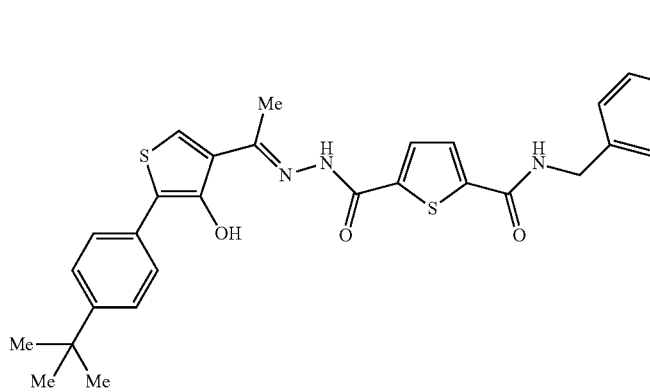
(TCA2-14)
No. 6
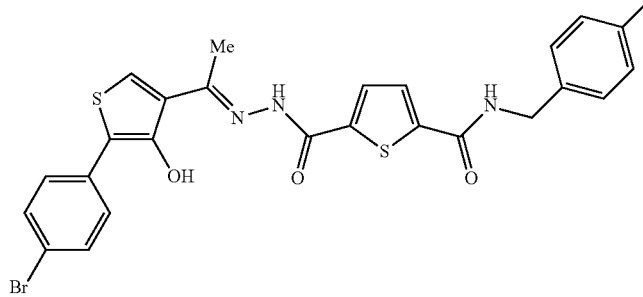
(TCA3-14)

No. 7
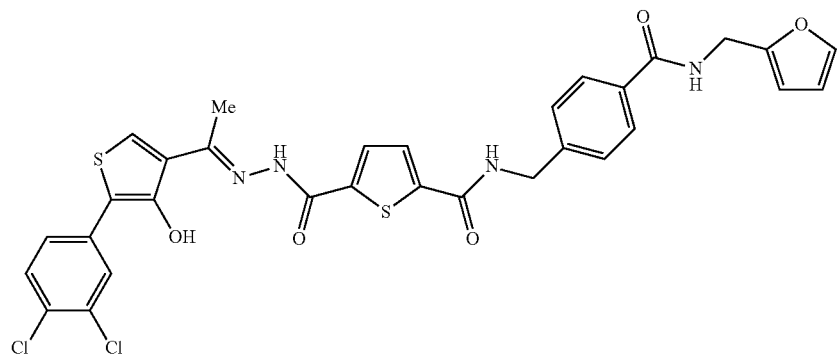
(TCA1-15)
No. 8
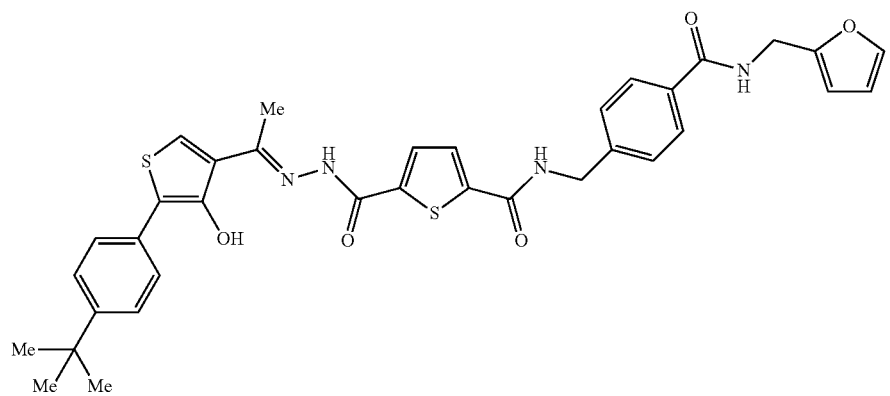
(TCA2-15)
No. 9
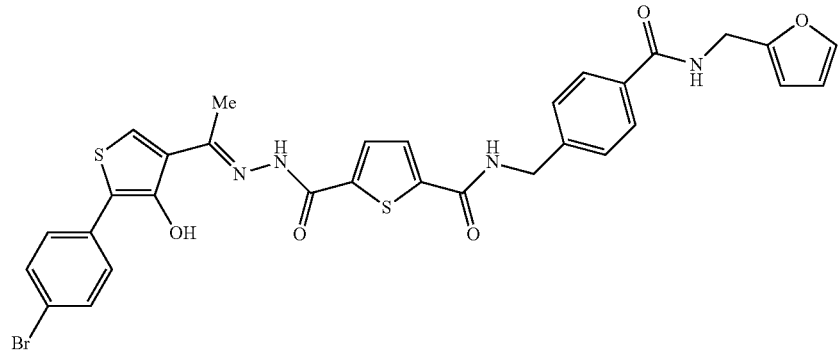
(TCA3-15)
No. 10
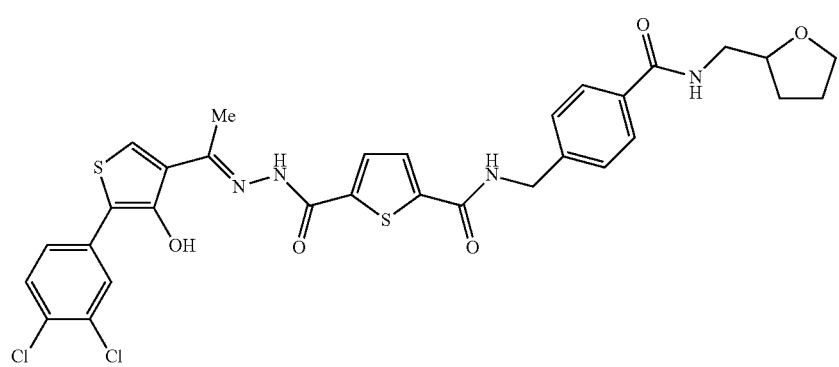
(TCA1-16)

No. 11
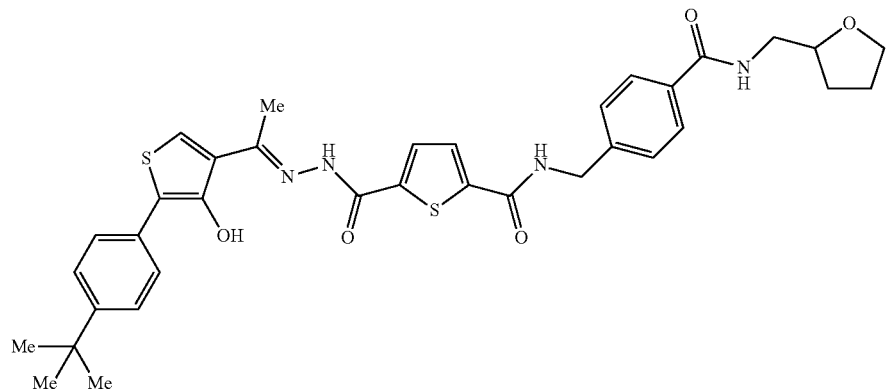
(TCA2-16)
No. 12
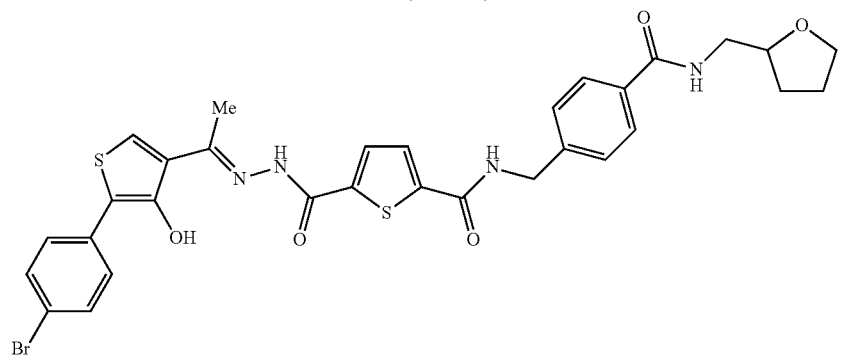
(TCA3-16)
No. 13
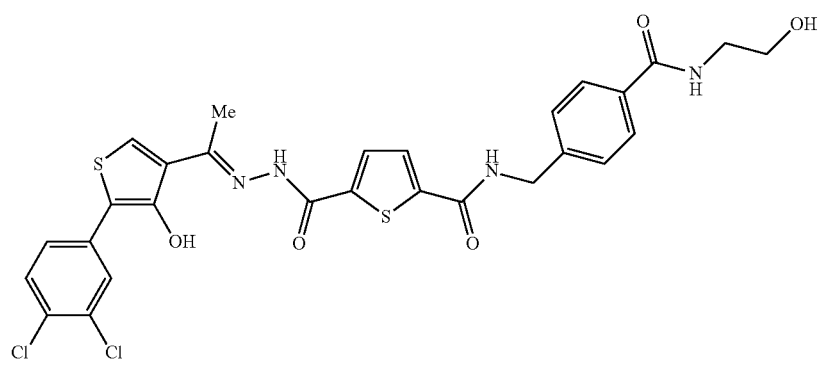
(TCA1-17)
No. 14
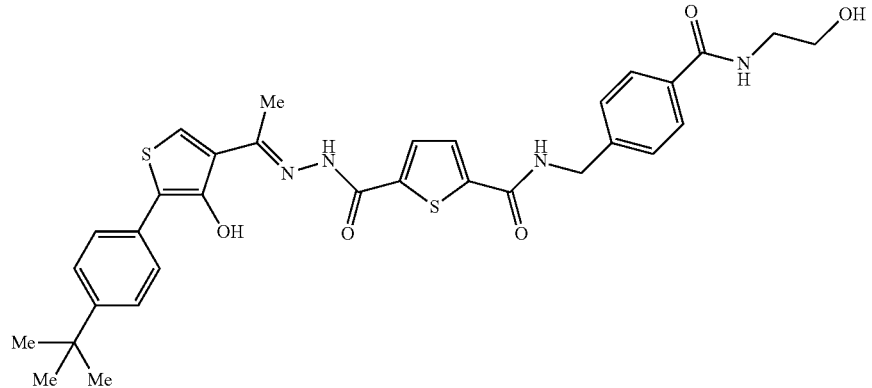
(TCA2-17)

-continued
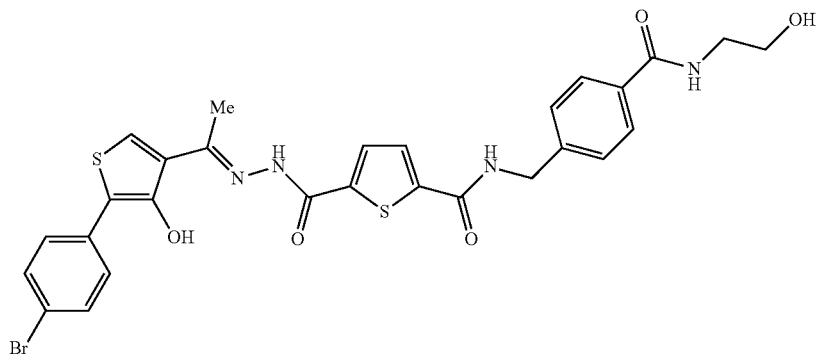
(TCA3-17) No. 15
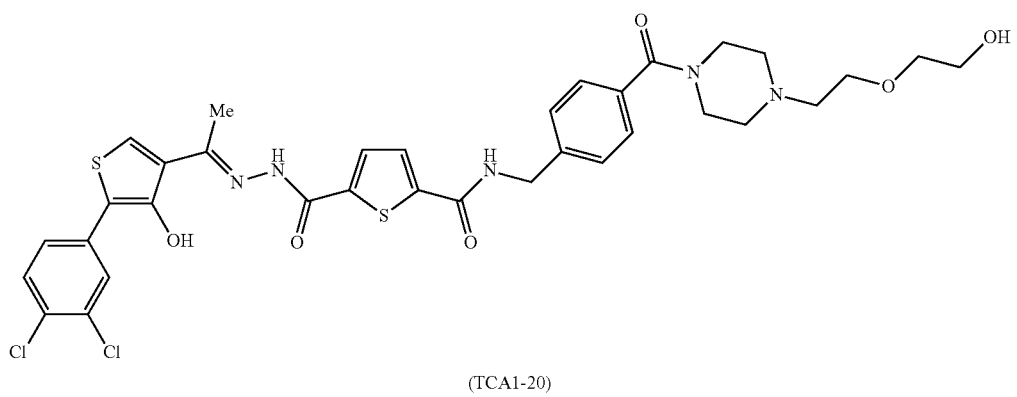
(TCA1-20) No. 16
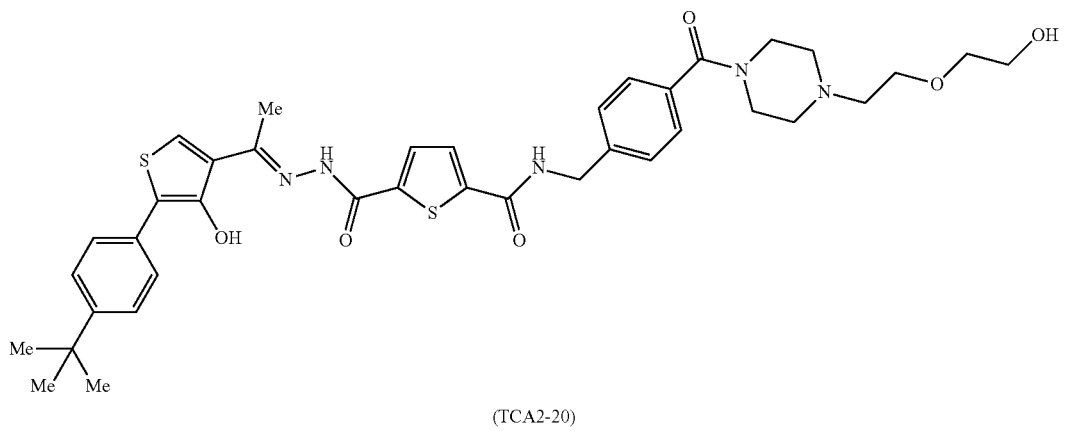
(TCA2-20) No. 17
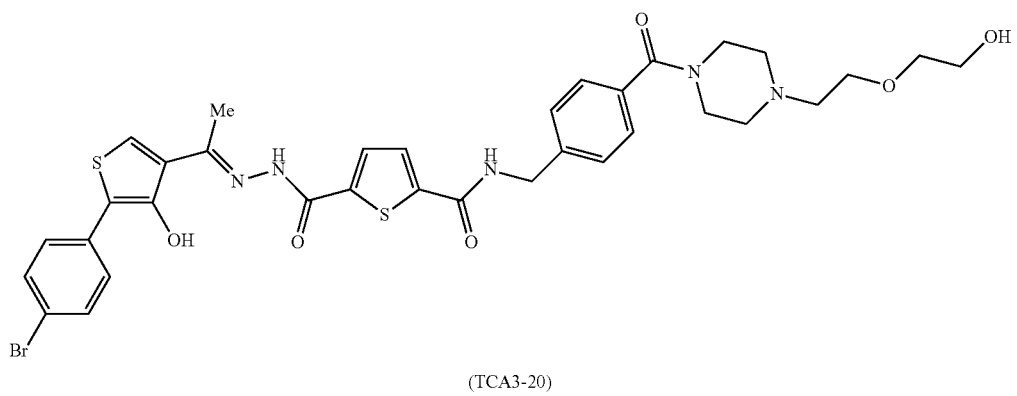
(TCA3-20) No. 18

-continued
No. 19
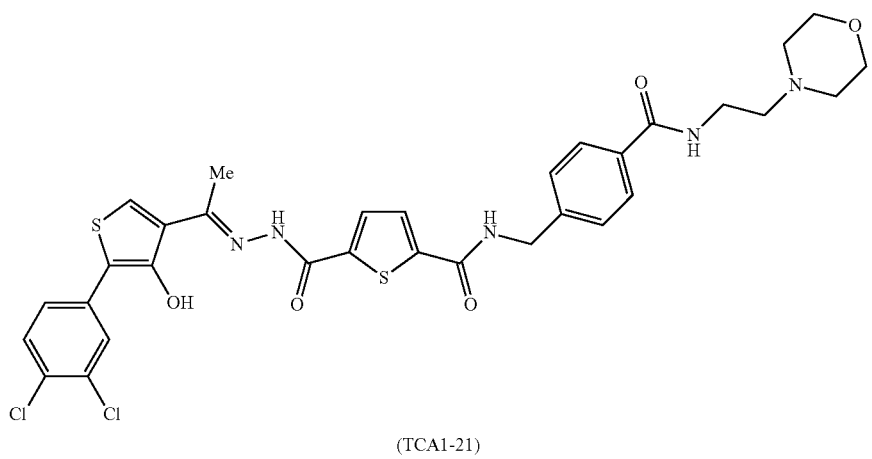
(TCA1-21)
No. 20
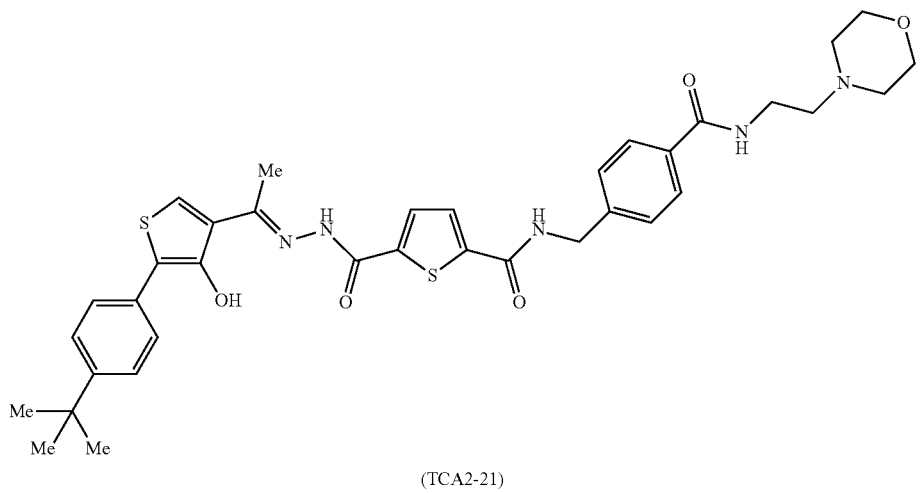
(TCA2-21)
No. 21
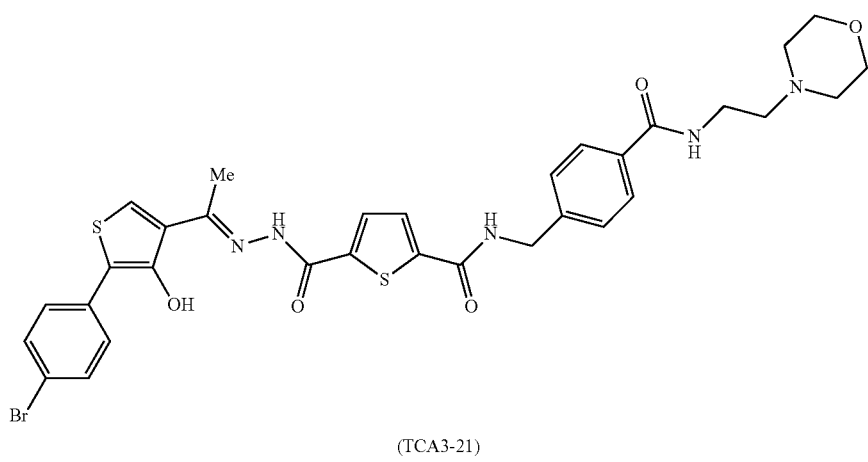
(TCA3-21)

-continued
No. 22
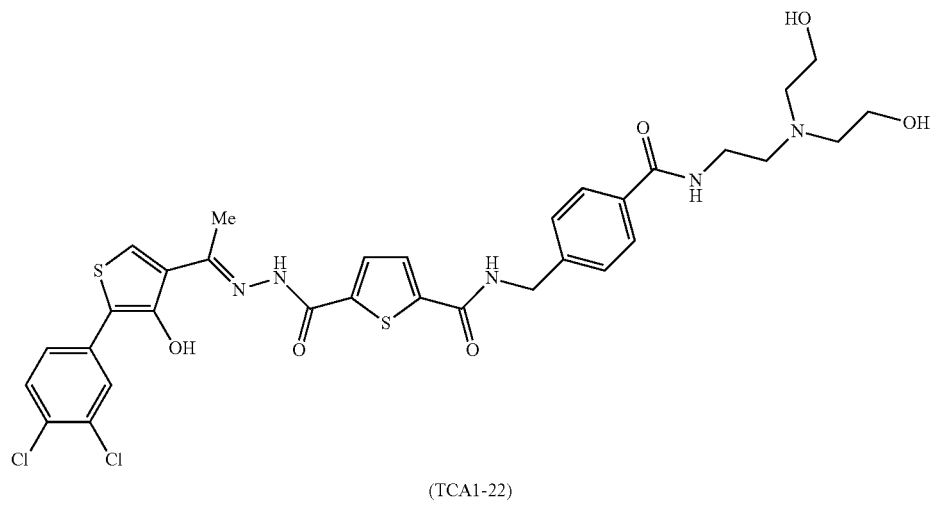
(TCA1-22)
No. 23
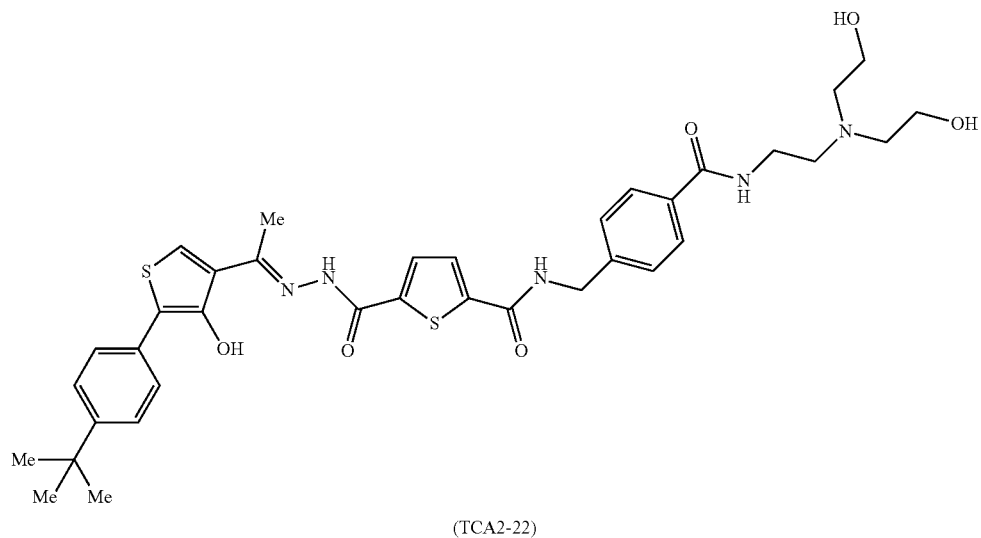
(TCA2-22)
No. 24
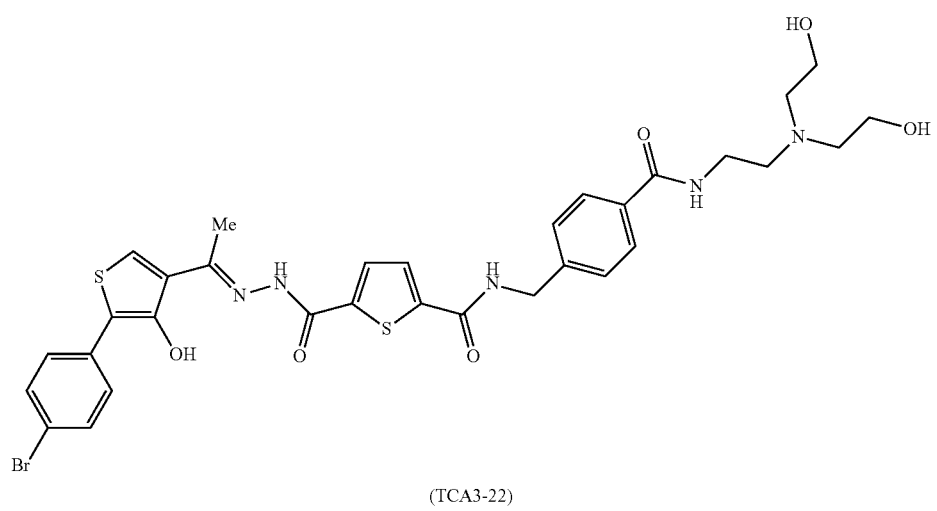
(TCA3-22)

-continued
No. 25
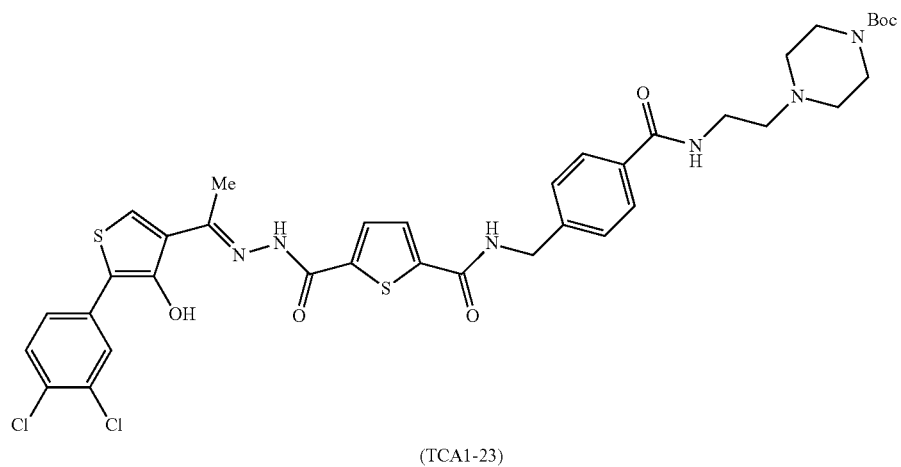
(TCA1-23)
No. 26
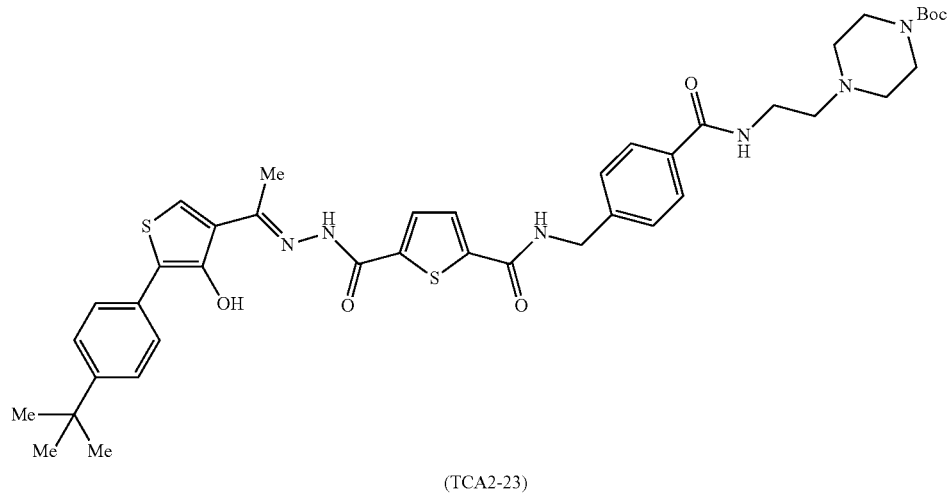
(TCA2-23)
No. 27
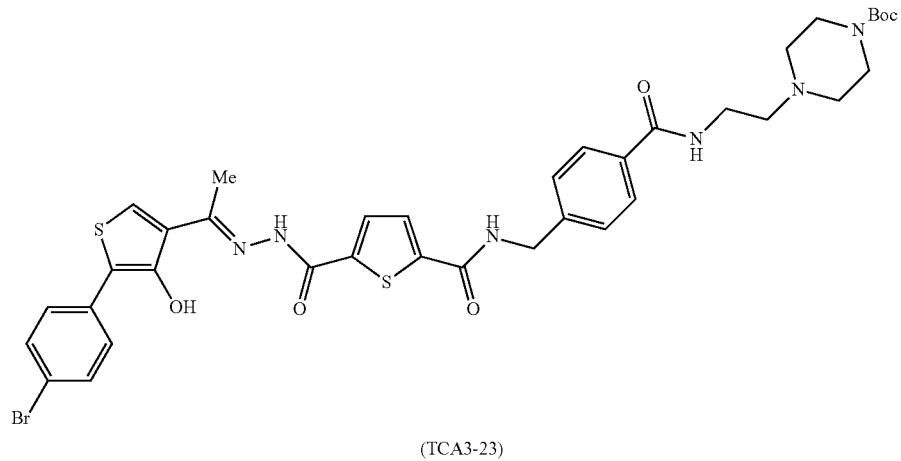
(TCA3-23)

No. 28
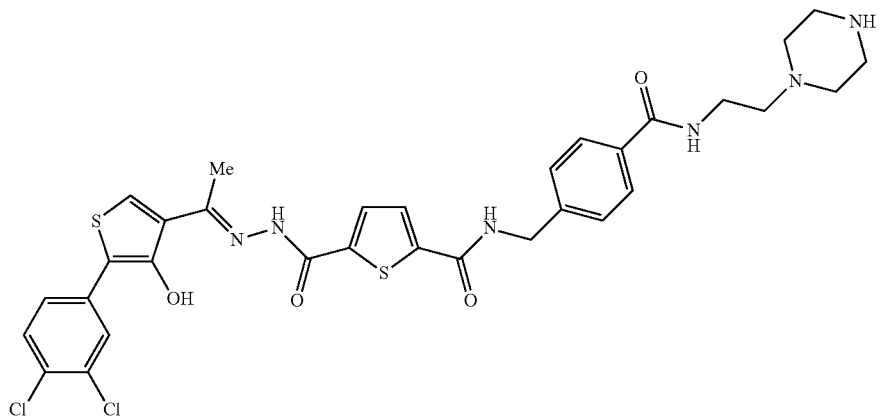
(TCA1-24)
No. 29
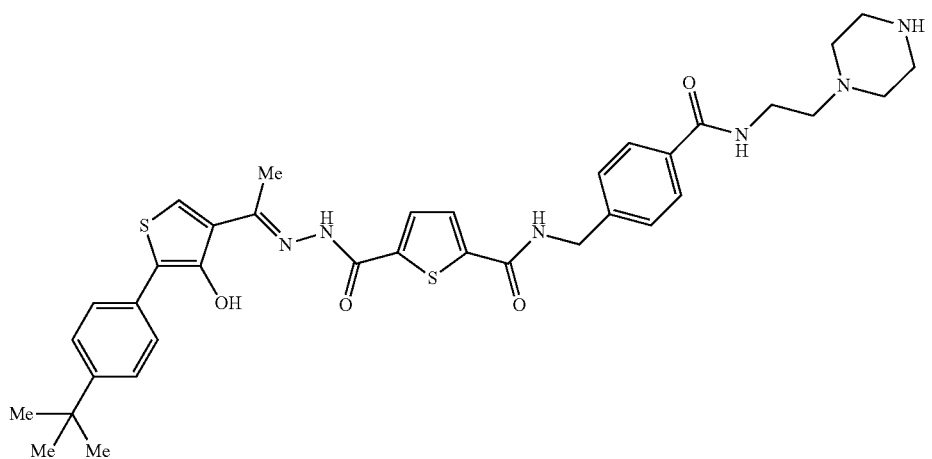
(TCA2-24)
No. 30
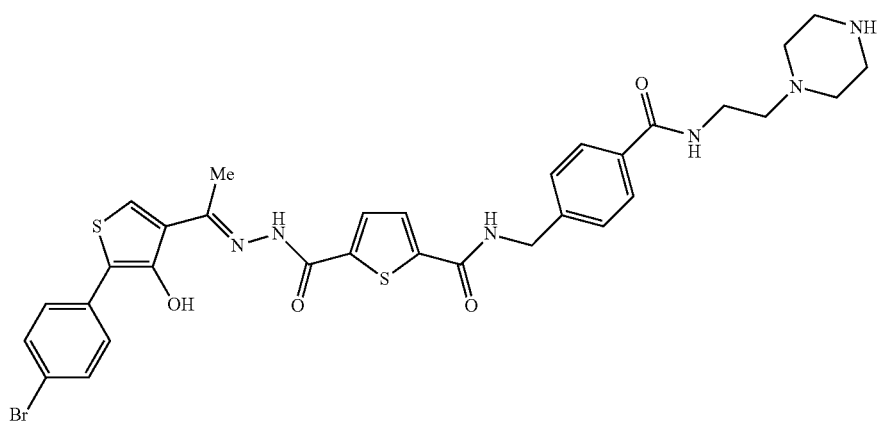
(TCA3-24)

-continued
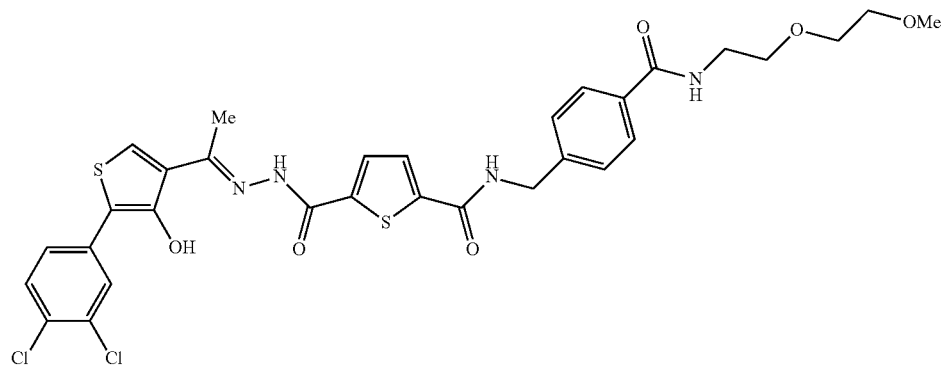
(TCA1-25) No. 31
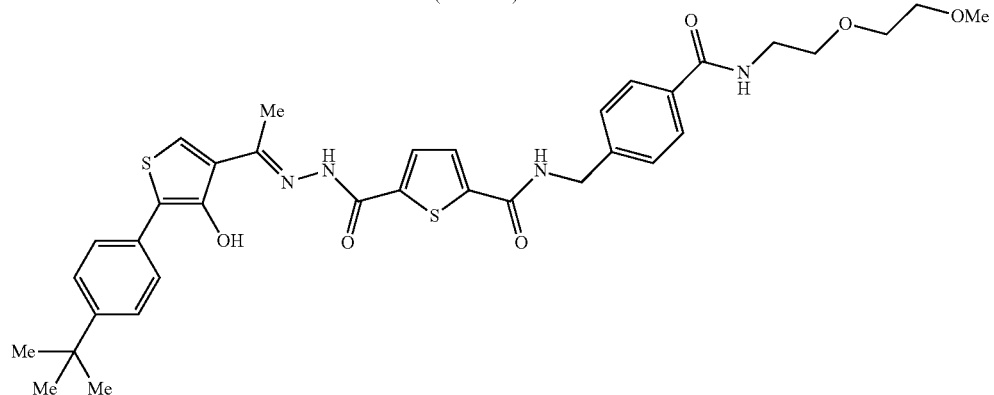
(TCA2-25) No. 32
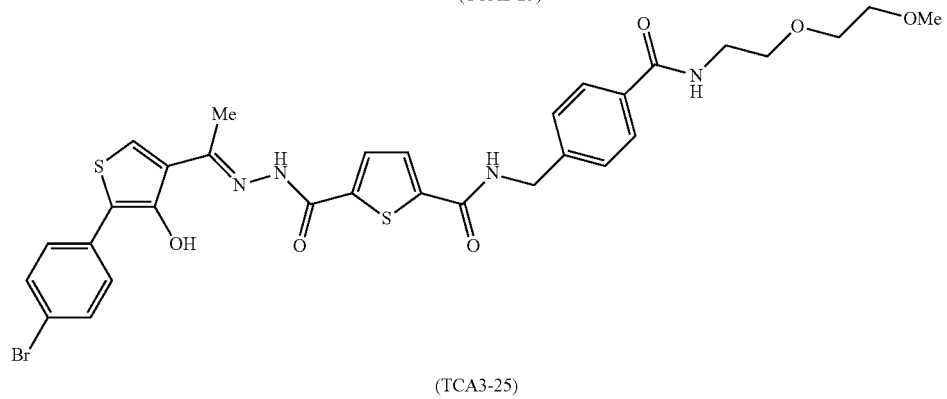
(TCA3-25) No. 33
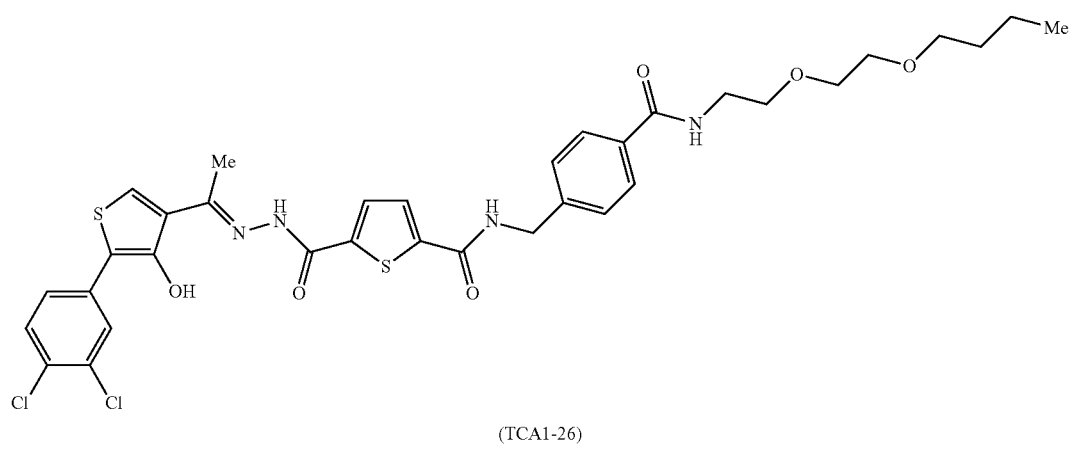
(TCA1-26) No. 34

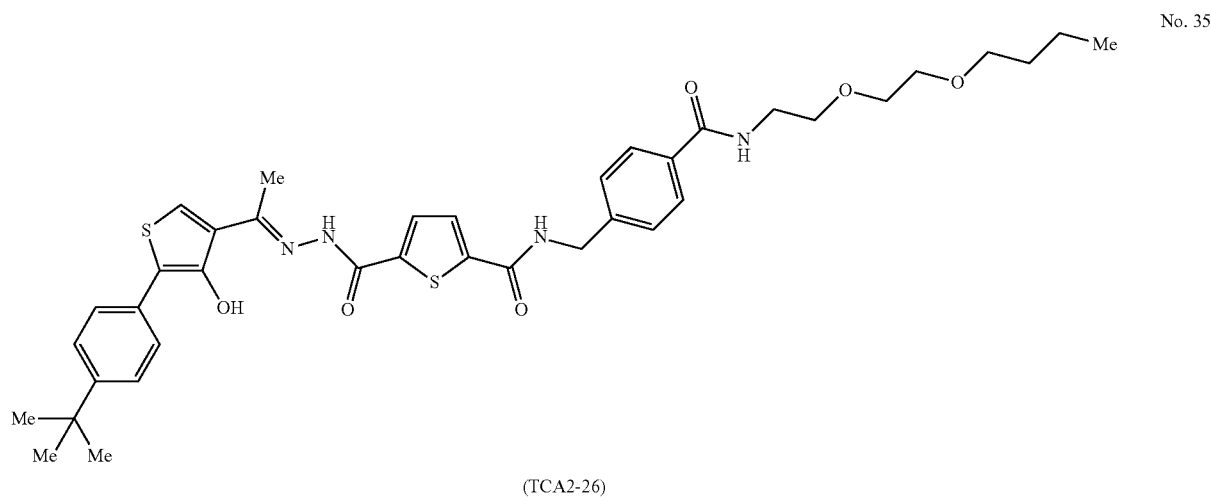
(TCA2-26) No. 35
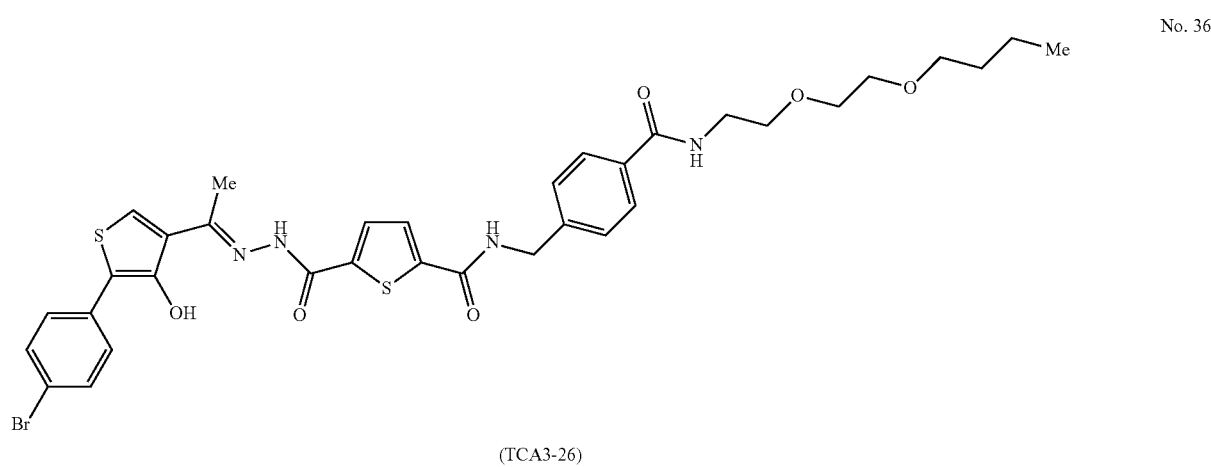
(TCA3-26) No. 36
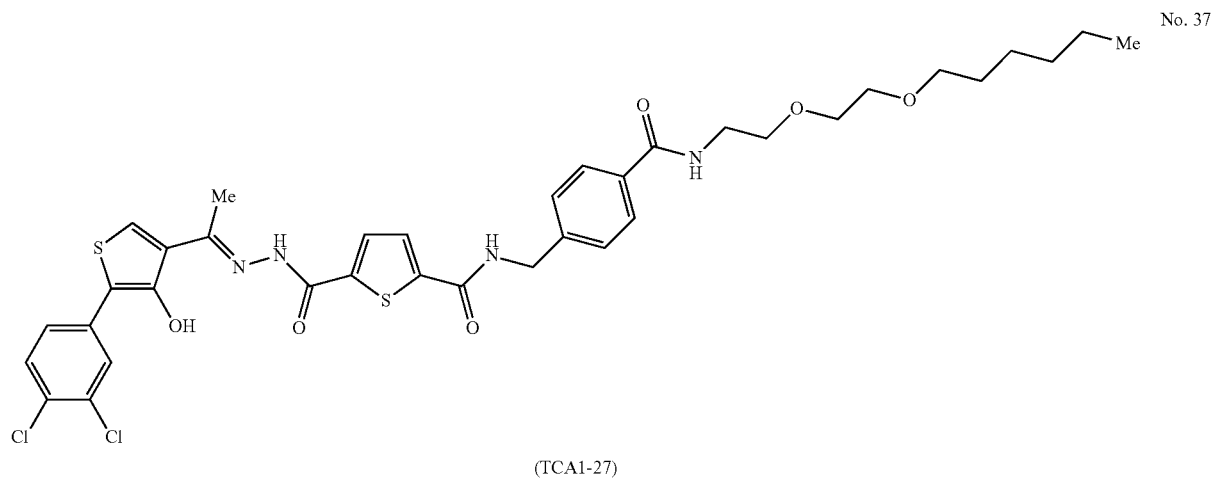
(TCA1-27) No. 37

No. 38
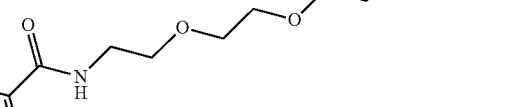
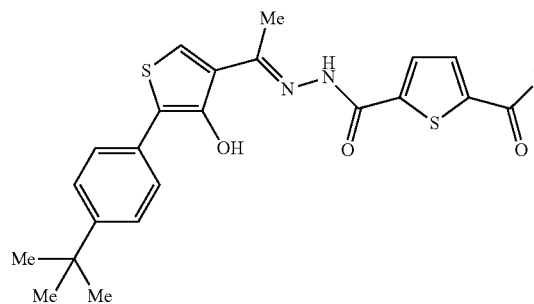
(TCA2-27)
No. 39
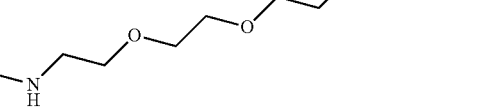
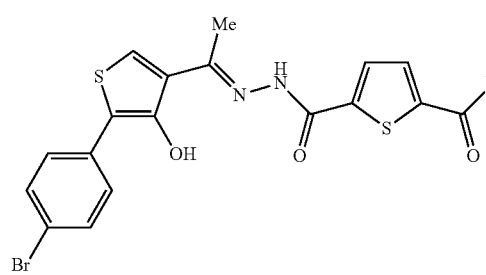
(TCA3-27)
No. 40
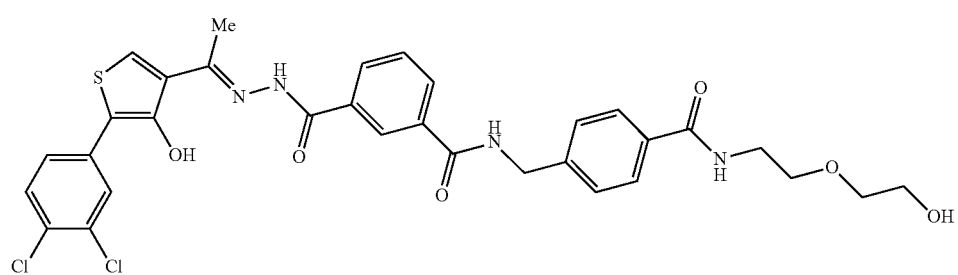
(TCA1-28)
No. 41
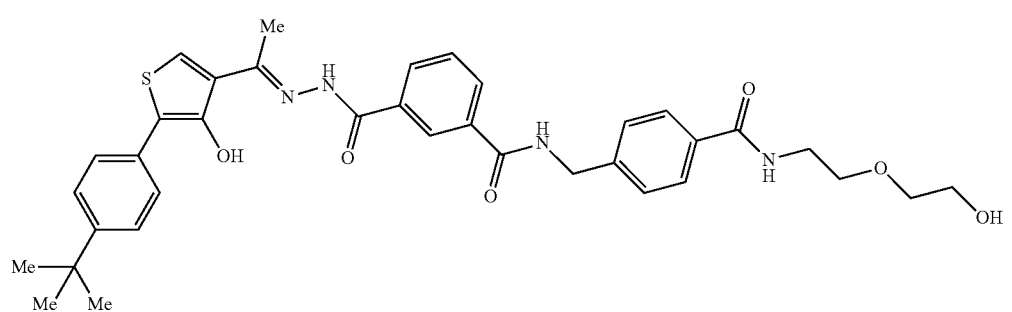
(TCA2-28)

-continued
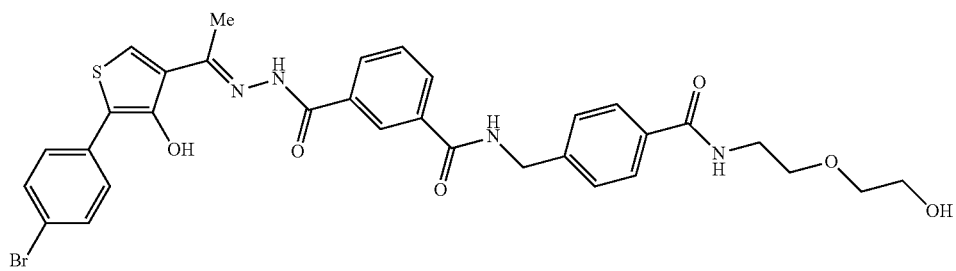
(TCA3-28)
No. 42
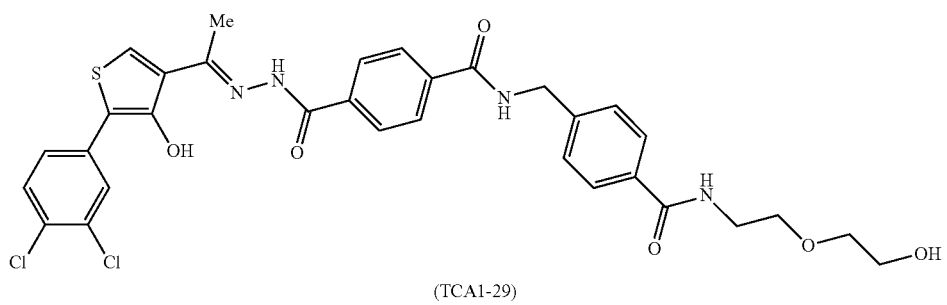
(TCA1-29)
No. 43
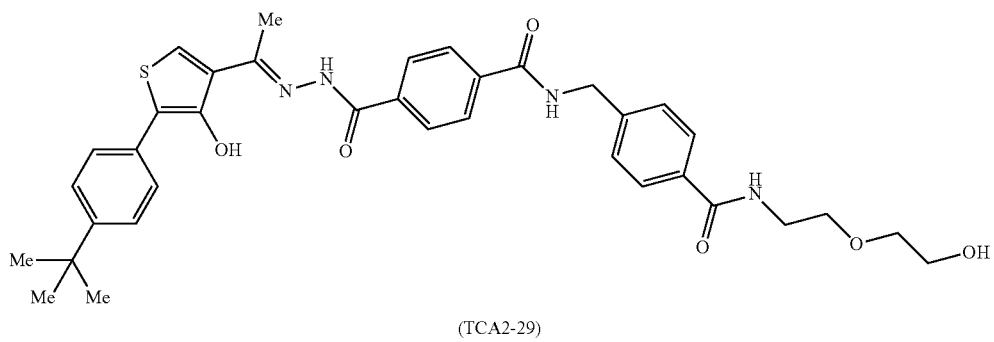
(TCA2-29)
No. 44
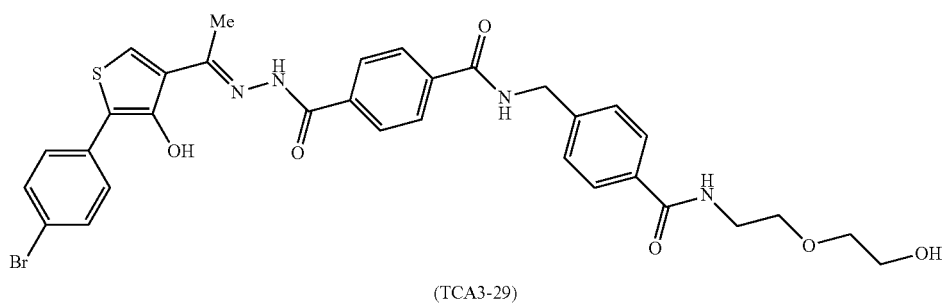
(TCA3-29)
No. 45
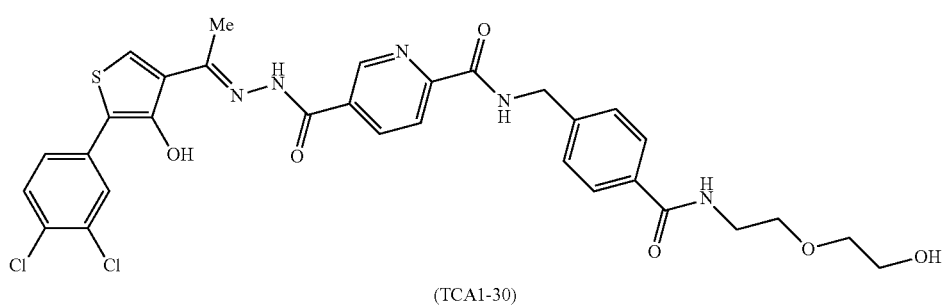
(TCA1-30)
No. 46

-continued
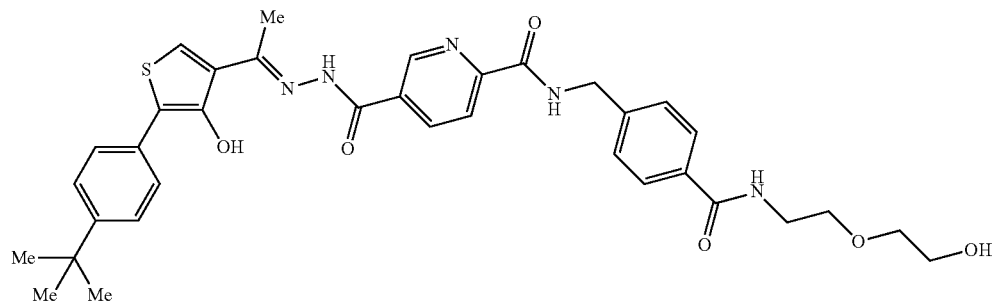
(TCA2-30)
No. 47
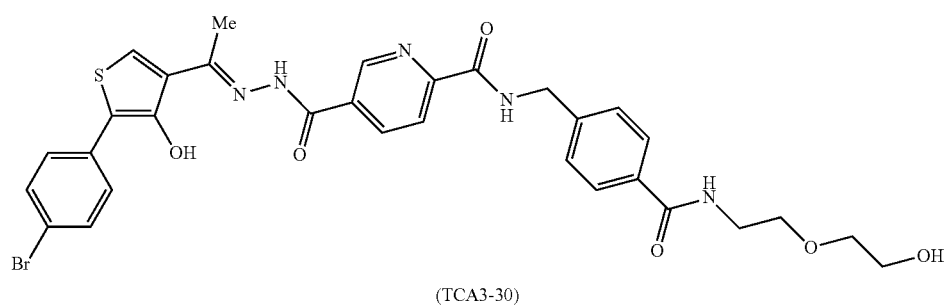
(TCA3-30)
No. 48
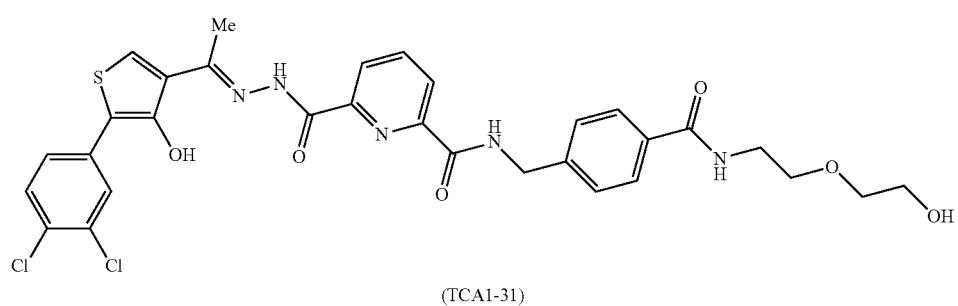
(TCA1-31)
No. 49
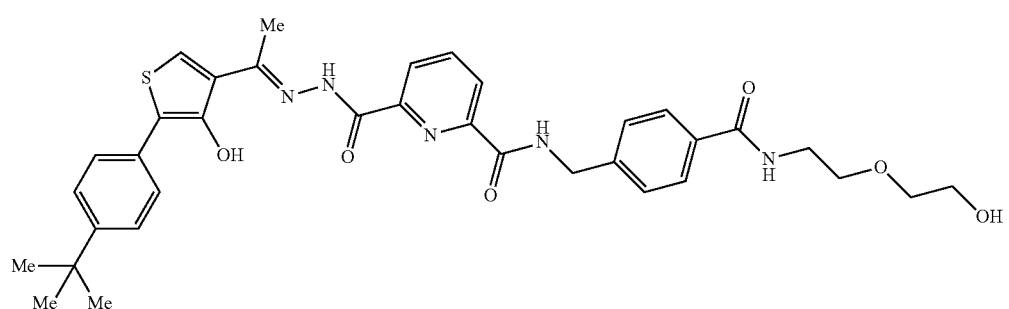
(TCA2-31)
No. 50
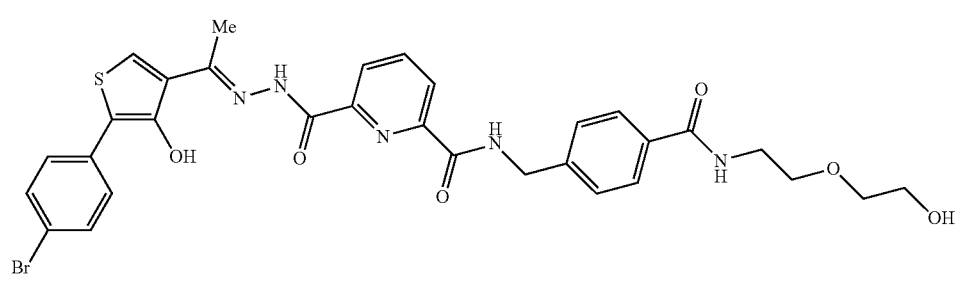
(TCA3-31)
No. 51

-continued
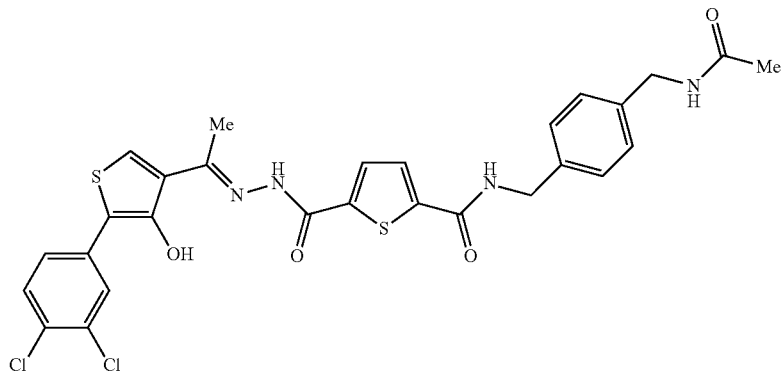
(TCA1-09)
No. 52
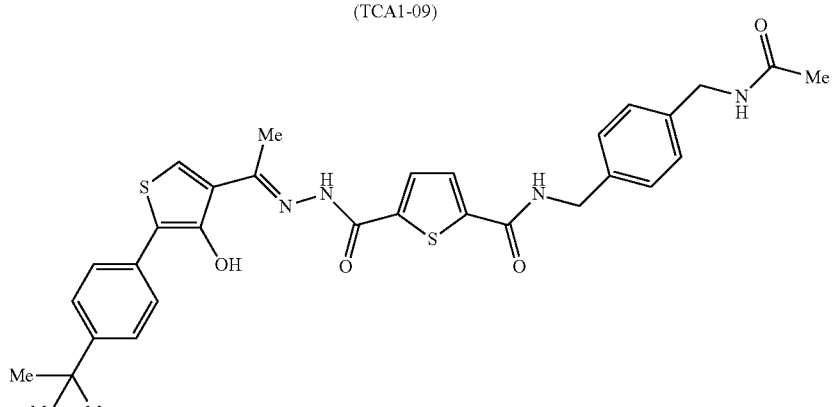
(TCA2-09)
No. 53
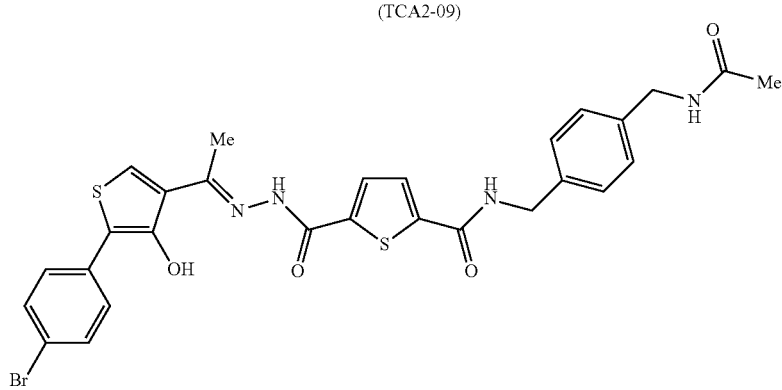
(TCA3-09)
No. 54
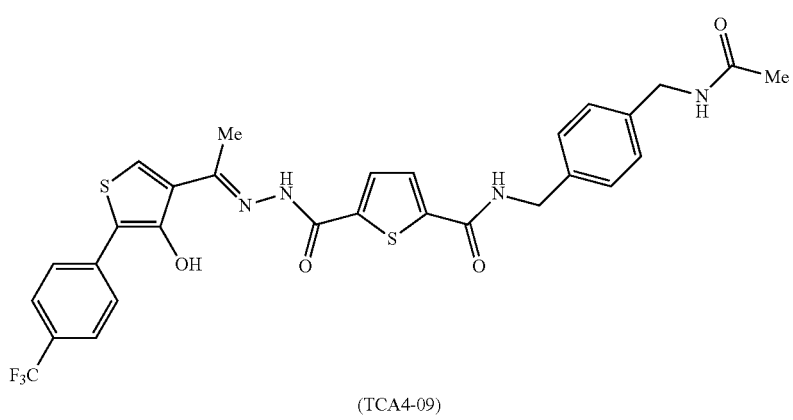
(TCA4-09)
No. 55

-continued
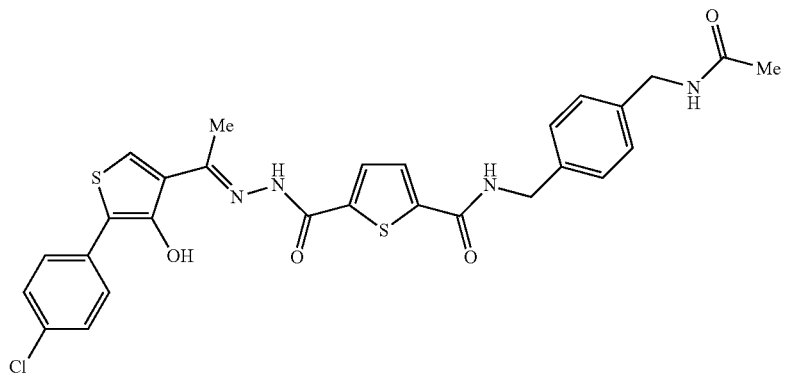
(TCA5-09)
No. 56
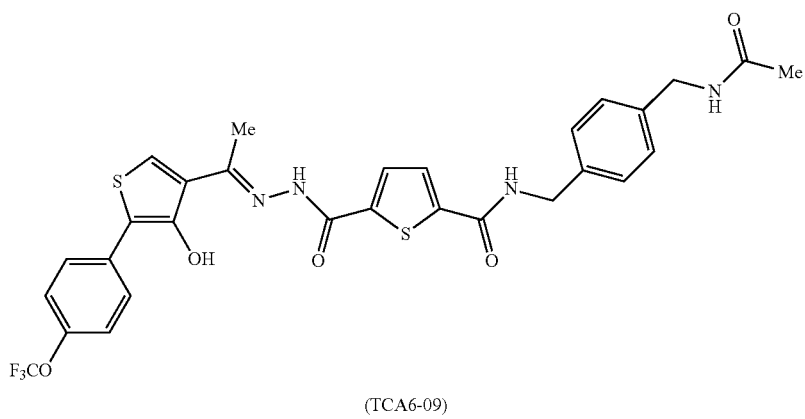
(TCA6-09)
No. 57
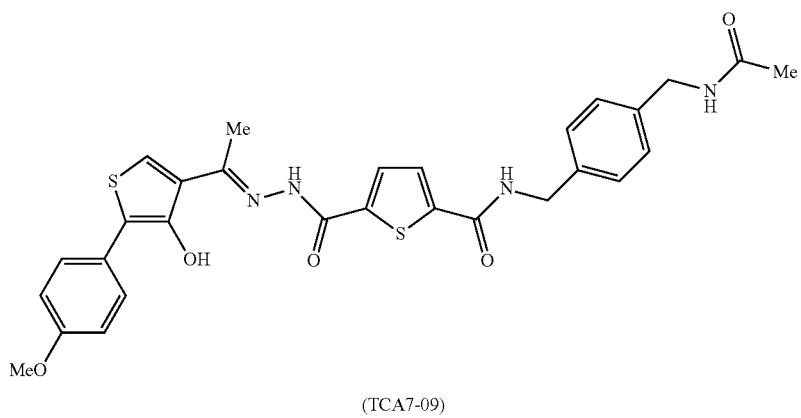
(TCA7-09)
No. 58
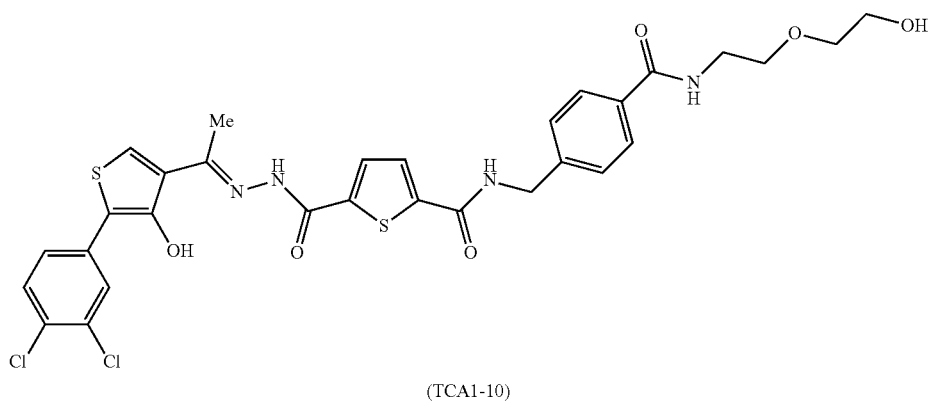
(TCA1-10)
No. 59

-continued
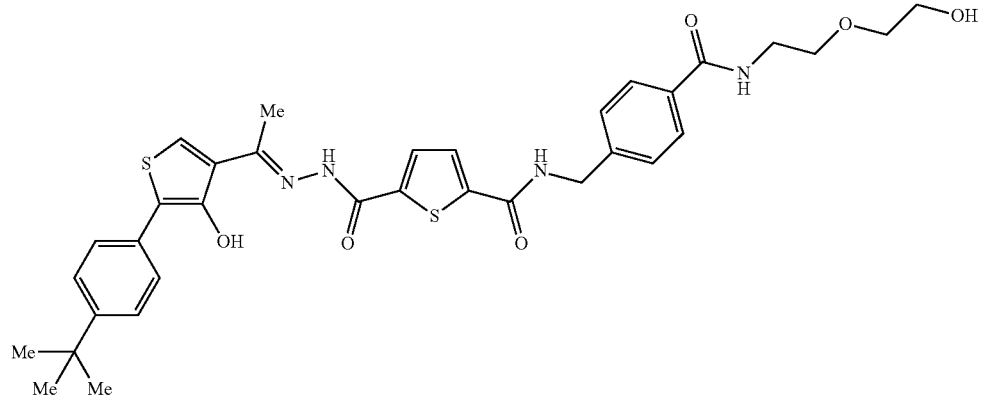
(TCA2-10)  No. 60
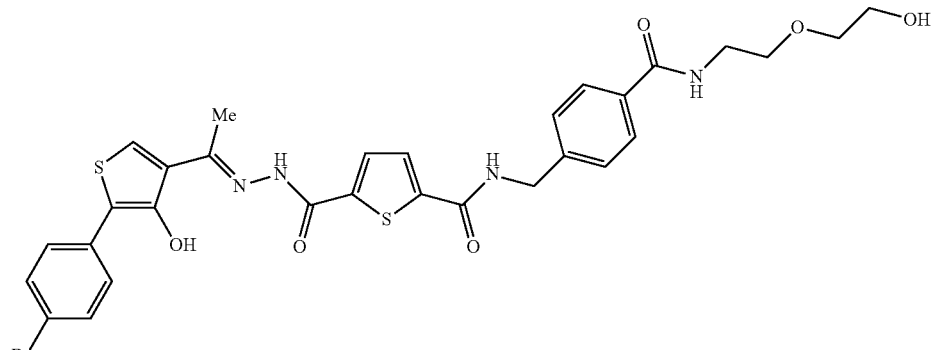
(TCA3-10)  No. 61
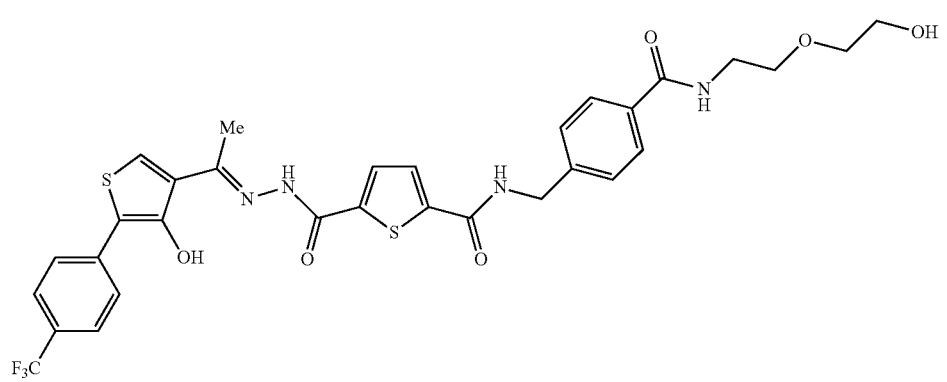
(TCA4-10)  No. 62
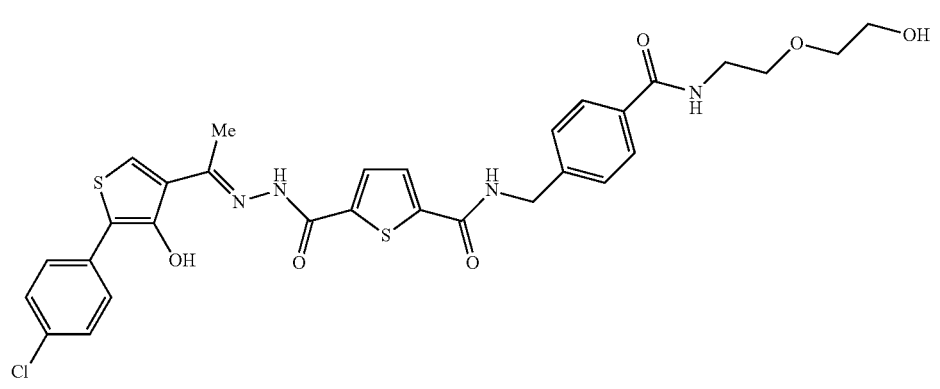
(TCA5-10)  No. 63

-continued
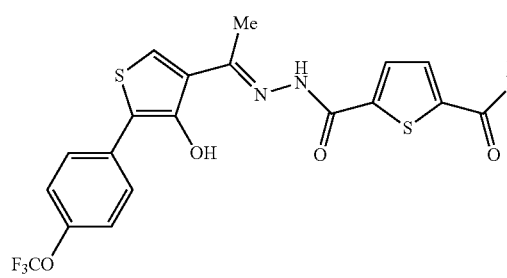
(TCA6-10)
No. 64
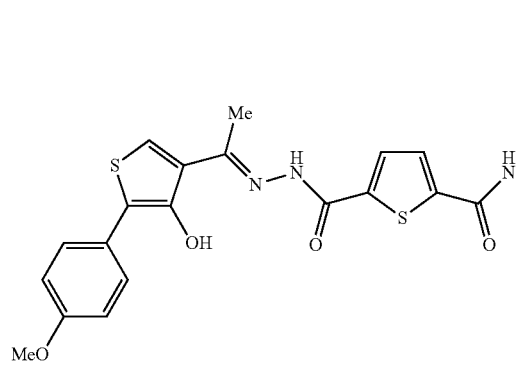
(TCA7-10)
No. 65
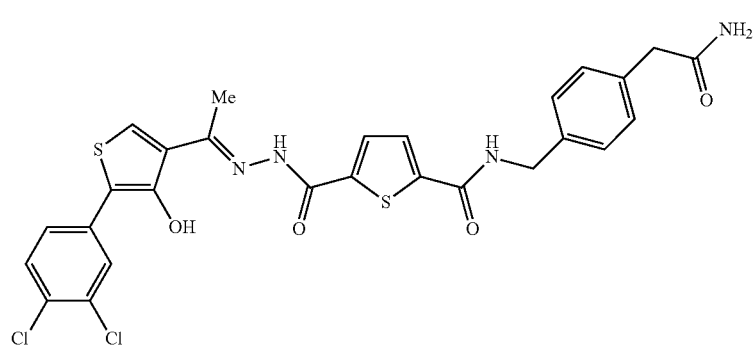
(TCA1-11)
No. 66
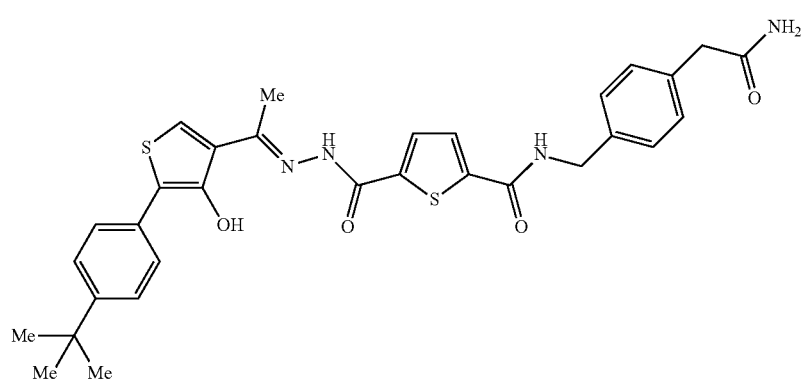
(TCA2-11)
No. 67

-continued
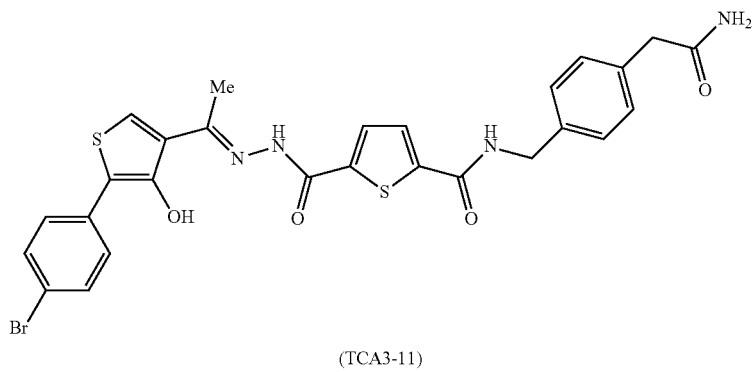
(TCA3-11)
No. 68
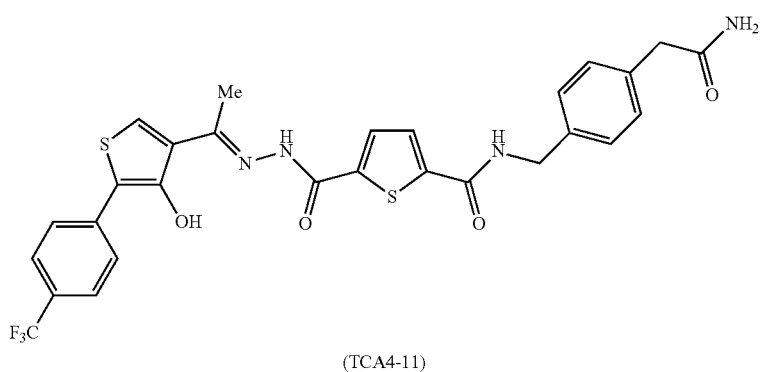
(TCA4-11)
No. 69
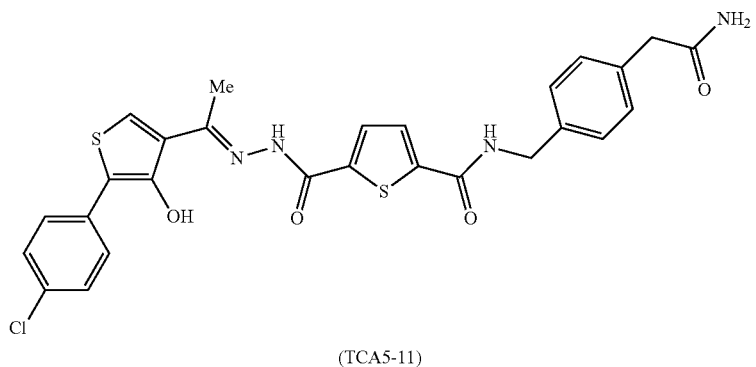
(TCA5-11)
No. 70
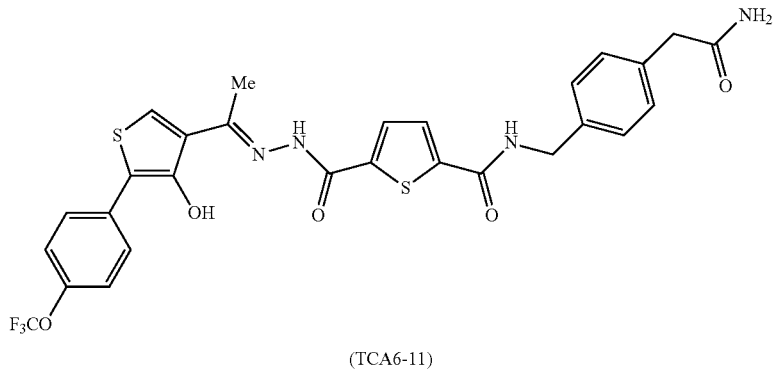
(TCA6-11)
No. 71

-continued

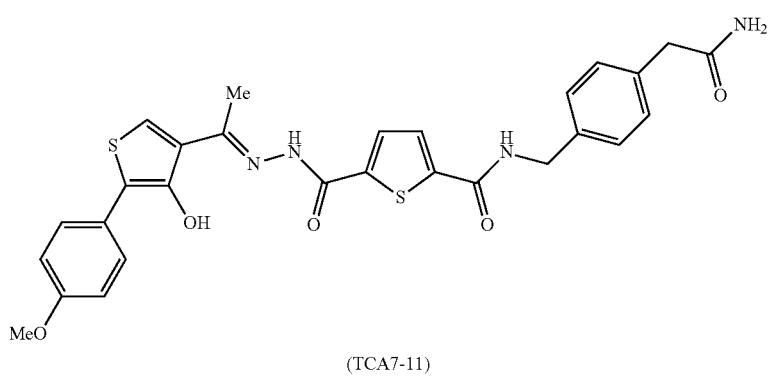

(TCA7-11) No. 72

ASSAY EXAMPLES

The compounds of the present invention were assayed for expansion activity on hematopoietic stem cells and/or hematopoietic progenitor cells below. The $CO_2$ concentration (%) in the $CO_2$ incubator is expressed in the percentage of the volume of $CO_2$ in the atmosphere.

Assay Example 1

Expansion of CD34+ Cells and CD34+CD38− Cells Using Human Cord Blood-Derived CD34+ Cells Human cord blood-derived CD34+ cells were purchased from Lonza and plated on a 24-well plate (Corning) (10000 cells/1 mL/well). As the culture medium, StemSpan SFEM (StemCell Technologies) containing 100 ng/mL SCF (Wako Pure Chemical Industries) was used, and one of Compounds No. 1 to 72 dissolved in dimethyl sulfoxide was added in an amount of 0.1% (v/v) to a final concentration of 1 or 3 µg/mL. As a positive control, TPO (PeproTech) was used at a final concentration of 10 ng/mL.

After the cells were incubated in liquid culture at 37° C. for 7 days in a $CO_2$ incubator (5% $CO_2$), the number of viable cells was counted by trypan blue assay. The number of CD34+ CD38− cells was calculated as follows. After the incubation, the cells in the liquid culture was stained with a CD34 antibody (APC, Becton, Dickinson and Company) and a CD38 antibody (PE, Becton, Dickinson and Company), then washed with PBS(−) containing 2% (v/v) FBS and stained with propidium iodide (Sigma-Aldrich Japan) added to a final concentration of 5 µg/mL. The stained cells were analyzed with a BD FACSCANTO™ II flow cytometer (Becton, Dickinson and Company) to determined the proportions of CD34+ cells and CD34+CD38− cells, which was multiplied by the number of viable cells to calculate the numbers of CD34+ cells and CD34+CD38− cells.

The results demonstrate that the compounds of the present invention showed excellent expansion activity on CD34+ cells and CD34+CD38− cells and have expansion activity on hematopoietic stem cells and hematopoietic progenitor cells.

The expansion efficiencies in the presence of 1 or 3 µg/mL of compounds based on the number of CD34+ cells in the absence of them are shown in Tables 3-1 and 3-2 on a scale of A for expansion efficiencies of 6 or greater, B for expansion efficiencies of at least 4 and less than 6, and C for expansion efficiencies of at least 2 and less than 4. The expansion efficiencies in the presence of 1 or 3 µg/mL of compounds based on the number of CD34+CD38− cells in the absence of them are shown in Tables 4-1 and 4-2 on a scale of A for expansion efficiencies of 10 or greater, B for expansion efficiencies of at least 5 and less than 10, and C for expansion efficiencies of at least 3 and less than 5. Further, in Table 3, the compounds with an expansion efficiency twice or more greater than that of TPO are marked with O.

TABLE 3-1

| Compound No. | Concentration (µg/mL) | Expansion efficiency |
|---|---|---|
| 1 | 3 | C |
| 2 | 3 | B |
| 3 | 3 | C |
| 4 | 3 | C |
| 5 | 3 | B |
| 7 | 3 | C |
| 9 | 3 | C |
| 10 | 3 | B |
| 11 | 3 | A |
| 12 | 3 | A |
| 13 | 3 | A |
| 14 | 1 | A |
| 15 | 3 | A |
| 19 | 3 | C |
| 20 | 3 | B |
| 21 | 3 | A |
| 22 | 3 | A |
| 23 | 3 | A |
| 24 | 3 | A |
| 28 | 3 | B |
| 29 | 3 | A |
| 30 | 3 | A |
| 31 | 3 | C |
| 32 | 3 | A |

TABLE 3-2

| Compound No. | Concentration (µg/mL) | Expansion efficiency |
|---|---|---|
| 33 | 3 | A |
| 34 | 3 | C |
| 35 | 3 | C |
| 36 | 3 | C |
| 37 | 3 | C |
| 38 | 3 | C |
| 44 | 3 | C |
| 52 | 1 | A |
| 53 | 1 | C |
| 54 | 1 | A |
| 55 | 1 | A |
| 56 | 1 | A |
| 57 | 3 | B |

TABLE 3-2-continued

| Compound No. | Concentration (μg/mL) | Expansion efficiency |
|---|---|---|
| 58 | 1 | B |
| 59 | 3 | B |
| 60 | 3 | B |
| 61 | 3 | A |
| 62 | 3 | A |
| 63 | 3 | A |
| 64 | 1 | A |
| 65 | 3 | C |
| 66 | 3 | C |
| 67 | 1 | B |
| 68 | 3 | A |
| 69 | 3 | A |
| 70 | 3 | A |
| 71 | 3 | A |
| 72 | 3 | B |

TABLE 4-1

| Compound No. | Concentration (μg/mL) | Expansion efficiency | Comparison with TPO |
|---|---|---|---|
| 1 | 3 | A | |
| 2 | 3 | A | |
| 3 | 3 | A | |
| 4 | 3 | B | |
| 5 | 3 | A | |
| 6 | 3 | C | |
| 7 | 3 | B | |
| 8 | 3 | B | |
| 9 | 3 | B | |
| 10 | 3 | A | |
| 11 | 3 | A | |
| 12 | 3 | A | |
| 13 | 3 | A | ○ |
| 14 | 1 | A | |
| 15 | 3 | A | ○ |
| 19 | 3 | A | |
| 20 | 3 | A | ○ |
| 21 | 3 | A | ○ |
| 22 | 3 | A | ○ |
| 23 | 3 | A | ○ |
| 24 | 3 | A | ○ |
| 27 | 3 | C | |
| 28 | 3 | A | |
| 29 | 3 | A | ○ |
| 30 | 3 | A | ○ |
| 31 | 3 | A | |
| 32 | 3 | A | ○ |
| 33 | 3 | A | ○ |
| 34 | 3 | B | |
| 35 | 3 | B | |
| 36 | 3 | B | |
| 37 | 3 | A | |

TABLE 4-2

| Compound No. | Concentration (μg/mL) | Expansion efficiency | Comparison with TPO |
|---|---|---|---|
| 38 | 3 | A | |
| 39 | 3 | C | |
| 44 | 3 | A | |
| 47 | 3 | B | |
| 50 | 3 | C | |
| 52 | 1 | A | |
| 53 | 1 | B | |
| 54 | 1 | A | |
| 55 | 1 | A | |
| 56 | 1 | A | |
| 57 | 3 | A | |
| 58 | 1 | A | |
| 59 | 3 | A | ○ |
| 60 | 3 | A | ○ |
| 61 | 3 | A | ○ |
| 62 | 3 | A | ○ |
| 63 | 3 | A | ○ |
| 64 | 1 | A | ○ |
| 65 | 3 | B | |
| 66 | 3 | A | |
| 67 | 1 | A | ○ |
| 68 | 3 | A | ○ |
| 69 | 3 | A | |
| 70 | 3 | A | ○ |
| 71 | 3 | A | |
| 72 | 3 | B | |

Assay Example 2

Expansion of $CD34^+CD38^-$ Cells Using Human Cord Blood-Derived $CD34^+$ Cells

Human cord blood-derived $CD34^+$ cells purchased from the same supplier as in Assay Example 1 were plated on a 24-well plate (Corning) (10000 cells/1 mL/well). As the culture medium, StemSpan SFEM (StemCell Technologies) containing 100 ng/mL SCF (Wako Pure Chemical Industries) was used, and TPO (PeproTech), Flt-3 ligand (Wako Pure Chemical Industries) and Compound No. 60 were added in combinations to final concentrations of 10 ng/mL, 100 ng/mL and 3 μg/mL, respectively.

After the cells were incubated in liquid culture at 37° C. for 7 days in a $CO_2$ incubator (5% $CO_2$), the number of viable cells was counted by trypan blue assay. The number of $CD34^+CD38^-$ cells was calculated in the same manner as in Assay Example 1.

The results demonstrate that the compound of the present invention showed higher expansion activity on $CD34^+CD38^-$ cells than 10 ng/mL TPO in the presence of SCF and in the presence of SCF and FL.

The expansion efficiencies in the presence of 3 μg/mL of the compound and various cytokines based on the number of $CD34^+CD38^-$ cells in the absence of the compound are shown in FIG. 1.

Assay Example 3

Expansion of HPP-CFU Using Human Cord Blood-Derived $CD34^+$ Cells

The effects of Compounds No. 60 and No. 61 of the present invention on hematopoietic progenitor cells were measured by blood cell colony forming assay. The liquid cell cultures obtained in the presence of Compounds No. 60 or No. 61 at a final concentration of 3 μg/mL in the same manner as in Assay Example 1 were poured into 3.5-cm Petri dishes with MethoCult GF H4435 culture medium (StemCell Technologies) at 500 cells/dish and incubated in a $CO_2$ incubator (5% $CO_2$, 37° C.) for 12 days. The number of HPP-CFC colonies in each plate was counted under a microscope routinely. The assay was carried out at least in triplicate, and the numbers of HPP-CFC colonies were averaged.

The results demonstrate that the compounds of the present invention remarkably stimulated formation of HPP-CFU colonies, as compared with the absence of them, and have expansion activity on hematopoietic progenitor cells.

The results are shown in Table 5.

TABLE 5

| Compound No. | Number of HPP-CFC colonies |
|---|---|
| None | 6 |
| 60 | 25 |
| 61 | 14 |

Assay Example 4

Transplantation of Cell Culture into Immunodeficient (NOD/SCID) Mice

Human cord blood-derived $CD34^+$ cells were cultured for 1 week in StemSpan SFEM (StemCell Technologies) containing SCF (Peprotech) at a final concentration of 100 ng/mL and Flt-3 (Wako Pure Chemical Industries) at a final concentration of 100 ng/mL in the presence of TPO (Peprotech) at a final concentration of 20 ng/mL or Compound No. 60 at a final concentration of 3 μg/mL in the same manner as in Assay Example 1. The cell culture were transplanted into at least five 7- to 8-week-old NOD/SCID mice by tail vein injection at $4 \times 10^4$ cells/mouse in terms of the initial number of $CD34^+$ cells after a sublethal dose of irradiation (2.5 Gy). Eight weeks after the transplantation, the mice were killed, and the bone marrow cells were collected from both thighbones. Subsequently, the bone marrow cells were stained with a human CD45 antibody (APC, Becton, Dickinson and Company), then washed with PBS(−) containing 2% (v/v) FBS and stained with propidium iodide (Sigma-Aldrich Japan) added to a final concentration of 5 μg/mL. The stained cells were analyzed with a flow cytometry to determined the proportion of human $CD45^+$ cells in the bone marrow cells. The results demonstrate that the compounds of the present invention has an excellent SRC expanding effect and have expansion activity on hematopoietic stem cells.

The proportion of human $CD45^+$ cells in the mice transplanted with the cell culture incubated in the presence of 3 μg/mL of Compound No. 60 based on the proportion of human $CD45^+$ cells in the mice transplanted with the uncultured human cord blood-derived $CD34^+$ cells are shown in FIG. 2.

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention can expand human hematopoietic stem cells and/or hematopoietic progenitor cells in culture ex vivo in a less differentiated state when used as an active ingredient, as compared with in their absence. Cells expanded by using the compounds of the present invention are useful as a hematopoietic cell transplant for diseases accompanying hematopoietic dysfunction, ischemia or immune dysfunction and hence its application to cell therapy and gene therapy is expected.

The entire disclosure of Japanese Patent Application No. 2009-135495 filed on Jun. 4, 2009 including specification, claims, drawings and summary is incorporated herein by reference in its entirety.

The invention claimed is:
1. A compound of formula (I):

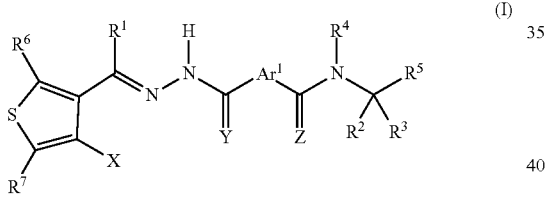

wherein:
$R^1$ is a methyl group;
$R^2$, $R^3$, and $R^4$ are a hydrogen atom;
$R^5$ is a phenyl group, substituted with —$V^1$, —$V^2$, $V^3$, or $V^4$ wherein
—$V^1$ is —$(CH_2)_{m_1}M^1NR^8R^9$,
wherein $M^1$ is —(C=O)— or —($SO_2$)—, $m_1$ is an integer of 0, 1, or 2,
$R^8$ is a hydrogen atom or a $C_{1-3}$ alkyl group, and
when $m_1$=0, $R^9$ is
—$(CH_2)_{m_2}OR^{10}$, wherein $m_2$, is an integer of 1 or 2, and $R^{10}$ is a hydrogen atom, a $C_{1-3}$ alkyl group or —$(CH_2)_{m_3}T$, wherein $m_3$ is an integer of 1 or 2, and T is a hydroxyl group, a $C_{1-6}$ alkoxy group or a $C_{1-6}$ alkyl group,
—$(CH_2)_{m_4}NR^{11}R^{12}$, wherein $m_4$ is an integer of 1 or 2, and each of
$R^{11}$ and $R^{12}$ is independently a hydrogen atom or —$(CH_2)_{m_5}Q$, wherein $m_5$ is an integer of 1 or 2, and Q is a hydroxy group, a $C_{1-3}$ alkoxy group, —$NR^{13}R^{14}$, wherein each of $R^{13}$ and $R^{14}$ is independently a hydrogen atom or a $C_{1-3}$ alkyl group, or $R^{11}$ and $R^{12}$ mean, together with each other as —$NR^{11}R^{12}$, a substituent of formula (II) or (III):

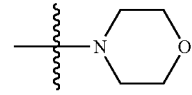

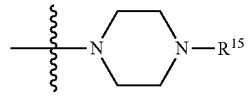

wherein $R^{15}$ is a hydrogen atom, a $C_{1-3}$ alkyl group or an amino-protecting group, and
when $m_1$=1 or 2,
$R^9$ is a hydrogen atom or —$(CH_2)_{m_2}OR^{10}$, wherein $m_2$ is an integer of 1 or 2, and $R^{10}$ is a hydrogen atom, a $C_{1-3}$ alkyl group or —$(CH_2)_{m_3}$ T, wherein $m_3$ is an integer of 1 or 2, and T is a hydroxyl group, a $C_{1-6}$ alkoxy group or a $C_{1-6}$ alkyl group, —$(CH_2)_{m_4}NR^{11}R^{12}$, wherein $m_4$ is an integer of 1 or 2, and each of $R^{11}$ and $R^{12}$ is independently a hydrogen atom or —$(CH_2)_{m_5}Q$, wherein $m_5$ is an integer of 1 or 2, and Q is a hydroxy group, a $C_{1-3}$ alkoxy group, —$NR^{13}R^{14}$, wherein each of $R^{13}$ and $R^{14}$ is independently a hydrogen atom or a $C_{1-3}$ alkyl group, or $R^{11}$ and $R^{12}$ mean, together with each other as —$NR^{11}R^{12}$, a substituent of formula (II) or (III):

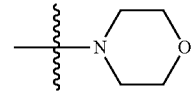

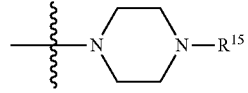

wherein $R^{15}$ is a hydrogen atom, a $C_{1-3}$ alkyl group or an amino-protecting group,
—$V^2$ is —$(CH_2)_{m_6}NR^{16}R^{17}$,
wherein $m_6$ is an integer of 1 or 2, and each of $R^{16}$ and $R^{17}$ is independently a hydrogen atom, a $C_{1-3}$ alkylcarbonyl group or a $C_{1-3}$ alkylsulfonyl group,
—$V^3$ is $M^2NR^{18}(CH_2)_{m_7}R^{19}$,
wherein $M^2$ is —(C=O)— or —($SO_2$)-, $m_7$ is an integer of 1 or 2, $R^{18}$ is a hydrogen atom or a $C_{1-3}$ alkyl group, and $R^{19}$ is a $C_{2-9}$ heterocyclyl group or a $C_{2-14}$ aryl group, and
—$V^4$ is —(C=O)—(piperazine-1,4-diyl)—U;
wherein U is —$(CH_2)_{m_2}OR^{10}$, wherein $m_2$ is an integer of 1 or 2, and $R^{10}$ is a hydrogen atom, a $C_{1-3}$ alkyl group or —$(CH_2)_{m_3}T$, wherein $m_3$ is an integer of 1 or 2, and T is a hydroxyl group, a $C_{1-6}$ alkoxy group or a $C_{1-6}$ alkyl group, —$(CH_2)_{m_4}NR^{11}R^{12}$, wherein $m_4$ is an integer of 1 or 2, and each of $R^{11}$ and $R^{12}$ is independently a hydrogen atom or —$(CH_2)_{m_5}Q$, wherein $m_5$ is an integer of 1 or 2, and Q is a hydroxy group, a $C_{1-3}$ alkoxy group, —$NR^{13}R^{14}$, wherein each of $R^{13}$ and $R^{14}$ is independently a hydrogen atom or a $C_{1-3}$ alkyl group, or $R^{11}$ and $R^{12}$ mean, together with each other as —$NR^{11}R^{12}$, a substituent of formula (II) or (III):

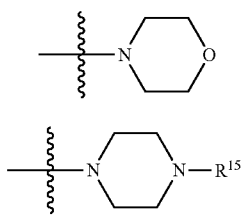
(II)

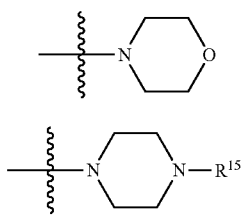
(III)

wherein $R^{15}$ is a hydrogen atom, a $C_{1-3}$ alkyl group or an amino-protecting group;
$R^6$ is a hydrogen atom;
$R^7$ is a phenyl group optionally substituted with one or more of a $C_{1-6}$ alkyl group, a $C_{1-3}$ alkyl group substituted with one or more halogen atoms, a halogen atom, a $C_{1-3}$ alkoxy group, or a $C_{1-3}$ alkoxy group substituted with one or more halogen atoms,
$Ar^1$ is a $C_{4-6}$ arylene substituted with one or more substituents independently represented by $-V^6$,
wherein $V^6$ is a hydrogen atom, a halogen, a $C_{1-3}$ alkoxy group, or a $C_{1-3}$ alkoxy group substituted with a halogen,
X is a hydroxyl group, and
Y and Z are oxygen,
a tautomer, amide, ester, or pharmaceutically acceptable salt of the compound or a solvate thereof.

2. The compound of claim 1, wherein,
$Ar^1$ is formula (IV):

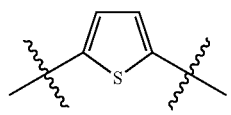
(IV)

a tautomer, and amide, an ester, or a pharmaceutically acceptable salt of the compound or a Solvate thereof.

3. The compound of claim 2, wherein $R^5$ is a phenyl group substituted with one or more substituents of any of formula (V) to (XXII):

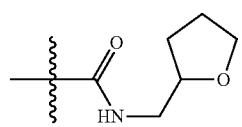
(V)

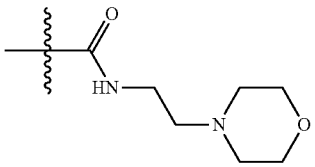
(VI)

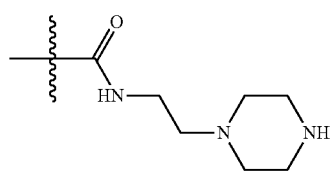
(VII)

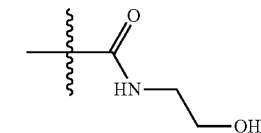
(VIII)

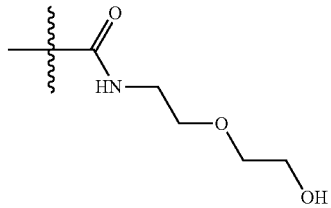
(IX)

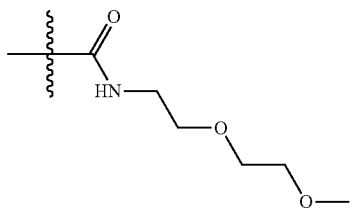
(X)

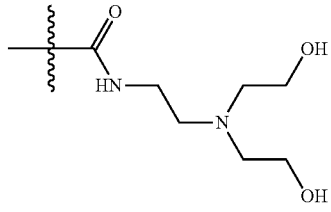
(XI)

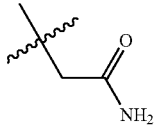
(XII)

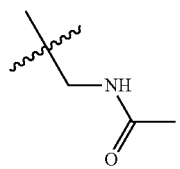
(XIII)

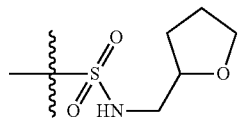
(XIV)

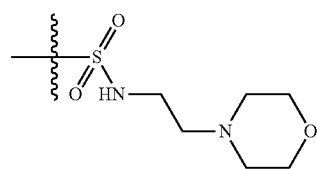
(XV)

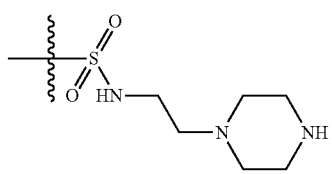
(XVI)

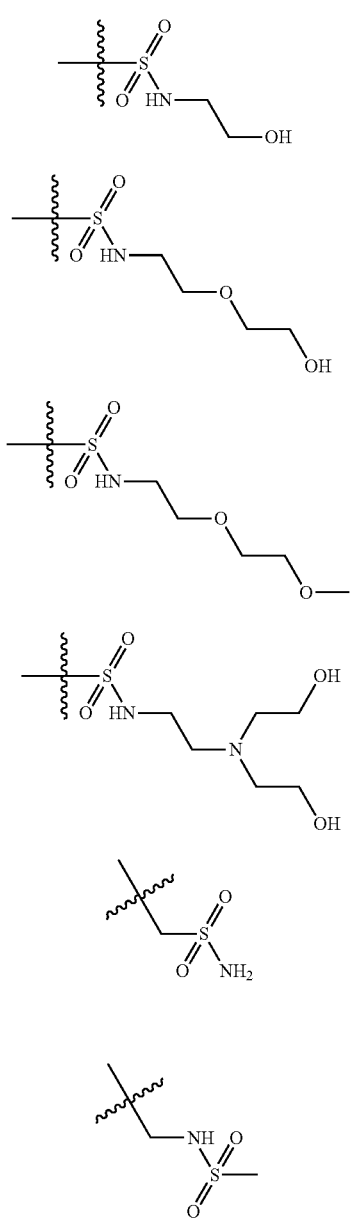

a tautomer, an amide, an ester, or a pharmaceutically acceptable salt of the compound or a solvate thereof.

4. The compound of claim 3, wherein $R^7$ is a phenyl group, substituted with one or more methyl groups, one or more t-butyl groups, one or more halogen atoms, one or more methoxy groups, one or more trifluoromethyl groups or one or more trifluoromethoxy groups, a tautomer, an amide, an ester, or a pharmaceutically acceptable salt of the compound or a solvate thereof.

5. The compound of claim 4, wherein $R^1$ is a methyl group, a tautomer, an amide, an ester, or a pharmaceutically acceptable salt of the compound or a solvate thereof.

6. The compound of claim 5, wherein $R^5$ is a phenyl group substituted with one or more substituents having formula (V);

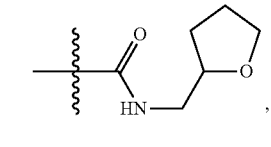

a tautomer, an amide, an ester, or a pharmaceutically acceptable salt of the compound or a solvate thereof.

7. The compound of claim 5, wherein $R^5$ is a phenyl group substituted with one or more substituents having formula (VI);

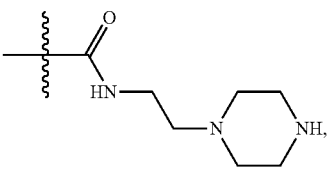

a tautomer, an amide an ester, or a pharmaceutically acceptable salt of the compound or a solvate thereof.

8. The compound of claim 5, wherein $R^5$ is a phenyl group substituted with one or more substituents having foil iula (VII):

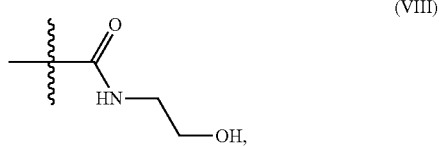 [SMILES: *C(=O)NCCO]

a tautomer, an amide an ester, or a pharmaceutically acceptable salt of the compound or a solvate thereof.

9. The compound of claim 5, wherein $R^5$ is a phenyl group substituted with one or more substituents having formula (VIII);

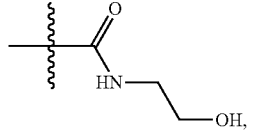

a tautomer, an amide an ester, or a pharmaceutically acceptable salt of the compound or a solvate thereof.

10. The compound of claim 5, wherein $R^5$ is a phenyl group substituted with one or more substituents having formula (IX);

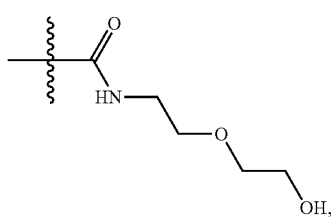

(IX)

a tautomer, an amide an ester, or a pharmaceutically acceptable salt of the compound or a solvate thereof.

11. The compound of claim 5, wherein $R^5$ is a phenyl group substituted with one or more substituents having formula (X);

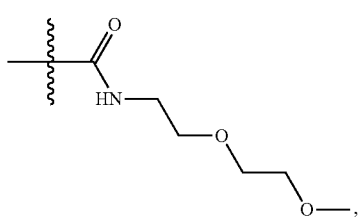

(X)

a tautomer, an amide an ester, or a pharmaceutically acceptable salt of the compound or a solvate thereof.

12. The compound of claim 5, wherein $R^5$ is a phenyl group substituted with one or more substituents having formula (XI);

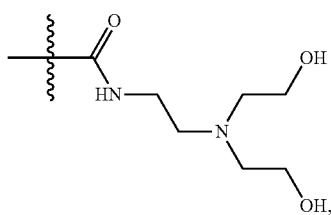

(XI)

a tautomer, an amide an ester, or a pharmaceutically acceptable salt of the compound or a solvate thereof.

13. The compound of claim 5, wherein $R^5$ is a phenyl group substituted with one or more substituents having formula (XII);

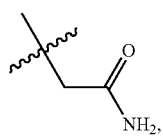

(XII)

a tautomer, an amide an ester, or a pharmaceutically acceptable salt of the compound or a solvate thereof.

14. The compound of claim 5, wherein $R^5$ is a phenyl group substituted with one or more substituents having formula (XIII);

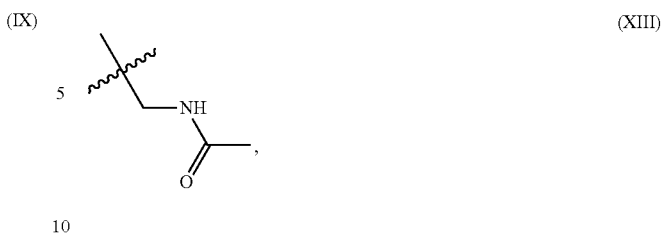

(XIII)

a tautomer, an amide an ester, or a pharmaceutically acceptable salt of the compound or a solvate thereof.

15. The compound of claim 5, wherein $R^5$ is a phenyl group substituted with one or more substituents having formula (XVIII);

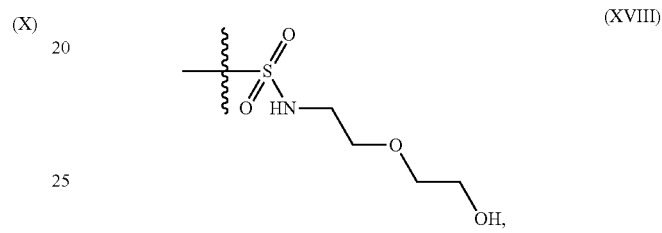

(XVIII)

a tautomer, an amide an ester, or a pharmaceutically acceptable salt of the compound or a solvate thereof.

16. A method for expanding CD34+cells, the method comprising: contacting CD34+cells, in an ex vivo culture, with stem cell factor (SCF) and the compound of claim 1 or, a tautomer, an amide, an ester, or a pharmaceutically acceptable salt of the compound or a solvate thereof.

17. The method of claim 16, further comprising contacting the CD34+cells with at least one factor selected from the group consisting of interleukin-3 (IL-3), interleukin-6 (IL-6), interleukin-11 (IL- 1), flk2/flt3 ligand (FL), granulocyte colony stimulating factor (G-CSF), granulocyte-macrophage colony stimulating factor (GM-CSF), thrombopoietin (TPO), and erythropoietin (EPO).

18. The method of claim 16, further comprising contacting the CD34+cells with flk/flt3 ligand (FL).

19. The method of claim 16, wherein the CD34+cells are obtained from bone marrow, liver, spleen, peripheral blood, or cord blood.

20. The method of claim 19, wherein the CD34+cells are obtained from cord blood.

21. The method of claim 20, further comprising contacting the CD34+cells with flk/flt3 ligand (FL).

22. A composition comprising, the compound of claim 1, a tautomer, an amide an ester, or a pharmaceutically acceptable salt of the compound or a solvate thereof; and a pharmaceutically acceptable additive.

23. The compound of claim 1, wherein $R^7$ is a phenyl group optionally substituted with one or more of a methyl, t-butyl, halogen, methoxy, trifluoromethyl, or trifluoromethoxy.

24. The compound of claim 1, wherein $Ar^1$ is thiophene-diyl, phenylene, or pyridinediyl.

25. The compound of claim 1, wherein $Ar^1$ is one of the following formulas

-continued
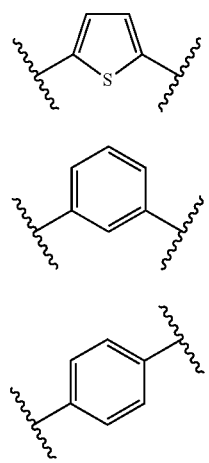
A[1]
A[2]
A[3]
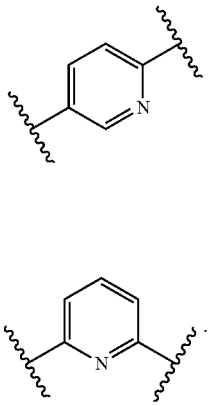
A[4]
A[5]
* * * * *